United States Patent
Johnson et al.

(10) Patent No.: US 10,646,283 B2
(45) Date of Patent: May 12, 2020

(54) AUGMENTED REALITY NAVIGATION SYSTEMS FOR USE WITH ROBOTIC SURGICAL SYSTEMS AND METHODS OF THEIR USE

(71) Applicant: GLOBUS MEDICAL, INC., Audubon, PA (US)

(72) Inventors: Norbert Johnson, North Andover, MD (US); Jeffrey Forsyth, Cranston, RI (US); Neil Crawford, Chandler, AZ (US); Sanjay Joshi, Andover, MA (US); Bessam Al Jewad, Madbury, NH (US); Weston Healy, Cambridge, MA (US); Christine Russ, Stoneham, MA (US); Ken Jones, Wellesley, MA (US)

(73) Assignee: Globus Medical Inc., Audubon, PA (US)

( * ) Notice: Subject to any disclaimer, the term of this patent is extended or adjusted under 35 U.S.C. 154(b) by 24 days.

(21) Appl. No.: 15/902,053

(22) Filed: Feb. 22, 2018

(65) Prior Publication Data
US 2019/0254754 A1    Aug. 22, 2019

Related U.S. Application Data

(63) Continuation of application No. 15/899,038, filed on Feb. 19, 2018.

(51) Int. Cl.
*A61B 34/20* (2016.01)
*G02B 27/01* (2006.01)
(Continued)

(52) U.S. Cl.
CPC .............. *A61B 34/20* (2016.02); *A61B 34/30* (2016.02); *G02B 27/017* (2013.01); *G06F 3/011* (2013.01);
(Continued)

(58) Field of Classification Search
None
See application file for complete search history.

(56) References Cited

U.S. PATENT DOCUMENTS 4,150,293 A    4/1979 Franke
4,722,056 A    1/1988 Roberts et al.
(Continued)

OTHER PUBLICATIONS

US 8,231,638 B2, 07/2012, Swarup et al. (withdrawn)

*Primary Examiner* — Yingchun He

(57) ABSTRACT

The present disclosure is directed to augmented reality navigation systems and methods of their use that, inter alia, address the need for systems and methods of robotic surgical system navigation with reduced distraction to surgeons. Augmented reality navigation systems disclosed herein enable a surgeon to maintain focus on a surgical site and/or surgical tool being used in a surgical procedure while obtaining a wide range of navigational information relevant to the procedure. Navigational information can appear in the augmented reality navigation system as being presented on virtual displays that sit in a natural field of view of a surgeon during a procedure. Navigational information can also appear to be overlaid over a patient's anatomy. Augmented reality navigation systems comprise a head mounted display comprising an at least partially transparent display screen, at least one detector connected to the head mounted display for identifying real-world features, and a computer subsystem.

20 Claims, 17 Drawing Sheets

(51) Int. Cl.
  *G06F 3/01*      (2006.01)
  *G06T 19/00*     (2011.01)
  *G16H 20/40*     (2018.01)
  *A61B 34/30*     (2016.01)
  *G16H 50/50*     (2018.01)
  *G16H 40/63*     (2018.01)
  *A61B 90/00*     (2016.01)
  *A61B 34/00*     (2016.01)
  *A61B 34/10*     (2016.01)
  *A61B 17/00*     (2006.01)
  *A61B 90/50*     (2016.01)

(52) U.S. Cl.
  CPC ........... *G06T 19/006* (2013.01); *G16H 20/40* (2018.01); *G16H 40/63* (2018.01); *G16H 50/50* (2018.01); *A61B 2017/00203* (2013.01); *A61B 2017/00207* (2013.01); *A61B 2017/00216* (2013.01); *A61B 2034/107* (2016.02); *A61B 2034/2048* (2016.02); *A61B 2034/2057* (2016.02); *A61B 2034/2068* (2016.02); *A61B 2034/2074* (2016.02); *A61B 2034/254* (2016.02); *A61B 2034/256* (2016.02); *A61B 2034/258* (2016.02); *A61B 2090/365* (2016.02); *A61B 2090/3616* (2016.02); *A61B 2090/371* (2016.02); *A61B 2090/372* (2016.02); *A61B 2090/374* (2016.02); *A61B 2090/376* (2016.02); *A61B 2090/378* (2016.02); *A61B 2090/502* (2016.02)

(56) References Cited

U.S. PATENT DOCUMENTS

| | | |
|---|---|---|
| 5,246,010 A | 9/1993 | Gazzara et al. |
| 5,354,314 A | 10/1994 | Hardy et al. |
| 5,397,323 A | 3/1995 | Taylor et al. |
| 5,526,812 A | 6/1996 | Dumoulin et al. |
| 5,598,453 A | 1/1997 | Baba et al. |
| 5,740,802 A | 4/1998 | Nafis et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,961,456 A | 10/1999 | Gildenberg |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,226,548 B1 | 5/2001 | Foley et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,349,001 B1 | 2/2002 | Spitzer |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,503,195 B1 | 1/2003 | Keller et al. |
| 6,507,751 B2 | 1/2003 | Blume et al. |
| 6,535,756 B1 | 3/2003 | Simon et al. |
| 6,544,176 B2 | 4/2003 | Mikus et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,725,080 B2 | 4/2004 | Melkent et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,324 B2 | 2/2005 | Sauer et al. |
| 6,856,826 B2 | 2/2005 | Seeley et al. |
| 6,856,827 B2 | 2/2005 | Seeley et al. |
| 6,867,753 B2 | 3/2005 | Chinthammit et al. |
| 6,879,880 B2 | 4/2005 | Nowlin et al. |
| 6,892,090 B2 | 5/2005 | Verard et al. |
| 6,919,867 B2 | 7/2005 | Sauer |
| 6,920,347 B2 | 7/2005 | Simon et al. |
| 6,922,632 B2 | 7/2005 | Foxlin |
| 6,947,786 B2 | 9/2005 | Simon et al. |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,050,845 B2 | 5/2006 | Vilsmeier |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,176,936 B2 | 2/2007 | Sauer et al. |
| 7,194,120 B2 | 3/2007 | Wicker et al. |
| 7,197,107 B2 | 3/2007 | Arai et al. |

(56) References Cited

U.S. PATENT DOCUMENTS

| | | |
|---|---|---|
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,480,402 B2 | 1/2009 | Bar-Zohar et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,570,791 B2 | 8/2009 | Frank et al. |
| 7,594,912 B2 | 9/2009 | Cooper et al. |
| 7,599,730 B2 | 10/2009 | Hunter et al. |
| 7,605,826 B2 | 10/2009 | Sauer |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,774,044 B2 | 8/2010 | Sauer et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Willliams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,987,001 B2 | 7/2011 | Teichman et al. |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,106,905 B2 | 1/2012 | Markowitz et al. |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |

(56) References Cited

U.S. PATENT DOCUMENTS

| | | |
|---|---|---|
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,314,815 B2 | 11/2012 | Navab et al. |
| 8,320,991 B2 | 11/2012 | Jascob et al. |
| 8,325,873 B2 | 12/2012 | Helm et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,427,527 B2 | 4/2013 | Visser et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,136 B1 | 8/2013 | Sun et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,509,503 B2 | 8/2013 | Nahum et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,672,836 B2 | 3/2014 | Higgins et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,774,363 B2 | 7/2014 | Van Den Houten et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,784,443 B2 | 7/2014 | Tripathi |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,842,893 B2 | 9/2014 | Teichman et al. |

(56) References Cited

U.S. PATENT DOCUMENTS

| | | |
|---|---|---|
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,878,900 B2 | 11/2014 | Yang et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,891,847 B2 | 11/2014 | Helm et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,938,283 B2 | 1/2015 | Zentgraf et al. |
| 8,938,301 B2 | 1/2015 | Hagedorn |
| 8,945,140 B2 | 2/2015 | Hubschman et al. |
| 8,948,935 B1 | 2/2015 | Peeters et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,095,252 B2 | 8/2015 | Popovic |
| 9,105,207 B2 | 8/2015 | Leung |
| 9,107,683 B2 | 8/2015 | Hourtash et al. |
| 9,119,670 B2 | 9/2015 | Yang et al. |
| 9,123,155 B2 | 9/2015 | Cunningham et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,232,982 B2 | 1/2016 | Soler et al. |
| 9,265,468 B2 | 2/2016 | Rai et al. |
| 9,289,267 B2 | 3/2016 | Sauer et al. |
| 9,295,435 B2 | 3/2016 | Florent et al. |
| 9,308,050 B2 | 4/2016 | Kostrzewski et al. |
| 9,333,361 B2 | 5/2016 | Li et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,436,993 B1 | 9/2016 | Stolka et al. |
| 9,439,556 B2 | 9/2016 | Pandya et al. |
| 9,492,235 B2 | 11/2016 | Hourtash et al. |
| 9,492,241 B2 | 11/2016 | Jaskowicz et al. |
| 9,498,132 B2 | 11/2016 | Maier-Hein et al. |
| 9,538,962 B1 | 1/2017 | Hannaford et al. |
| 9,547,940 B1 | 1/2017 | Sun et al. |
| 9,554,866 B2 | 1/2017 | Cunningham et al. |
| 9,563,266 B2 | 2/2017 | Banerjee et al. |
| 9,576,106 B2 | 2/2017 | Ahmad |
| 9,592,096 B2 | 3/2017 | Maillet et al. |
| 9,626,805 B2 | 4/2017 | Lampotang et al. |
| 9,645,379 B2 | 5/2017 | Ren et al. |
| 9,675,319 B1* | 6/2017 | Razzaque ............ A61B 8/0841 |
| 9,681,925 B2 | 6/2017 | Azar et al. |
| 9,707,400 B2 | 7/2017 | Grenz et al. |
| 9,750,465 B2 | 9/2017 | Engel et al. |
| 9,757,203 B2 | 9/2017 | Hourtash et al. |
| 9,767,608 B2 | 9/2017 | Lee et al. |
| 9,773,312 B2 | 9/2017 | Lee |
| 9,788,756 B2 | 10/2017 | Demmer |
| 9,795,282 B2 | 10/2017 | Sholev et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,833,254 B1 | 12/2017 | Barral et al. |
| 9,835,862 B1 | 12/2017 | Zhou et al. |
| 9,839,365 B1 | 12/2017 | Homyk et al. |
| 9,848,922 B2 | 12/2017 | Tohmeh et al. |
| 9,855,103 B2 | 1/2018 | Tsekos et al. |
| 9,892,564 B1 | 2/2018 | Cvetko et al. |
| 9,895,063 B1 | 2/2018 | Hannaford et al. |
| 9,898,662 B2 | 2/2018 | Tsuda et al. |
| 9,911,187 B2 | 3/2018 | Steinle et al. |
| 9,925,011 B2 | 3/2018 | Gombert et al. |
| 9,925,013 B2 | 3/2018 | Dell et al. |
| 9,928,629 B2 | 3/2018 | Benishti et al. |
| 9,931,025 B1 | 4/2018 | Graetzel et al. |
| 9,931,040 B2 | 4/2018 | Homyk et al. |
| 9,949,637 B1 | 4/2018 | Wong et al. |
| 9,970,955 B1 | 5/2018 | Homyk et al. |
| 9,980,698 B2 | 5/2018 | Bakker et al. |
| 10,010,373 B2 | 7/2018 | Canfield et al. |
| 10,010,379 B1 | 7/2018 | Gibby et al. |
| 10,013,808 B2 | 7/2018 | Jones et al. |
| 10,016,243 B2 | 7/2018 | Esterberg |
| 10,034,717 B2 | 7/2018 | Miller et al. |
| 10,052,170 B2 | 8/2018 | Saget et al. |
| 10,073,515 B2 | 9/2018 | Awdeh |
| 10,092,164 B2 | 10/2018 | Sholev et al. |
| 10,092,237 B2 | 10/2018 | Wong et al. |
| 10,092,361 B2 | 10/2018 | Ferro et al. |
| 10,105,187 B2 | 10/2018 | Corndorf et al. |
| 10,152,789 B2 | 12/2018 | Carnes et al. |
| 10,152,796 B2 | 12/2018 | Guo et al. |
| 10,154,239 B2 | 12/2018 | Casas |
| 10,163,252 B2 | 12/2018 | Yun et al. |
| 10,166,019 B2 | 1/2019 | Nawana et al. |
| 10,176,642 B2 | 1/2019 | Tran et al. |
| 10,191,615 B2 | 1/2019 | Helm et al. |
| 10,194,990 B2 | 2/2019 | Amanatullah et al. |
| 10,195,076 B2 | 2/2019 | Fateh |
| 10,197,803 B2 | 2/2019 | Badiali et al. |
| 10,197,816 B2 | 2/2019 | Waisman et al. |
| 10,226,298 B2 | 3/2019 | Ourselin et al. |
| 10,231,784 B2 | 3/2019 | Hettrick et al. |
| 10,235,737 B2 | 3/2019 | Cheatham, III et al. |
| 10,242,292 B2 | 3/2019 | Zisimopoulos et al. |
| 10,251,714 B2 | 4/2019 | Carnes et al. |
| 10,258,426 B2 | 4/2019 | Silva et al. |
| 10,265,138 B2 | 4/2019 | Choudhry et al. |
| 10,275,927 B2 | 4/2019 | Kuhn et al. |
| 10,278,726 B2 | 5/2019 | Barth et al. |
| 10,285,765 B2 | 5/2019 | Sachs et al. |
| 10,292,780 B2 | 5/2019 | Park |
| 10,360,730 B2 | 7/2019 | Hasegwa |
| 10,366,489 B2 | 7/2019 | Boettger et al. |
| 10,376,318 B2 | 8/2019 | Tsusaka et al. |
| 10,379,048 B2 | 8/2019 | Wang et al. |
| 10,383,654 B2 | 8/2019 | Yilmaz et al. |
| 10,390,780 B2 | 8/2019 | Han et al. |
| 10,390,890 B2 | 8/2019 | Jagga |
| 10,390,891 B2 | 8/2019 | Govari et al. |
| 10,398,514 B2 | 9/2019 | Ryan et al. |
| 10,405,927 B1 | 9/2019 | Lang |
| 10,412,377 B2 | 9/2019 | Forthmann et al. |
| 10,413,363 B2 | 9/2019 | Fahim et al. |
| 10,426,339 B2 | 10/2019 | Papac |
| 10,426,345 B2 | 10/2019 | Shekhar et al. |
| 10,426,554 B2 | 10/2019 | Siewerdsen et al. |
| 10,431,008 B2 | 10/2019 | Djajadiningrat et al. |
| 10,432,913 B2 | 10/2019 | Shokri et al. |
| 10,433,915 B2 | 10/2019 | Isaacs et al. |
| 10,448,003 B2 | 10/2019 | Gafenberg |
| 2001/0036302 A1 | 11/2001 | Miller |
| 2002/0035321 A1 | 3/2002 | Bucholz et al. |
| 2003/0179308 A1 | 9/2003 | Zamorano et al. |
| 2003/0210812 A1 | 11/2003 | Khamene et al. |
| 2004/0068172 A1 | 4/2004 | Nowinski et al. |
| 2004/0076259 A1 | 4/2004 | Jensen et al. |
| 2004/0106916 A1 | 6/2004 | Quaid et al. |

(56) References Cited

U.S. PATENT DOCUMENTS

| | | |
|---|---|---|
| 2004/0254454 A1 | 12/2004 | Kockro |
| 2005/0054910 A1 | 3/2005 | Tremblay et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2005/0203380 A1* | 9/2005 | Sauer .............. G02B 7/002 600/417 |
| 2005/0215879 A1 | 9/2005 | Chuanggui |
| 2006/0100610 A1 | 5/2006 | Wallace et al. |
| 2006/0173329 A1 | 8/2006 | Marquart et al. |
| 2006/0176242 A1 | 8/2006 | Jaramaz et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2006/0293557 A1 | 12/2006 | Chuanggui et al. |
| 2007/0015987 A1 | 1/2007 | Benlloch Baviera et al. |
| 2007/0021738 A1 | 1/2007 | Hasset et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167702 A1 | 7/2007 | Nasser et al. |
| 2007/0167712 A1 | 7/2007 | Keglovich et al. |
| 2007/0233238 A1 | 10/2007 | Huynh et al. |
| 2007/0236514 A1 | 10/2007 | Agusanto et al. |
| 2007/0238981 A1 | 10/2007 | Zhu et al. |
| 2007/0248261 A1 | 10/2007 | Zhou et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | von Jako |
| 2008/0109012 A1 | 5/2008 | Falco et al. |
| 2008/0123910 A1 | 5/2008 | Zhu |
| 2008/0144906 A1 | 6/2008 | Allred et al. |
| 2008/0161680 A1 | 7/2008 | von Jako et al. |
| 2008/0161682 A1 | 7/2008 | Kendrick et al. |
| 2008/0177203 A1 | 7/2008 | von Jako |
| 2008/0183068 A1 | 7/2008 | Carls et al. |
| 2008/0183074 A1 | 7/2008 | Carls et al. |
| 2008/0183188 A1 | 7/2008 | Carls et al. |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0243142 A1 | 10/2008 | Gildenberg |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0210902 A1 | 8/2010 | Navab et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0059378 A1 | 3/2012 | Farrell |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0203067 A1 | 8/2012 | Higgins et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2012/0302875 A1 | 11/2012 | Kohring |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211232 A1 | 8/2013 | Murphy et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0267838 A1 | 10/2013 | Fronk et al. |
| 2013/0272488 A1 | 10/2013 | Bailey et al. |
| 2013/0272489 A1 | 10/2013 | Dickman et al. |
| 2013/0274596 A1 | 10/2013 | Azizian et al. |
| 2013/0274761 A1 | 10/2013 | Devengenzo et al. |

(56) References Cited

U.S. PATENT DOCUMENTS

| | | |
|---|---|---|
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0022283 A1 | 1/2014 | Chan et al. |
| 2014/0031664 A1 | 1/2014 | Kang et al. |
| 2014/0044333 A1 | 2/2014 | Barth, Jr. et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0139405 A1 | 5/2014 | Ribble et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0206994 A1 | 7/2014 | Jain et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0347353 A1 | 11/2014 | Popovic et al. |
| 2014/0364720 A1 | 12/2014 | Darrow et al. |
| 2014/0371577 A1 | 12/2014 | Mallet et al. |
| 2015/0025547 A1* | 1/2015 | Hannaford ............ G06F 3/011 606/130 |
| 2015/0031990 A1 | 1/2015 | Boctor et al. |
| 2015/0039034 A1 | 2/2015 | Frankel et al. |
| 2015/0073265 A1 | 3/2015 | Popovic et al. |
| 2015/0084990 A1 | 3/2015 | Laor |
| 2015/0085970 A1 | 3/2015 | Bouhnik et al. |
| 2015/0112126 A1 | 4/2015 | Popovic et al. |
| 2015/0146847 A1 | 5/2015 | Liu |
| 2015/0146946 A1 | 5/2015 | Elhawary et al. |
| 2015/0150524 A1 | 6/2015 | Yorkston et al. |
| 2015/0196261 A1 | 7/2015 | Funk |
| 2015/0201892 A1 | 7/2015 | Hummel et al. |
| 2015/0213633 A1 | 7/2015 | Chang et al. |
| 2015/0230689 A1 | 8/2015 | Blohm et al. |
| 2015/0238276 A1 | 8/2015 | Atarot et al. |
| 2015/0248793 A1 | 9/2015 | Abovitz et al. |
| 2015/0305828 A1 | 10/2015 | Park et al. |
| 2015/0335480 A1 | 11/2015 | Alvarez et al. |
| 2015/0342647 A1 | 12/2015 | Frankel et al. |
| 2015/0366624 A1 | 12/2015 | Kostrzewski et al. |
| 2015/0366628 A1 | 12/2015 | Ingmanson |
| 2016/0005194 A1 | 1/2016 | Schretter et al. |
| 2016/0015469 A1 | 1/2016 | Goshayesh et al. |
| 2016/0015470 A1 | 1/2016 | Border |
| 2016/0018640 A1 | 1/2016 | Haddick et al. |
| 2016/0018641 A1 | 1/2016 | Haddick et al. |
| 2016/0018642 A1 | 1/2016 | Haddick et al. |
| 2016/0019715 A1 | 1/2016 | Haddick et al. |
| 2016/0019716 A1 | 1/2016 | Huang et al. |
| 2016/0019719 A1 | 1/2016 | Osterhout et al. |
| 2016/0021304 A1 | 1/2016 | Osterhout |
| 2016/0022125 A1 | 1/2016 | Nicolau et al. |
| 2016/0035139 A1* | 2/2016 | Fuchs ................. G02B 27/017 345/633 |
| 2016/0086380 A1 | 3/2016 | Vayser et al. |
| 2016/0163105 A1 | 6/2016 | Hong et al. |
| 2016/0166329 A1 | 6/2016 | Langan et al. |
| 2016/0225192 A1* | 8/2016 | Jones ...................... G06F 3/012 |
| 2016/0235485 A1 | 8/2016 | Scholl et al. |
| 2016/0249989 A1 | 9/2016 | Devam et al. |
| 2016/0249990 A1 | 9/2016 | Glozman et al. |
| 2016/0287337 A1 | 10/2016 | Aram et al. |
| 2016/0302871 A1 | 10/2016 | Gregerson et al. |
| 2016/0317119 A1 | 11/2016 | Tahmasebi Maraghoosh et al. |
| 2016/0320322 A1 | 11/2016 | Suzuki |
| 2016/0324580 A1 | 11/2016 | Esterberg |
| 2016/0324598 A1 | 11/2016 | Bothorel et al. |
| 2016/0331335 A1 | 11/2016 | Gregerson et al. |
| 2016/0360117 A1 | 12/2016 | Elefteriu et al. |
| 2017/0035517 A1 | 2/2017 | Eri et al. |
| 2017/0053437 A1 | 2/2017 | Ye et al. |
| 2017/0099479 A1 | 4/2017 | Browd et al. |
| 2017/0119471 A1 | 5/2017 | Winner et al. |
| 2017/0119474 A1 | 5/2017 | Kronman |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0151034 A1 | 6/2017 | Oda et al. |
| 2017/0156816 A1 | 6/2017 | Ibrahim |
| 2017/0172381 A1 | 6/2017 | Morimoto |
| 2017/0172663 A1 | 6/2017 | Popovic et al. |
| 2017/0202624 A1 | 7/2017 | Atarot et al. |
| 2017/0202629 A1 | 7/2017 | Maillet et al. |
| 2017/0202633 A1 | 7/2017 | Liu |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0224427 A1 | 8/2017 | Lavallee et al. |
| 2017/0231710 A1 | 8/2017 | Scholl et al. |
| 2017/0231714 A1 | 8/2017 | Kosmecki et al. |
| 2017/0236464 A1* | 8/2017 | Koshihara ............ G09G 3/2003 345/694 |
| 2017/0251900 A1 | 9/2017 | Hansen et al. |
| 2017/0256095 A1 | 9/2017 | Bani-Hashemi |
| 2017/0258426 A1 | 9/2017 | Risher-Kelly et al. |
| 2017/0273549 A1 | 9/2017 | Nazareth et al. |
| 2017/0273748 A1 | 9/2017 | Hourtash et al. |

(56) References Cited

U.S. PATENT DOCUMENTS

| | | |
|---|---|---|
| 2017/0296277 A1 | 10/2017 | Hourtash et al. |
| 2017/0296292 A1 | 10/2017 | Mahmood et al. |
| 2017/0315364 A1 | 11/2017 | Viasumoto |
| 2017/0322410 A1 | 11/2017 | Watson et al. |
| 2017/0323062 A1 | 11/2017 | Djajadiningrat et al. |
| 2017/0336870 A1 | 11/2017 | Everett et al. |
| 2017/0360493 A1 | 12/2017 | Zucker et al. |
| 2017/0367766 A1 | 12/2017 | Mahfouz |
| 2017/0367771 A1 | 12/2017 | Tako et al. |
| 2018/0021099 A1 | 1/2018 | Warner et al. |
| 2018/0032130 A1 | 2/2018 | Meglan |
| 2018/0042692 A1 | 2/2018 | Kim et al. |
| 2018/0049809 A1 | 2/2018 | Marti et al. |
| 2018/0071032 A1 | 3/2018 | De Almeida Barreto |
| 2018/0078316 A1 | 3/2018 | Schaewe et al. |
| 2018/0082480 A1 | 3/2018 | White et al. |
| 2018/0092698 A1 | 4/2018 | Chopra et al. |
| 2018/0092706 A1 | 4/2018 | Anderson et al. |
| 2018/0116724 A1 | 5/2018 | Gmeiner et al. |
| 2018/0116732 A1 | 5/2018 | Lin et al. |
| 2018/0125586 A1 | 5/2018 | Sela et al. |
| 2018/0140362 A1 | 5/2018 | Cali et al. |
| 2018/0158201 A1 | 6/2018 | Thompson et al. |
| 2018/0161102 A1 | 6/2018 | Wei et al. |
| 2018/0168730 A1 | 6/2018 | Nazy |
| 2018/0168741 A1 | 6/2018 | Swayze et al. |
| 2018/0168769 A1 | 6/2018 | Wood et al. |
| 2018/0185100 A1 | 7/2018 | Weinstein et al. |
| 2018/0220100 A1 | 8/2018 | Ovchinnikov et al. |
| 2018/0228555 A1 | 8/2018 | Charron et al. |
| 2018/0232925 A1 | 8/2018 | Frakes et al. |
| 2018/0233222 A1 | 8/2018 | Daley et al. |
| 2018/0235739 A1 | 8/2018 | Jahn |
| 2018/0247449 A1 | 8/2018 | Park et al. |
| 2018/0249912 A1 | 9/2018 | Schneider et al. |
| 2018/0256256 A1 | 9/2018 | May et al. |
| 2018/0263698 A1 | 9/2018 | Wang et al. |
| 2018/0263727 A1 | 9/2018 | Pellerito |
| 2018/0289428 A1 | 10/2018 | Lee et al. |
| 2018/0289983 A1 | 10/2018 | Fishman |
| 2018/0299675 A1 | 10/2018 | Benz et al. |
| 2018/0303377 A1 | 10/2018 | West et al. |
| 2018/0303558 A1 | 10/2018 | Thomas |
| 2018/0303667 A1 | 10/2018 | Peyman |
| 2018/0310811 A1 | 11/2018 | Vieglan et al. |
| 2018/0310831 A1 | 11/2018 | Cheng et al. |
| 2018/0310875 A1 | 11/2018 | Meglan et al. |
| 2018/0325604 A1 | 11/2018 | Atarot et al. |
| 2018/0325618 A1 | 11/2018 | Justin et al. |
| 2018/0333073 A1 | 11/2018 | Hill et al. |
| 2018/0333207 A1 | 11/2018 | Moctezuma D La Barrera |
| 2018/0333208 A1 | 11/2018 | Kotian et al. |
| 2018/0344266 A1 | 12/2018 | Altmann |
| 2018/0344408 A1 | 12/2018 | Rotilio et al. |
| 2018/0357825 A1 | 12/2018 | Hoffmann et al. |
| 2018/0360310 A1 | 12/2018 | Berlin |
| 2018/0368930 A1 | 12/2018 | Esterberg et al. |
| 2019/0000564 A1 | 1/2019 | Navab et al. |
| 2019/0000570 A1 | 1/2019 | Esterberg et al. |
| 2019/0008592 A1 | 1/2019 | Thienphrapa et al. |
| 2019/0011709 A1 | 1/2019 | Yadav et al. |
| 2019/0015162 A1 | 1/2019 | Abhari et al. |
| 2019/0015167 A1 | 1/2019 | Draelos et al. |
| 2019/0029757 A1 | 1/2019 | Roh et al. |
| 2019/0035156 A1 | 1/2019 | Wei et al. |
| 2019/0038362 A1 | 2/2019 | Nash et al. |
| 2019/0046276 A1 | 2/2019 | Inglese et al. |
| 2019/0050665 A1 | 2/2019 | Sakuragi |
| 2019/0053851 A1 | 2/2019 | Siemionow et al. |
| 2019/0053855 A1 | 2/2019 | Siemionow et al. |
| 2019/0053858 A1 | 2/2019 | Kapoor et al. |
| 2019/0054632 A1 | 2/2019 | Grafenberg et al. |
| 2019/0059773 A1 | 2/2019 | Laughlin et al. |
| 2019/0066260 A1 | 2/2019 | Suehling et al. |
| 2019/0066390 A1 | 2/2019 | Vogel et al. |
| 2019/0069962 A1 | 3/2019 | Tabandeh et al. |
| 2019/0076194 A1 | 3/2019 | Jang |
| 2019/0080515 A1 | 3/2019 | Geri et al. |
| 2019/0088162 A1 | 3/2019 | Meglan |
| 2019/0090955 A1 | 3/2019 | Singh et al. |
| 2019/0099221 A1 | 4/2019 | Schmidt et al. |
| 2019/0104919 A1 | 4/2019 | Shelton, IV et al. |
| 2019/0108654 A1 | 4/2019 | Lasserre et al. |
| 2019/0117190 A1 | 4/2019 | Djajadonongrat |
| 2019/0122443 A1 | 4/2019 | Stocker |
| 2019/0125361 A1 | 5/2019 | Shelton, IV et al. |
| 2019/0125454 A1 | 5/2019 | Shelton, IV et al. |
| 2019/0142520 A1 | 5/2019 | Vandyken |
| 2019/0159841 A1 | 5/2019 | Abhari et al. |
| 2019/0167148 A1 | 6/2019 | Durfee et al. |
| 2019/0175058 A1 | 6/2019 | Godwin et al. |
| 2019/0180441 A1 | 6/2019 | Peng et al. |
| 2019/0183576 A1 | 6/2019 | Fahim et al. |
| 2019/0183590 A1 | 6/2019 | Hladio et al. |
| 2019/0192230 A1 | 6/2019 | Siemionow et al. |
| 2019/0192232 A1 | 6/2019 | Altmann et al. |
| 2019/0200844 A1 | 7/2019 | Shelton, IV et al. |
| 2019/0200977 A1 | 7/2019 | Shelton, IV et al. |
| 2019/0201104 A1 | 7/2019 | Shelton, IV et al. |
| 2019/0201106 A1 | 7/2019 | Siemionow et al. |
| 2019/0201158 A1 | 7/2019 | Shelton, IV et al. |
| 2019/0206062 A1 | 7/2019 | Matsuoka et al. |
| 2019/0206134 A1 | 7/2019 | Devam et al. |
| 2019/0206565 A1 | 7/2019 | Shelton, IV |
| 2019/0209241 A1 | 7/2019 | Begg |
| 2019/0214126 A1 | 7/2019 | Goetz |
| 2019/0216572 A1 | 7/2019 | Wang et al. |
| 2019/0223746 A1 | 7/2019 | Intrator |
| 2019/0231220 A1 | 8/2019 | Refai et al. |
| 2019/0231443 A1 | 8/2019 | McGinley et al. |
| 2019/0239850 A1 | 8/2019 | Dalvin et al. |
| 2019/0254753 A1 | 8/2019 | Johnson et al. |
| 2019/0274762 A1 | 9/2019 | Kim et al. |
| 2019/0282099 A1 | 9/2019 | Themelis |
| 2019/0307516 A1 | 10/2019 | Schotzko et al. |

\* cited by examiner

AUGMENTED REALITY NAVIGATION SYSTEMS FOR USE WITH ROBOTIC SURGICAL SYSTEMS AND METHODS OF THEIR USE

CROSS REFERENCE TO RELATED APPLICATIONS

This patent application is a continuation of U.S. patent application Ser. No. 15/899,038 filed on Feb. 19, 2018, which is incorporated in its entirety herein.

FIELD

The present invention relates generally to augmented reality systems for use with robotic surgical systems and methods of their use.

BACKGROUND

Robotic surgical systems are used in many surgical procedures in order to assist surgeons in precisely and accurately performing the procedures. Frequently, these procedures require precise placement of one or more implants and can be performed using minimally invasive techniques. Robotic surgical systems follow pre-planned or intra-operatively planned trajectories that assist the surgeon in placing implants while maintaining their intended alignment. Navigation markers placed throughout the surgical environment are used to register the environment (e.g., patient anatomy) with the robotic surgical system in order to properly orient the robot to the pre-planned or intra-operatively planned trajectories. Additionally, medical image data can be registered to the robotic surgical system to provide a model of the patient's anatomy for use in navigation.

Surgeons plan and monitor trajectories as well as monitor status of a robotic surgical system and a patient's anatomy during a procedure using a fixed display, for example, attached to or next to the robotic surgical system. Such a fixed display is the primary mechanism for navigating and monitoring a robotic surgical system during a procedure. This is especially true for minimally invasive procedures where a patient's anatomy obstructs direct view of the surgical site. However, fixed displays require a surgeon to divert his or her vision away from the surgical site and/or surgical tools that he or she is manipulating in order to obtain navigational information displayed on the screen. Moreover, the display screen can physically obstruct a surgeon's view of a portion of the surgical environment.

SUMMARY

There is a need for systems and methods for viewing navigational information from a robotic surgical system that reduce a surgeon's need to divert his or her vision while not obstructing view of the surgical environment. The present disclosure is directed to augmented reality navigation systems and methods of their use that, inter alia, address the need for systems and methods of robotic surgical system navigation with reduced distraction to surgeons. Augmented reality navigation systems disclosed herein enable a surgeon to maintain focus on a surgical site and/or surgical tool being used in a surgical procedure while obtaining a wide range of navigational information relevant to the procedure. Navigational information includes, but is not limited to, a model of a patient's anatomy derived from medical image data, a trajectory or position of a surgical tool or robotic surgical system, or a position and orientation of a surgical implant. Navigational information can be sent to an augmented reality navigation system as navigation input data from a robotic surgical system. Navigational information can appear in the augmented reality navigation system as being presented on virtual displays that sit in a natural field of view of a surgeon during a procedure. Navigational information can also appear to be overlaid over a patient's anatomy. Navigational information can include information otherwise not visible in a surgeon's natural field of view, for example trajectories and or portions of a surgical tool obscured by a patient's anatomy.

Augmented reality navigation systems comprise a head mounted display comprising an at least partially transparent display screen, at least one detector connected to the head mounted display for identifying real-world features, and a computer subsystem. The display screen displays augmentation graphics, for example navigation augmentation graphics that provide navigational information to a surgeon. The navigation augmentation graphics can appear as a separate display in the field of view of a surgeon or overlaid over a patient's anatomy. The at least one detector identifies real-world features, wherein the real-world features can be, for example fiducials and/or patient anatomy recognized via image recognition methods. In this way, the at least one detector mounted to the head mounted display acts as the detector in a typical navigation system used during surgery (e.g., can be used to register a patient's anatomy and a robotic surgical system) without requiring an additional piece of equipment in the surgical environment. The computer subsystem can be configured to perform a variety of navigational tasks useful to a surgeon during a procedure including, for example, trajectory planning and execution. A motion sensor can optionally be included to detect motion of the head of a surgeon wearing the augmented reality navigation system providing additional functionality and/or performance (e.g., a selection input means or drift correction).

In certain embodiments, an augmented reality navigation system eliminates the need for an auxiliary navigation subsystem such as those commonly used with current robotic surgical systems. The at least one detector in the augmented reality navigation system detects real-world features (e.g., fiducials) in sufficiently quantity and resolution as to properly register a patient to a robotic surgical system and, optionally, one or more models of patient anatomy derived from medical image data. Therefore, the augmented reality navigation system acts as a standalone system without the need for additional equipment. Although, in certain embodiments, an auxiliary detector is used in conjunction with the augmented reality navigation system. An auxiliary detector may provide a larger registered field, improved resolution of registration, and/or redundancy.

In one aspect, the invention is directed to an augmented reality navigation system for use with a robotic surgical system, the system comprising: a head mounted display comprising an at least partially transparent display screen configured to display augmentation graphics (e.g., semi-opaque images) (e.g., navigation augmentation graphics) which appear to a user to be superimposed on at least a portion of a natural field of view of the user; at least one detector for identifying real-world features, the at least one detector connected to the head mounted display [e.g., wherein the at least one detector comprises at least one of an optical camera (e.g., a video camera), an EMF detector, a LiDAR detector, an acoustic detector, and an RF detector] [e.g., wherein the real-world features comprises fiducials and/or identified patient anatomy (e.g., wherein the real-world features are fiducials connected to at least one of a patient, a surgical tool, and the robotic surgical system (e.g., a robotic arm, a part of a robotic arm, and/or an end-effector of a robotic arm))]; a processor of a computing device; and a non-transitory computer readable medium having instructions stored thereon, wherein the instructions, when executed by the processor, cause the processor to: receive, by the processor, a detector input signal from the at least one detector, wherein the detector input signal corresponds to a field of view of the at least one detector and the field of view comprises at least a portion of anatomy of a patient during a surgical procedure, determine, by the processor, a relative location and/or orientation for each of one or more the real-world features in the detector input signal, generate and/or access, by the processor, a representation of at least a portion of a surgical tool and/or a trajectory of the surgical tool, wherein the surgical tool is inserted into or connected to the robotic surgical system (e.g., wherein the portion of the surgical tool is hidden from the natural field of view of the user, e.g., within a patient), modify (e.g., least one of rotate, scale, and translate), by the processor, at least a portion of the representation based on the relative location and/or orientation of the one or more real-world features, thereby forming an updated representation, render, by the processor, surgical tool augmentation graphics based on the updated representation, and display, by the processor, the surgical tool augmentation graphics on the display screen (e.g., display, via the at least partially transparent display screen of the head mounted display, the surgical tool augmentation graphics superimposed on at least a portion of the natural field of view of the user).

In some embodiments, the instructions cause the processor to: render, by the processor, a surgical tool augmentation graphic for each of a plurality of surgical tool trajectories (e.g., planned surgical tool trajectories); and display, by the processor, on the display screen, the plurality of surgical tool augmentation graphics such that the surgical tool augmentation graphics appear overlaid on the anatomy of the patient and each of the trajectory augmentation graphics indicate a physical trajectory that could be followed during the surgical procedure.

In some embodiments, the instructions cause the processor to: determine, by the processor, a relative location and/or orientation for each of at least one real-world feature from the detected input signal; modify, by the processor, (e.g., by at least one of rotation, scaling, and translation) an anatomical model of a patient (e.g., a 3D model) based on the relative locations and/or orientations determined from the detected input signal, thereby forming an updated anatomical model (e.g., that is registered to the anatomy of the patient); render, by the processor, anatomical model augmentation graphics based at least in part on the updated anatomical model; and display, by the processor, on the display screen, the anatomical model augmentation graphics such that the updated anatomical model appears overlaid on the anatomy of the patient.

In some embodiments, the augmented reality navigation system comprises a motion sensor (e.g., an inertial motion unit (IMU)) connected to the head mounted display for outputting a motion signal based on measured motion of the head mounted display and wherein the instructions cause the processor to: update, by the processor, the relative position and orientation of the determined real-world features in the detector input signal based on motion detected by the motion sensor; and update, by the processor, the surgical tool augmentation graphics based on the updated relative position and orientation.

In some embodiments, the instructions cause the processor to: receive, by the processor, a user input trajectory selection signal that selects a trajectory from a set of one or more planned trajectories (e.g., one or more preoperatively or intraoperatively planned trajectories) (e.g., wherein the user input trajectory selection signal corresponds to a gesture or sound made by the user or a position and/or orientation of a robotic arm and/or end effector of the robotic surgical system); determine, by the processor, a selected trajectory based at least in part on the user input trajectory selection signal; and automatically move, by the processor, a robotic arm and/or end effector of the robotic surgical system to be aligned with the selected trajectory.

In some embodiments, the instructions cause the processor to: automatically move, by the processor, the robotic arm and/or end effector of the robotic surgical system along the selected trajectory (e.g., towards the anatomy of the patient).

In some embodiments, the instructions cause the processor to: define and/or update, by the processor, a haptic object that comprises the selected trajectory; and constrain, by the processor, motion of a robotic arm and/or end effector such that motion of at least a portion of the surgical tool inserted into or attached to the robotic arm and/or end effector is constrained to within the haptic object.

In some embodiments, the at least one detector comprises a detector with at least a minimum field of view of 40 degrees (e.g., as measured on a diagonal). In some embodiments, the display screen has a resolution of at least 1280× 720 pixels.

In some embodiments, the augmented reality navigation system comprises a pointer tool for making surgical planning selections (e.g., of a trajectory and/or position(s) and/or orientation(s) that define a trajectory), wherein the pointer tool is configured to be detected by the at least one detector.

In some embodiments, the instructions cause the processor to register anatomy of a patient with the robotic surgical system, the augmented reality navigation system, and, optionally, an anatomical model of the patient based on medical image data (e.g., X-ray data, CT data, MM data, fluoroscopy data).

In some embodiments, the at least one detector comprises a video camera and the instructions cause the processor to: generate, by the processor, a video signal based on the detector input signal; and output, by the processor, the video signal for display on at least one of (i) a monitor and (ii) a second head mounted display comprising an at least partially transparent display screen configured to display augmentation graphics (e.g., semi-opaque images) which appear to a user to be superimposed on at least a portion of a natural field of view of the user.

In some embodiments, the system comprises one or more fiducial markers connected to the head mounted display. In some embodiments, the instructions cause the processor to: receive, by the processor, a relative location and orientation of the one or more fiducial markers connected to the head mounted display, wherein the one or more fiducial markers are detected by a secondary detector (e.g., not physically connected to the head mounted display) (e.g., an EMF detector, an RF detector, an acoustic detector, a LiDAR detector, an optical detector); and modify (e.g., at least one of rotate, scale, and translate) at least one of (i) an anatomical model, (ii) a representation of a surgical implant, (iii) a representation of a trajectory of a surgical tool, and (iv) a representation of at least a portion of a surgical tool hidden from a natural field of view based on the one or more fiducial markers detected by the secondary detector.

In some embodiments, the instructions cause the processor to: receive, by the processor, a relative location and orientation of one or more real-world features detected by a secondary detector (e.g., not physically connected to the head mounted display) (e.g., an EMF detector, an RF detector, an acoustic detector, a LiDAR detector, an optical detector); modify (e.g., at least one of rotate, scale, and translate), by the processor, at least one of (i) an anatomical model, (ii) a representation of a surgical implant, (iii) a representation of a trajectory of a surgical tool, and (iv) a representation of at least a portion of a surgical tool hidden from a natural field of view based on the one or more real-world features detected by the secondary detector; render and/or update, by the processor, updated augmentation graphics based at least in part on the modified at least one of (i), (ii), (iii), and (iv); an display, by the processor, on the display screen, the updated augmentation graphics.

In some embodiments, the surgical procedure comprises at least one of a spinal surgical procedure, an orthopedic surgical procedure, an orthopedic trauma surgical procedure, and a neurosurgical procedure. In some embodiments, the surgical procedure comprises a minimally invasive surgical procedure.

In one aspect, the invention is directed to an augmented reality navigation system for use with a robotic surgical system, the system comprising: a head mounted display comprising an at least partially transparent display screen configured to display augmentation graphics (e.g., semi-opaque images) (e.g., navigation augmentation graphics) which appear to a user to be superimposed on at least a portion of a natural field of view of the user; at least one detector for identifying real-world features, the at least one detector connected to the head mounted display [e.g., wherein the at least one detector comprises at least one of an optical camera (e.g., a video camera), an EMF detector, a LiDAR detector, an acoustic detector, and an RF detector] [e.g., wherein the real-world features comprises fiducials and/or identified patient anatomy (e.g., wherein the real-world features are fiducials connected to at least one of a patient, a surgical tool, and the robotic surgical system (e.g., a robotic arm, a part of a robotic arm, and/or an end-effector of a robotic arm))]; and a computer subsystem configured to generate and/or access a representation of at least a portion of a surgical tool and/or a trajectory of the surgical tool during a surgical procedure, modify at least a portion of the representation based on a relative position and/or orientation of one or more real-world features in a detector input signal received from the at least one detector, and display, on the display screen, surgical tool augmentation graphics based on the modified representation, wherein the surgical tool is inserted into or connected to the robotic surgical system (e.g., wherein the portion of the surgical tool is hidden from the natural field of view of the user, e.g., within a patient).

In some embodiments, the computer subsystem is configured to render a surgical tool augmentation graphic for each of a plurality of surgical tool trajectories (e.g., planned surgical tool trajectories), and display, on the display screen, the plurality of surgical tool augmentation graphics such that the surgical tool augmentation graphics appear overlaid on the anatomy of the patient and each of the trajectory augmentation graphics indicate a physical trajectory that could be followed during the surgical procedure.

In some embodiments, the computer subsystem is configured to modify (e.g., by at least one of rotation, scaling, and translation) an anatomical model of a patient (e.g., a 3D model) based on one or more relative location(s) and/or orientation(s) determined from the detected input signal, thereby forming an updated anatomical model (e.g., that is registered to the anatomy of the patient), and the computer subsystem is configured to display, on the display screen, anatomical model augmentation graphics corresponding to the updated anatomical model such that the updated anatomical model appears overlaid on the anatomy of the patient.

In some embodiments, the augmented reality navigation system comprises a motion sensor (e.g., an inertial motion unit (IMU)) connected to the head mounted display for outputting a motion signal based on measured motion of the head mounted display, wherein the computer subsystem is configured to update the surgical tool augmentation graphics based on motion detected by the motion sensor.

In some embodiments, the computer subsystem is configured to determine a selected trajectory based at least in part on a user input trajectory selection signal that selects the selected trajectory from a set of one or more planned trajectories (e.g., one or more preoperatively or intraoperatively planned trajectories) (e.g., wherein the user input trajectory selection signal corresponds to a gesture or sound made by the user or a position and/or orientation of a robotic arm and/or end effector of the robotic surgical system), and automatically move a robotic arm and/or end effector of the robotic surgical system to be aligned with the selected trajectory.

In some embodiments, the computer subsystem is configured to automatically move the robotic arm and/or end effector of the robotic surgical system along the trajectory (e.g., towards the anatomy of the patient).

In some embodiments, the computer subsystem is configured to define a haptic object that comprises the trajectory and constrain motion of a robotic arm and/or end effector such that motion of at least a portion of a surgical tool attached to the robotic arm and/or end effector is constrained to within the haptic object.

In some embodiments, the at least one detector comprises a detector with at least a minimum field of view of 40 degrees (e.g., as measured on a diagonal). In some embodiments, the display screen has a resolution of at least 1280× 720 pixels. In some embodiments, the augmented reality navigation system comprises a pointer tool for making surgical planning selections, wherein the pointer tool is configured to be detected by the at least one detector.

In some embodiments, the computer subsystem is configured to register anatomy of a patient with the robotic surgical system, the augmented reality navigation system, and, optionally, an anatomical model of the patient based on medical image data (e.g., X-ray data, CT data, MM data, fluoroscopy data).

In some embodiments, the computer subsystem is configured to generate a video signal based on the detector input signal and output the video signal for display on at least one of (i) a monitor and (ii) a second head mounted display comprising an at least partially transparent display screen configured to display augmentation graphics (e.g., semi-opaque images) which appear to a user to be superimposed on at least a portion of a natural field of view of the user.

In some embodiments, the system comprises one or more fiducial markers connected to the head mounted display. In some embodiments, the computer subsystem is configured to receive a relative location and orientation of the one or more fiducial markers connected to the head mounted display detected by a secondary detector (e.g., not physically connected to the head mounted display) (e.g., an EMF detector, an RF detector, an acoustic detector, a LiDAR detector, an optical detector) and modify (e.g., at least one of rotate, scale, and translate) at least one of (i) an anatomical model, (ii) a representation of a surgical implant, (iii) a representation of a trajectory of a surgical tool, and (iv) a representation of at least a portion of a surgical tool hidden from a natural field of view based on the one or more fiducial markers detected by the secondary detector.

In some embodiments, the computer subsystem is configured to receive a relative location and orientation of one or more real-world features detected by a secondary detector (e.g., not physically connected to the head mounted display) (e.g., an EMF detector, an RF detector, an acoustic detector, a LiDAR detector, an optical detector) and modify (e.g., at least one of rotate, scale, and translate) at least one of (i) an anatomical model, (ii) a representation of a surgical implant, (iii) a representation of the trajectory, and (iv) a representation of at least a portion of a surgical tool hidden from a natural field of view based on the one or more real-world features detected by the secondary detector, and the computer subsystem is configured to display, on the display screen, updated augmentation graphics based at least in part on the modified at least one of (i), (ii), (iii), and (iv).

In some embodiments, the surgical procedure comprises at least one of a spinal surgical procedure, an orthopedic surgical procedure, an orthopedic trauma surgical procedure, and a neurosurgical procedure. In some embodiments, the surgical procedure comprises a minimally invasive surgical procedure.

In one aspect, the invention is directed to a method of using an augmented reality navigation system with a robotic surgical system, the method comprising: providing and/or accessing the augmented reality navigation system, wherein the augmented reality navigation system comprises: a head mounted display comprising an at least partially transparent display screen configured to display augmentation graphics (e.g., semi-opaque images) (e.g., navigation augmentation graphics) which appear to a user to be superimposed on at least a portion of a natural field of view of the user; optionally, a motion sensor (e.g., an inertial motion unit (IMU)) connected to the head mounted display for outputting a motion signal based on measured motion of the head mounted display; and at least one detector for identifying real-world features, the at least one detector connected to the head mounted display [e.g., wherein the at least one detector comprises at least one of an optical camera (e.g., a video camera), an EMF detector, a LiDAR detector, an acoustic detector, and an RF detector] [e.g., wherein the real-world features comprises fiducials and/or identified patient anatomy (e.g., wherein the real-world features are fiducials connected to at least one of a patient, a surgical tool, and the robotic surgical system (e.g., a robotic arm, a part of a robotic arm, and/or an end-effector of a robotic arm))]; receiving (e.g., by a processor of a computer subsystem) a detector input signal from the at least one detector, wherein the detector input signal corresponds to a field of view of the at least one detector and the field of view comprises at least a portion of anatomy of a patient during a surgical procedure, determining (e.g., by a processor of a computer subsystem) a relative location and/or orientation for each of one or more the real-world features in the detector input signal, generating and/or accessing (e.g., by a processor of a computer subsystem) a representation of at least a portion of a surgical tool and/or a trajectory of the surgical tool, wherein the surgical tool is inserted into or connected to the robotic surgical system (e.g., wherein the portion of the surgical tool is hidden from the natural field of view of the user, e.g., within a patient), modifying (e.g., least one of rotating, scaling, and translating) (e.g., by a processor of a computer subsystem) at least a portion of the representation based on the relative location and orientation of the one or more real-world features, thereby forming an updated representation, rendering (e.g., by a processor of a computer subsystem) surgical tool augmentation graphics based on the updated representation, and displaying (e.g., by a processor of a computer subsystem) the surgical tool augmentation graphics on the display screen (e.g., displaying, via the at least partially transparent display screen of the head mounted display, the surgical tool augmentation graphics superimposed on at least a portion of the natural field of view of the user).

In some embodiments, the method comprises: rendering (e.g., by a processor of a computer subsystem) a surgical tool augmentation graphic for each of a plurality of surgical tool trajectories (e.g., planned surgical tool trajectories); and displaying (e.g., by a processor of a computer subsystem) on the display screen, the plurality of surgical tool augmentation graphics such that the surgical tool augmentation graphics appear overlaid on the anatomy of the patient and each of the trajectory augmentation graphics indicate a physical trajectory that could be followed during the surgical procedure.

In some embodiments, the method comprises: determining (e.g., by a processor of a computer subsystem) a relative location and/or orientation for each of at least one real-world feature from the detected input signal; modifying (e.g., by at least one of rotating, scaling, and translating) (e.g., by a processor of a computer subsystem) an anatomical model of a patient (e.g., a 3D model) based on the relative locations and/or orientations determined from the detected input signal, thereby forming an updated anatomical model (e.g., that is registered to the anatomy of the patient); rendering (e.g., by a processor of a computer subsystem) anatomical model augmentation graphics based at least in part on the updated anatomical model; and displaying, on the display screen, (e.g., by a processor of a computer subsystem) the anatomical model augmentation graphics such that the updated anatomical model appears overlaid on the anatomy of the patient.

In some embodiments, the method comprises: updating (e.g., by a processor of a computer subsystem) the relative position and orientation of the determined real-world features in the detector input signal based on motion detected by the motion sensor; and updating (e.g., by a processor of a computer subsystem) the surgical tool augmentation graphics based on the updated relative position and orientation.

In some embodiments, the method comprises: receiving (e.g., by a processor of a computer subsystem) a user input trajectory selection signal that selects a trajectory from a set of one or more planned trajectories (e.g., one or more preoperatively or intraoperatively planned trajectories) (e.g., wherein the user input trajectory selection signal corresponds to a gesture or sound made by the user or a position and/or orientation of a robotic arm and/or end effector of the robotic surgical system); determining (e.g., by a processor of a computer subsystem) a selected trajectory based at least in part on the user input trajectory selection signal; and automatically (e.g., by a processor of a computer subsystem) moving a robotic arm and/or end effector of the robotic surgical system to be aligned with the selected trajectory.

In some embodiments, the method comprises: automatically (e.g., by a processor of a computer subsystem) moving the robotic arm and/or end effector of the robotic surgical system along the selected trajectory (e.g., towards the anatomy of the patient). In some embodiments, the method comprises: defining and/or updating (e.g., by a processor of a computer subsystem) a haptic object that comprises the selected trajectory; and constraining motion of a robotic arm and/or end effector such that motion of at least a portion of the surgical tool inserted into or attached to the robotic arm and/or end effector is constrained to within the haptic object.

In some embodiments, the at least one detector comprises a detector with at least a minimum field of view of 40 degrees (e.g., as measured on a diagonal). In some embodiments, the display screen has a resolution of at least 1280× 720 pixels.

In some embodiments, the method comprises: registering anatomy of a patient with the robotic surgical system, the augmented reality navigation system, and, optionally, an anatomical model of the patient based on medical image data (e.g., X-ray data, CT data, MM data, fluoroscopy data).

In some embodiments, the at least one detector comprises a video camera and the method comprises: generating (e.g., by a processor of a computer subsystem) a video signal based on the detector input signal; and outputting (e.g., by a processor of a computer subsystem) the video signal for display on at least one of (i) a monitor and (ii) a second head mounted display comprising an at least partially transparent display screen configured to display augmentation graphics (e.g., semi-opaque images) which appear to a user to be superimposed on at least a portion of a natural field of view of the user.

In some embodiments, the system comprises one or more fiducial markers connected to the head mounted display and the method comprises: receiving (e.g., by a processor of a computer subsystem) a relative location and orientation of the one or more fiducial markers connected to the head mounted display, wherein the one or more fiducial markers are detected by a secondary detector (e.g., not physically connected to the head mounted display) (e.g., an EMF detector, an RF detector, an acoustic detector, a LiDAR detector, an optical detector); and modifying (e.g., at least one of rotating, scaling, and translating) (e.g., by a processor of a computer subsystem) at least one of (i) an anatomical model, (ii) a representation of a surgical implant, (iii) a representation of a trajectory of a surgical tool, and (iv) a representation of at least a portion of a surgical tool hidden from a natural field of view based on the one or more fiducial markers detected by the secondary detector.

In some embodiments, the method comprises: receiving (e.g., by a processor of a computer subsystem) a relative location and orientation of one or more real-world features detected by a secondary detector (e.g., not physically connected to the head mounted display) (e.g., an EMF detector, an RF detector, an acoustic detector, a LiDAR detector, an optical detector); modifying (e.g., at least one of rotating, scaling, and translating) (e.g., by a processor of a computer subsystem) at least one of (i) an anatomical model, (ii) a representation of a surgical implant, (iii) a representation of a trajectory of a surgical tool, and (iv) a representation of at least a portion of a surgical tool hidden from a natural field of view based on the one or more real-world features detected by the secondary detector; rendering and/or updating (e.g., by a processor of a computer subsystem) updated augmentation graphics based at least in part on the modified at least one of (i), (ii), (iii), and (iv); and displaying (e.g., by a processor of a computer subsystem) on the display screen, the updated augmentation graphics.

In some embodiments, the surgical procedure comprises at least one of a spinal surgical procedure, an orthopedic surgical procedure, an orthopedic trauma surgical procedure, and a neurosurgical procedure. In some embodiments, the surgical procedure comprises a minimally invasive surgical procedure.

DEFINITIONS

In order for the present disclosure to be more readily understood, certain terms used herein are defined below. Additional definitions for the following terms and other terms may be set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The following description generally makes use of a Cartesian coordinate system in describing positions, orientations, and directions of travel of various elements of and relating to the systems and methods described herein. However, it should be understood that specific coordinates (e.g., "x, y, z") and related conventions based on them (e.g., a "positive x-direction", an "x, y, or z-axis", an "xy, xz, or yz-plane", and the like) are presented for convenience and clarity, and that, as understood by one of skill in the art, other coordinate systems could be used (e.g., cylindrical, spherical) and are considered to be within the scope of the claims.

Navigational information: As used herein, the term "navigational information" means information useful in navigating during a surgical procedure. In certain embodiments, navigating includes navigating one or more surgical tools and/or implants (or other surgical apparatus). The surgical tool(s) may be attached to a robotic surgical system. Navigational information includes, but is not limited to, one or more of surgical trajectories, positions and/or orientations of (i) surgical tools and/or apparatus (e.g., implants) and/or surgical equipment (e.g., surgical tables), patient anatomy and/or models thereof, medical image data, and positions and/or orientations of a robotic surgical system. As used herein, where an augmented reality navigation system is described as displaying navigational information to a surgeon, it is understood that other information not immediately relevant to navigation, but relevant generally to a surgical procedure may also be displayed (e.g., in a similar fashion). For example, patient health information regarding a patient's vitals or condition (e.g., patient history) or status information related to a surgical procedure (e.g., progress, instructions, or other information) may be displayed (e.g., on a virtual display presented on a display screen of an augmented reality navigation system). When appropriate, navigational information can optionally appear overlaid over a patient's anatomy.

Augmentation graphic: As used herein, the term "augmentation graphic" refers to a graphic that is rendered by a processor and displayed on a display screen of an augmented reality navigation system such that the graphic appears superimposed on the natural field of view of a surgeon as viewed through the display screen. In certain embodiments, an augmentation graphic may also be rendered for display on a remote monitor to allow third party observers to observe what a surgeon is seeing (e.g., one that is mounted on a wall of an operating room). An augmentation graphic may be a standalone graphic that appears in the natural field of view (e.g., as a virtual display floating in the field of view of a surgeon). An augmentation graphic may appear overlaid over one or more objects (e.g., patient anatomy) in the natural field of view, such that the augmentation graphic coincides with a physical object (e.g., portion of a patient anatomy) that is represented by the augmentation graphic (e.g., wherein the physical object or a portion thereof is not otherwise seen by a surgeon). In certain embodiments, an augmentation graphic may appear as a 3D object that sits adjacent to the physical object that it represents (e.g., with a common orientation but offset by a spatial translation). In some embodiments, augmentation graphics comprise several graphics for display in a chronological order such that they appear as a video on a display screen that augments a surgeon's natural field of view. For example, a surgeon can view a portion of a procedure as it will occur overlaid over a patient's physical anatomy.

Medical image data: As used herein, medical image data refers to image data that represents at least a portion of a patient. Medical image data may be generated using any suitable technique including, but not limited to, X-ray techniques, radiography techniques (fluoroscopy techniques (e.g., generated using an O-arm or C-arm)), tomographic techniques (e.g., X-ray computed tomography, positron emission tomography (PET), or magnetic resonance imaging (MRI)), ultrasound techniques, or elastography techniques.

Pointer tool: As used herein, the term "pointer tool" refers to a tool that is used to indicate a desired position and/or orientation. A pointer tool may be configured to be inserted into a robotic surgical system, for example, an end effector thereof or a tool guide attached thereto. A pointer tool may be a specially configured instrument solely used for pointing. A surgical tool may be used as a pointer tool. For example, a drill bit, a drill guide, a tool guide, an awl, or similar surgical tool may be used as a pointer tool. A pointer tool may have one or more fiducials attached to the tool (e.g., sufficient to determine a position and orientation of the pointer tool (e.g., by triangulation)).

Real-world feature: As used herein, the term "real-world feature" refers to a physical object or portion thereof that can be detected by a detector such that spatial information about the object can be determined. Spatial information comprises a position and/or orientation. A real-world feature may be identified patient anatomy (e.g., identified by reference to an anatomy database (e.g., a database of images of patient anatomy)) that is detected using one or more image-recognition techniques. A real-world feature may be any suitable fiducial. A fiducial may be attached to, for example, surgical equipment (e.g., an operating table), a patient, a surgical tool, an implant, a robotic surgical system, or an augmented reality navigation system (e.g., on the head mounted display). A fiducial may comprise a plurality of markers to assist in orienting the fiducial in the environment during navigation (e.g., tracking). For example, in certain embodiments, a fiducial comprises a plurality of spatially separated markers (e.g., 3 markers or 4 markers) attached to a rigid holding apparatus that is attachable to an object, wherein each of the markers is configured to be detected by a detector disposed on the head mounted display (e.g., emit or alter an electromagnetic field for an EMF detector or have a certain reflectivity for an optical detector). Real-world features are used to determine position and orientation of objects in a surgical environment. An example of a technique used to make such a determination using the systems disclosed herein is triangulation, however, it will be apparent to those of ordinary skill in the art of patient registration that any of a number of techniques may be used, alone or in combination, such as surface matching or other similar correlation techniques.

Trajectory: As used herein, the term "trajectory" refers to a path desired and/or intended to be followed. A trajectory may be modeled and graphics representing the trajectory may be displayed on a display screen of an augmented reality navigation system. A trajectory may a linear trajectory (e.g., wherein all points along the trajectory fall onto a line) or a non-linear trajectory. A trajectory sent by a processor (e.g., to a robotic surgical system) or stored on a computer readable medium (e.g., for manipulation by a processor) may be represented by any data sufficient to define the trajectory. Non-limiting examples of data used to define a trajectory include a single coordinate in space and an orientation (e.g., vector), a plurality of coordinates, and a functional relationship (e.g., involving an x, y, and z variable). In certain embodiments, a path may be followed using a robotic surgical system (e.g., automatically) or manually by a surgeon.

Robotic surgical system: As used herein, the term "robotic surgical system" refers to a system comprising a robotic arm configured to assist in a surgical procedure. A robotic arm may assist in a surgical procedure by holding and/or manipulating (e.g., guiding and/or moving) one or more surgical tool(s). In certain embodiments, a robotic surgical system comprises an active, non-backdriveable robotic arm. In certain embodiments, a robotic surgical system comprises a passive, backdriveable robotic arm. In certain embodiments, a robotic surgical system is configured to be manipulated directly by a surgeon (e.g., by grasping and maneuvering). In certain embodiments, a robot is configured to be manipulated remotely by a surgeon (e.g., similarly to a master/slave system). In certain embodiments, a robotic arm of a robotic surgical system is configured to assist in a surgical procedure by preventing a surgeon from actively maneuvering a surgical tool attached to the robotic arm outside of a defined haptic object (i.e., haptic volume). In certain embodiments, a robotic arm of a robotic surgical system is configured to automatically move, upon input from a surgeon, onto and/or along a trajectory, such as a trajectory pre-operatively or intra-operatively planned using an augmented reality navigation system in communication with the robotic surgical system. In certain embodiments, a robotic surgical system and an augmented reality navigation system have a common computer subsystem.

BRIEF DESCRIPTION OF THE DRAWING

Drawings are presented herein for illustration purposes, not for limitation. The foregoing and other objects, aspects, features, and advantages of the invention will become more apparent and may be better understood by referring to the following description taken in conjunction with the accompanying drawings, in which.

DETAILED DESCRIPTION

Figure 1:
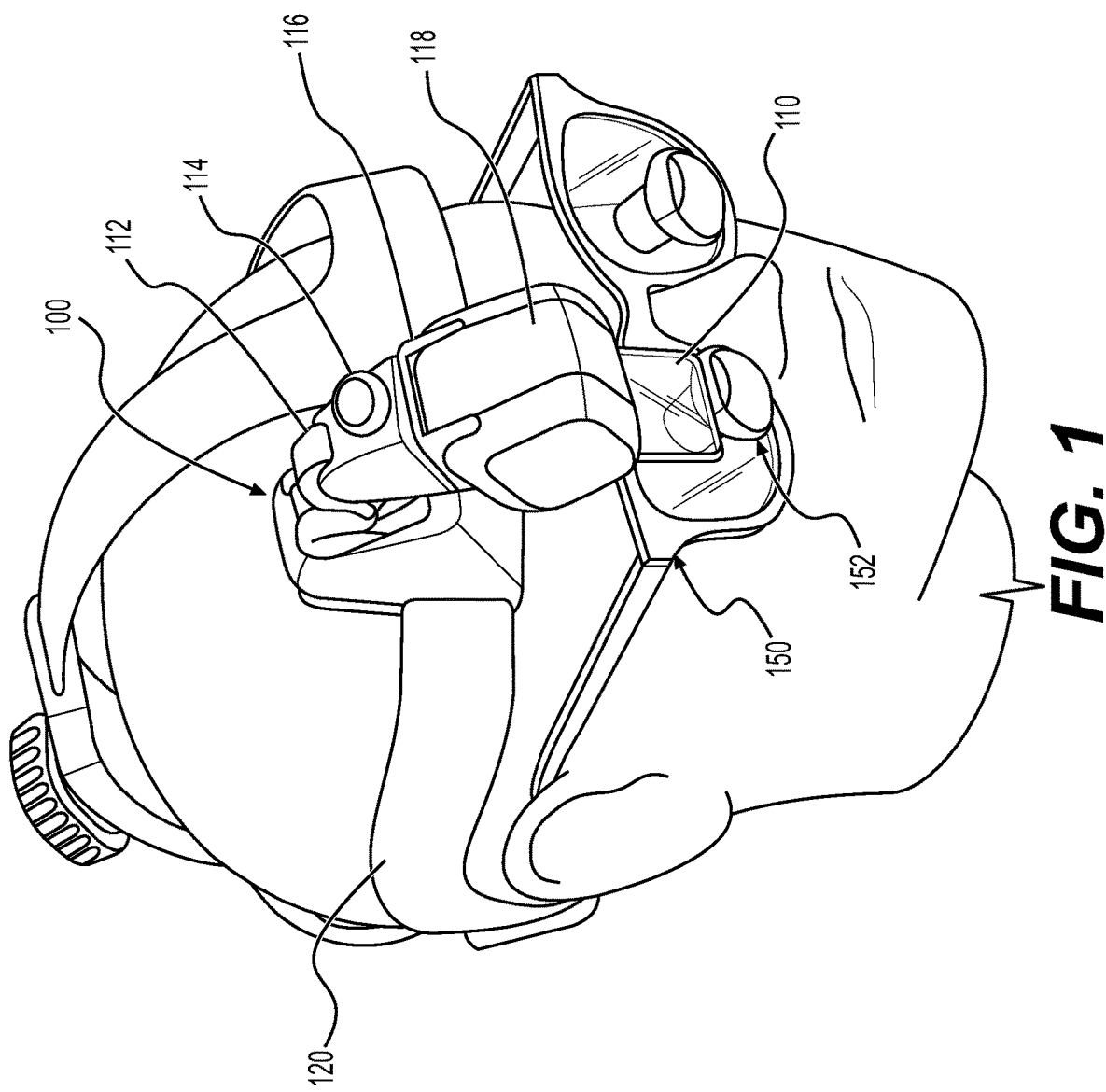
FIG. 1 illustrates a head mounted display apparatus that can be worn on a user's head and operates in accordance with some embodiments of the invention.

It is contemplated that systems, devices, methods, and processes of the claimed invention encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim. Headers are provided for the convenience of the reader and are not intended to be limiting with respect to the claimed subject matter.

Augmented Reality Navigation Systems and Components Thereof

The augmented reality navigation systems disclosed herein comprise a head mounted display comprising an at least partially transparent display screen, at least one detector connected to (e.g., disposed on) the head mounted display for identifying real-world features, and a computer subsystem. The computer subsystem can be configured to perform a variety of navigational tasks useful to a surgeon during a procedure including, for example, trajectory planning and execution. A motion sensor can optionally be included to detect motion of the head of a surgeon wearing the augmented reality navigation system providing additional functionality and/or performance (e.g., a selection input means or drift correction). Augmented reality navigation systems for use in certain surgical procedures that are in accordance with certain embodiments of the present disclosure are described in U.S. Patent Publication No. 2016-0225192 A1, published on Aug. 4, 2016, the disclosure of which is hereby incorporated by reference herein in its entirety.

Embodiments of the present disclosure are directed to an augmented reality surgical system that includes a head mounted display (HMD) apparatus that can be worn by a surgeon, physician, or other personnel during a medical procedure. Throughout the present disclosure, where an augmented reality navigation system is described as being worn by or used by a wearer, user, or surgeon, it is understood that any person assisting with, leading, or observing a surgical procedure can equivalently interact with an augmented reality navigation system in the same manner as is being described. The user is not limited to any one particular individual with a specific relationship to a surgical procedure. The HMD can be configured to provide localized, real-time situational awareness to the wearer. The HMD includes a display screen that can be positioned within the natural line-of-sight and/or periphery field of view (FOV) of the wearer to provide visual information that can be organized and displayed as a single virtual display or as a collection of virtual displays that a wearer can navigate between to view using head movement, hand gestures, voice commands, eye control, and/or other operations disclosed herein. In certain embodiments, a display screen can be manipulated to be in or out of a natural field of view of a surgeon (e.g., by flipping the screen from an "in use" to "out of use" position").

In certain embodiments, a surgeon or other person can wear an HMD to see a graphical representation of what is within the patient's body but covered from view by skin, muscle, organs, skeletal structure, etc. In certain embodiments, using an HMD can enable a surgeon to minimize the size of an incision by observing where the incision needs to be made to reveal a targeted portion of the body. Similarly, an HMD can be used when replacing a bone with prosthesis to enable a surgeon to observe a real-world feature that aids with orienting and moving surgical tool(s) (e.g., attached to a robotic surgical system) and/or a prosthesis during the procedure. An HMD may operate to improve the efficiency, productivity, throughput, and/or accuracy, and/or safety of the wearer's performance of a medical procedure. Moreover, an HMD can reduce mental fatigue by reducing or eliminating a need for the wearer to reference remote display devices having substantial angular offsets during a medical procedure.

In certain embodiments, an augmented reality navigation system has an initialization time of under 10 minutes (e.g., under 5 minutes) thereby minimizing delay and interference of surgical procedures. In certain embodiments, an augmented reality navigation system can be comfortably word for a minimum of one hour and up to four hours or more. In certain embodiments, an augmented reality navigation system is compatible with surgeon's loupes. In certain embodiments, an augmented reality navigation system is compatible with personal prescription glasses. In certain embodiments, an augmented reality navigation system provides a minimum field of view of 40 degrees (e.g., 50 degrees, 60 degrees, 70 degrees, 90 degrees, or more) as measured on a diagonal. In certain embodiments, an augmented reality navigation system comprises a head mounted display and computer subsystem coupled together to provide less than 50 millisecond latency (e.g., less than 20 millisecond latency) from the time that a display screen moves until updated navigation information is received by the display screen. In certain embodiments, a display screen can have a frame rate of 30 frames per second or more (e.g., 60 frames per second or 120 frames per second).

The augmented reality navigation systems disclosed herein comprise a head mounted display comprising an at least partially transparent display screen. The head mounted display comprising an at least partially transparent display screen can have a form factor similar to eyeglasses. For example, it can be binocular or monocular (i.e., the display screen can be used to augment vision in one or both eyes). In certain embodiments, the head mounted display is a binocular head mounted display. A binocular arrangement may be made of one contiguous display screen at least partially covering both eyes when worn or it may be two separate display screens (i.e., one screen for each eye). The head mounted display may be held on a wearer's head using armatures (as in a typical pair of eyeglasses) or some other mounting means (e.g., a strap, band, or fixture sized and shaped to be worn on a human head). The at least partially transparent display screen configured to display augmentation graphics can be any suitable commercially available display screen, for example, those used in heads up displays for piloting or athletics. The display screen is at least partially transparent such that a wearer can see at least a portion of their natural field of view through the display screen while also seeing any augmentation graphics displayed on the screen. In certain embodiments, the display screen is a high resolution display screen (e.g., has a resolution of at least 1280×720).

The augmented reality navigation subsystems disclosed herein comprise at least one detector. A detector is one suitable for use in determining spatial information about real-world features in the field of view of the detector(s). A detector can be an optical camera (e.g., a video camera), an EMF detector, a LiDAR detector, an acoustic detector, an RF detector, or similar energy sensor. The detector receives information from the environment in the field of view of the detector and produces a detector input signal that is sent to the computing subsystem. In certain embodiments, a detector is disposed (e.g., attached) to a head mounted display). In certain embodiments, a detector is connected (e.g., electrically) but spatially remote from the head mounted display. In certain embodiments, fiducials of an appropriate type are selected and used during a surgical procedure based on the type of detector connected to the head mounted display. For example, fiducials that output an EMF signal are detected by an EMF detector mounted to the head mounted display. One or more fiducials may be disposed on a head mounted display for tracking and/or orienting the head mounted display in the surgical environment (e.g., as detected by an auxiliary detector or a second augmented reality navigation system). In certain embodiments, the detector is an optical camera and image recognition is performed by the computer subsystem on the detector input signal in order to determine one or more real-world features. Detectors of different types can be used in combination in a single augmented reality navigation system. Two detectors of the same type may be disposed on a head mounted display and spatially separated thereon (e.g., in order to triangulate real-world features). In certain embodiments, a detector is removable such that it can be replaced by a detector of a different type. In certain embodiments, a detector coupled with a computer subsystem enables patient registration accurate to within 2 mm (e.g., within 1.5 mm or within 1 mm) RMS for each position degree of freedom. In certain embodiments, one or more detector(s) (e.g., disposed on a head mounted display) are configured to provide accurate registration throughout a period of time (e.g., a surgical procedure) over a certain spatial volume in a surgical environment (e.g., a volume larger than a spherical volume of 2 foot radius, 4 foot radius, 6 foot radius, or larger). In certain embodiments, such a volume may further be defined by a cone whose apex is located at the head mounted display.

In certain embodiments, an augmented reality navigation system comprises a motion sensor. The motion sensor can track motion of a wearer's head over time. Such tracking can be used to, for example, smooth, or even remove, jitter of augmentation graphics generated by natural small movements of a wearer's head. In certain embodiments, a motion sensor also provides a means for determining motion of a wearer's head and provides a new orientation and/or position of the head mounted display to the computer subsystem in order to update augmentation graphics displayed on a display screen of the head mounted display. In certain embodiments, a motion sensor is configured to provide a less than 2 cm (e.g., less than 1 cm) drift in the position of augmentation graphics from their baseline position (i.e., as determined by the registration of the augmented reality navigation system to a patient's anatomy), as measured in an open loop. In certain embodiments, the motion sensor coupled with a detector in an augmented reality navigation system provides optically calibrated (i.e., closed loop) sub-millimeter drift per hour. In certain embodiments, a motion sensor is used to record user input used for making selections (e.g., a head nod or shake).

In certain embodiments, an augmented reality navigation system comprises a microphone. The microphone may be disposed on the head mounted display. The microphone may be used to receive surgeon commands (i.e., verbal commands) for use in controlling the augmented reality navigation system. For example, verbal commands may serve as user input for making a selection, modify or update settings or graphics of the display screen, or other similar tasks. For example, verbal commands may be used to rearrange virtual display panels displayed on a display screen of a head mounted display or to change the navigational information displayed on a virtual display. Similarly, graphics overlaid may be modified by verbal commands (e.g., to change brightness, color, or data source for the overlaid graphics).

In some embodiments, in addition to or in place of verbal commands or commands input by motion of a motion sensor, gestures made by a surgeon may be used to signal selections or control an augmented reality navigation system. For example, in certain embodiments, a surgeon can make swipe, click, resize, or refresh type gestures (e.g., similar to those used with smartphones or other touch control devices) to control the augmented reality navigation system. Such gestures may be made in a manner that is detectable by a detector of the augmented reality navigation system. For example, gestures may be detected using image-recognition type procedures (e.g., when a detector is an optical camera). For example, a surgeon may wear or hold a fiducial detectable by the augmented reality navigation system when making a gesture such that the gesture is detected based on motion of the fiducial. In certain embodiments, alternatively or additionally, an auxiliary mechanical input (e.g., foot pedal) may be used as an input (e.g., selection) device.

The augmented reality navigation systems disclosed herein comprise a computer subsystem. The computer subsystem, inter alia, processes (e.g., renders) augmentation graphics for display on a display screen of an augmented reality navigation system. The computer subsystem can be remote. For example, a computer subsystem can be connected to a head mounted display through a cable with a quick disconnect. Such a cable can also provide power to components of a head mounted display (e.g., a display screen). In certain embodiments, a computer subsystem is disposed partially or entirely on a head mounted display (e.g., that operates using battery power). In certain embodiments, a computer subsystem is configured to receive navigation input data that comprises navigational information from a robotic surgical system. For example, a trajectory stored in the robotic surgical system and/or coordinates stored in the robotic surgical system (e.g., recorded using the robotic surgical system). In certain embodiments, a computer subsystem can control a robotic surgical system using output (such as trajectory data output) from an augmented reality navigation system.

In certain embodiments, a computer subsystem is configured to assist in pre-operative and/or intra-operative planning (e.g., trajectory planning). In certain embodiments, the computer subsystem is configured to perform trajectory planning using a pointer tool and/or trajectory selection guidance augmentation graphic (e.g., crosshair) displayed on a display screen. In certain embodiments, a computer subsystem comprises a model module that, inter alia, stores, accesses, and/or updates a model of patient anatomy (e.g., derived from medical image data). In certain embodiments, a computer subsystem comprises a coordinate module that, inter alia, creates, stores, accesses, and/or updates a reference coordinate system used for navigation. Such a reference coordinate system may be defined during a registration method (e.g., at the start of a surgical procedure). A coordinate module may be used to perform reregistration that may happen continuously or periodically during a surgical procedure, wherein the registration may be performed using the augmented reality navigation system.

In certain embodiments, an augmented reality navigation system operates cooperatively with an auxiliary navigation subsystem. For example, an auxiliary detector in a surgical environment may be used to provide additional detection of real-world features in a surgical environment (in addition to those detected by a detector disposed on a head mounted display). In this way, in certain embodiments, an augmented reality navigation system is couple with an existing navigation system used in conjunction with a robot surgical system in order to navigate during a surgical procedure. For example, a registration performed by an augmented reality navigation system can be compared to a registration performed by an auxiliary detector to determine accuracy of the registration being used by the augmented reality navigation system during navigation of a surgical procedure. A computer subsystem can perform a reregistration to minimize error between a registration according to an augmented reality navigation system and an auxiliary detector. When an auxiliary detector is used, registration precision and tracking during a procedure may be improved, for example, due to each detector detecting real-world features that are otherwise obfuscated from the other detector(s). In certain embodiments, an auxiliary detector is a detector disposed on a head mounted display of a second augmented reality navigation system. An auxiliary detector, when present, may be used to detect one or more fiducials disposed on a head mounted display (e.g., to assist in registration, jitter correction and/or drift correction).

In certain embodiments, two or more augmented reality navigation systems are used cooperatively and/or conjunctively (e.g., simultaneously). For example, two surgeons may each wear a head mounted display during a surgical procedure. In certain embodiments, navigational information from one head mounted display (e.g., detector input data from a detector mounted to the head mounted display) may be provided to the other head mounted display, for example, in order to share a common registration or provide a video input feed for display on a display screen of one head mounted display from a detector of another head mounted display. In certain embodiments, a video input feed is provided to an external monitor (e.g., on a nearby wall or in a remote location, such as a class room) for view by other persons (e.g., in the same surgical environment), either in addition to or in alternative to being provided to a second augmented reality navigation system. In certain embodiments, fiducials disposed on each head mounted display assist in co-registering two augmented reality navigation systems used in a single surgical environment. Two or more augmented reality navigation systems may share a common computer subsystem (e.g., each be connected by its own cable to a common computer subsystem).

Exemplary Augmented Reality Navigation Systems

FIG. 1 illustrates an augmented reality navigation system 100 (also referred to as "HMD 100") configured according to some embodiments of the present disclosure. Referring to FIG. 1, the HMD 100 includes a semitransparent display screen 110 connected to a display module that processes and displays augmentation graphics (e.g., video and other images) on the display screen 110 (e.g., a LCD display, a reflective screen on which the display module projects images, etc.) for viewing by a user. The display module may be within a housing 118 of the HMD 100 or may be contained within a communicatively connected computer subsystem.

In the illustrated embodiment, the HMD 100 is mounted to a headband 120 and positioned so that the display screen 110 extends within the peripheral vision of the user. The housing 118 encloses electronic components that display information on the display screen 110 and may operate in combination with a remote but communicatively connected computer equipment and/or with computer equipment integrated within the housing 118 to sense and interpret movement of the head, sense and interpret gestures made by a user's hands or other objects, and/or sense and interpret voice commands by the user. The display screen 110 can provide a monocular see-through display or a stereo set of see-through displays so that the user can view information displayed on the display while looking through the display to view other objects. The headband 120 may include a headlamp, camera, or other apparatus that can be worn on a user's head.

The user is illustrated as wearing glasses 150 that include through-the-lens (TTL) loupes 152, protruding from lenses of the glasses 150, that provide magnified viewing to the user. The display screen 110 extends downward from the housing 118 and is positionable by the user to be in the user's field-of-view or immediately adjacent to the TTL loupes 152 within the user's peripheral vision. The display screen 110 can be a see-through display device allowing the user to see video superimposed on the environment seen through the display screen 110.

The TTL loupes 152 may not be included in the HMD 100 when the display screen 110 is configured to be in the direct line-of-sight of the user. Alternatively, the display screen 110 can be positioned adjacent to the TTL loupes 152 so that the user can make a minor upward shift in eye line-of-sight from looking through the TTL loupes 152 to instead view information displayed on the display screen 110. In some embodiments the display screen 110 may be incorporated within one or both TTL loupes 152 so that the user can look through the TTL loupes 152 to view graphical images super-imposed on objects within the FOV of the TTL loupe 152. The HMD 100 may be configured to be attachable to any type of eyeglass frames, including prescription glasses, protective glasses, frames without lenses, transparent or protective shields, etc.

The display screen 110 can be moved by a user to a location providing convenient visual reference through a two-arm friction joint linkage 112 that provides telescopic and up-and-down adjustment of location of the housing 118. A ball-and-socket joint 114 is connected between the linkage 112 and the housing 118 to provide planar adjustment of the display screen 110. A pivot joint 116 connected between the ball-and-socket joint 114 and the housing 118 allows the user to pivot the housing 118 and connected display screen 110. The display screen 110 can thereby be flipped-up outside the user's peripheral vision when not being used.

The HMD 100 may include a motion sensor such as an inertial sensor or one or more other sensors, such as a gyroscope, accelerometer (e.g., a multi-axis accelerometer), and/or magnetometer that output a signal indicating a measurement of movement or static orientation of the user's head while wearing the HMD 100. For example, the motion sensor may output a head motion signal that indicates yaw (i.e., rotation of the user's head left or right), pitch (i.e., rotation of the user's head up or down), and/or roll (i.e., side-to-side tilt of the user's head). The sensors may be spaced apart on the headband 120 or enclosed within the housing 118.

The HMD 100 may include an optical camera (e.g., acting as the detector or in addition to other detector(s)) facing away from the user that outputs video and/or other images for processing and relay to other HMDs 100 worn by other personnel assisting with the procedure, to other display devices, and/or to a video server for storage. For example, the camera may be configured to be aligned with the user's line-of-sight when the user has adjusted the display screen 110 to be comfortably viewed by the user. When more than one camera is connected to the HMD 100, video streams from the cameras can be provided to an operational function that estimates distance to an object viewed by the cameras. The operational function can include triangulation of distance to the object based on angular offset of the object viewed in the video streams and a known distance between the cameras.

The camera (or another detector) may be connected to a gesture interpretation module configured to sense gestures made by a user's hands or other objects, recognize a gesture as corresponding to one of a plurality of defined commands, and trigger operation of the command. The HMD 100 may include a microphone connected to a voice interpretation module configured to recognize a received voice command as corresponding to one of a plurality of defined voice commands, and trigger operation of the command.

The headband 120 may have a plurality of attachment points where inertial sensor(s), detector(s) (e.g., optical camera(s)), microphone, etc. can be releasably attached. Some of the attachment points may have rigid supporting structures between them to maintain a defined physical alignment between the attached inertial sensors, detectors etc.

Figure 2:
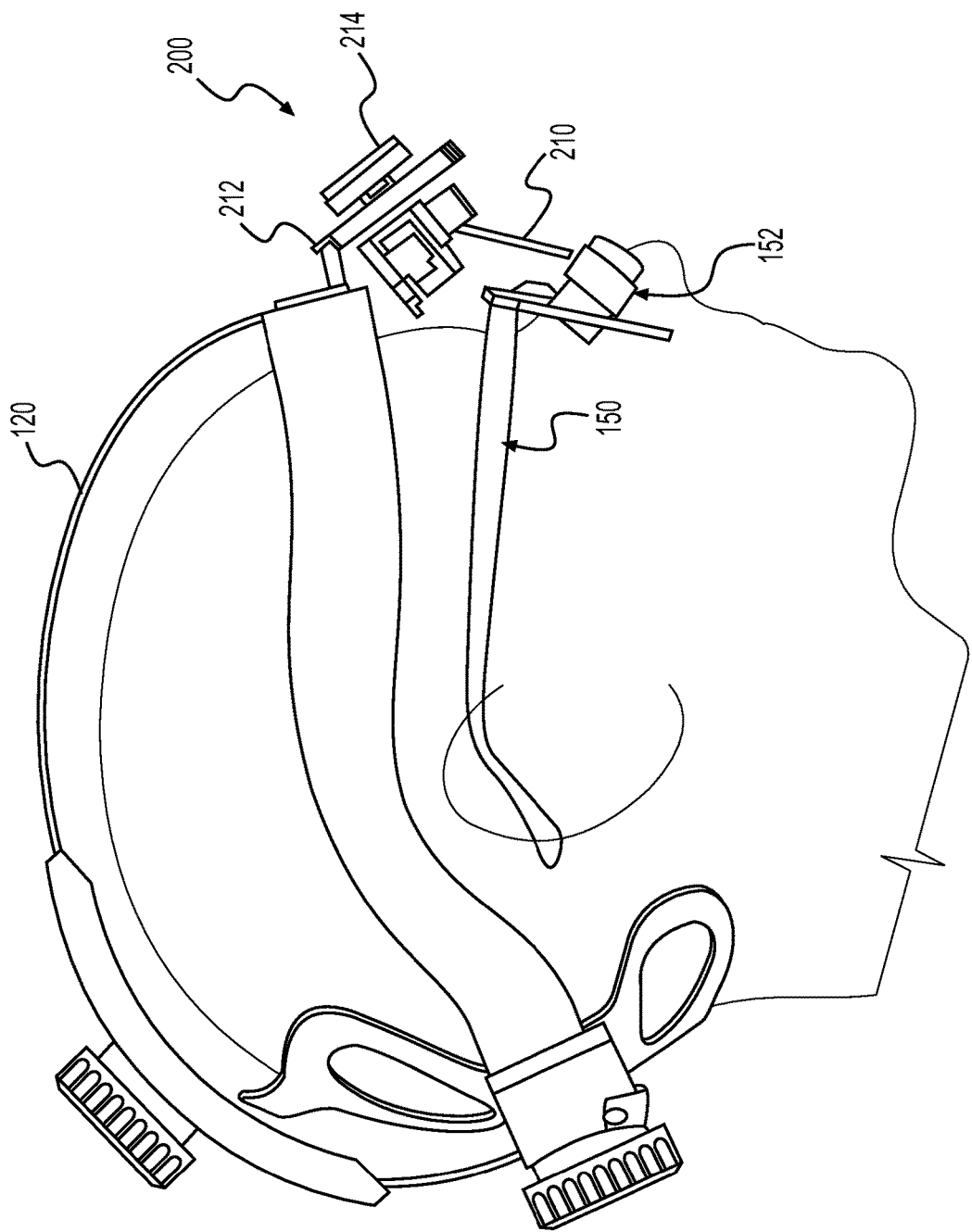
FIG. 2 illustrates a head mounted display apparatus that can be worn on a user's head and operates in accordance with some embodiments of the invention.

FIG. 2 illustrates a side view of another exemplary HMD 200 with a display screen 210 and electronic components 214 (shown without a housing) which are configured according to some embodiments of the present disclosure. The display screen 210 extends downward from the electronic components 214 to be in the user's line-of-sight or immediately adjacent TTL loupes 152 within the user's peripheral vision. The electronic components 214 are connected to the headband 120 via a pivot 212 allowing the electronic components 214 and connected display screen 210 to be flipped-down to a deployed position as shown in FIG. 2 and flipped-up to a stored position when the user does not desire to view the display screen 210.

Figure 3:
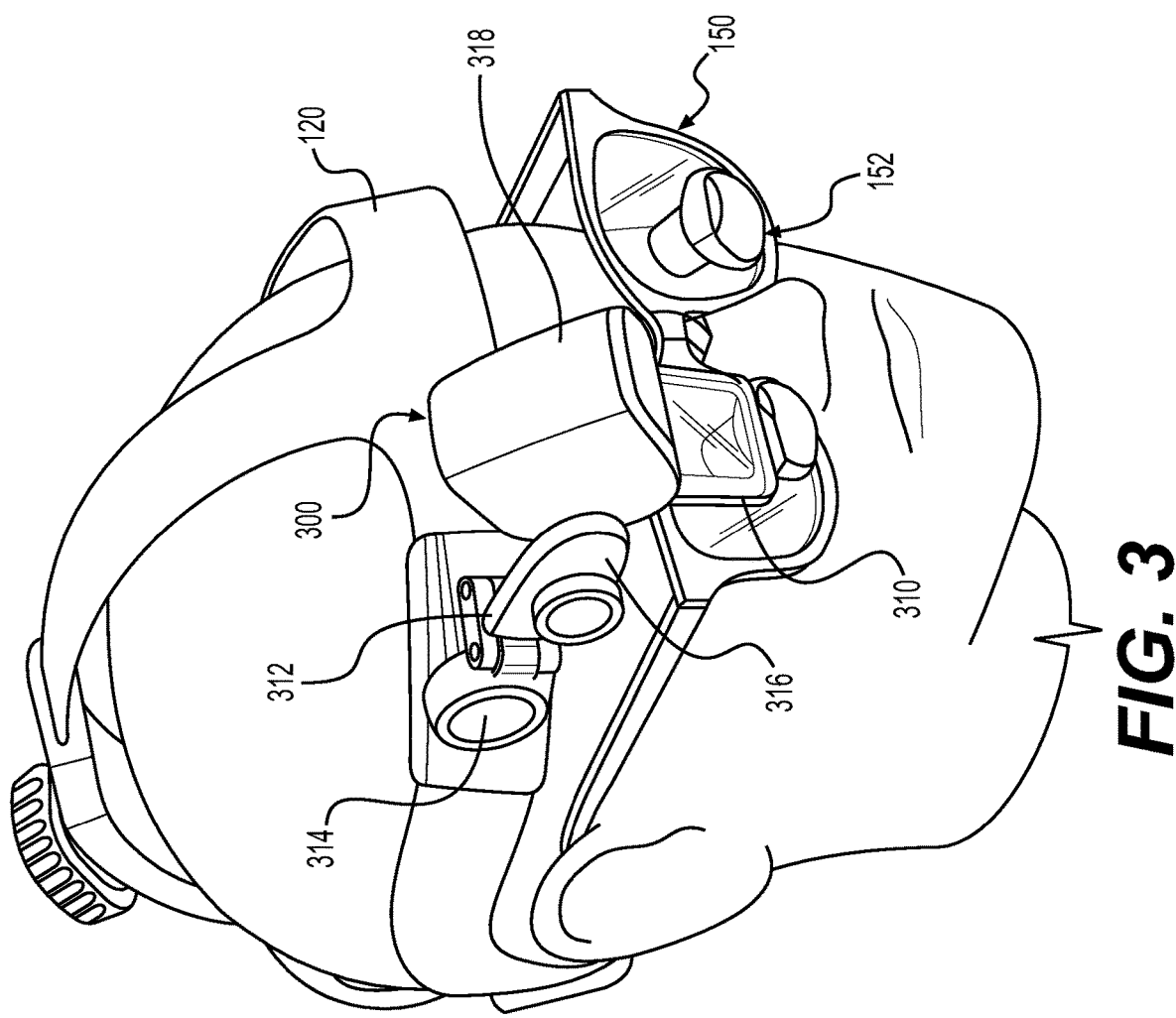
FIG. 3 illustrates a head mounted display apparatus that can be worn on a user's head and operates in accordance with some embodiments of the invention.

FIG. 3 illustrates another exemplary HMD 300 configured according to some embodiments of the present disclosure. The HMD 300 includes a display screen illustrated behind a protective shield 310 that extends downward from a housing 318 enclosing electronic components. The display screen and/or the protective shield 310 may include a coating that provides variable contrast to enhance viewability of displayed information while subject to a range of ambient brightness. The protective shield 310 may provide a variable focal point (diopter). The protective shield 310 can be flipped from a stored up-position to a protective down-position (as shown in FIG. 3) to cover an outside surface of the display screen that faces a patient and function to protect the display screen from fluids and other materials occurring during a procedure. The display screen can be moved by a user through a two-arm friction-joint linkage 312 that provides telescopic and up-and-down adjustment of location of the housing 318 to enable a user to position the display screen at a location providing convenient visual reference. A ball-and-socket joint 316 is connected between the linkage 312 and the housing 118 to provide planar adjustment for the display screen. The linkage 312 is connected to the headband 120 through a pivot joint 314 to allow the user to flip the housing 318 and connected display screen up and down. The display screen can thereby be flipped-up outside the user's line-of-sight or the user's peripheral vision when not being used.

Figure 4:
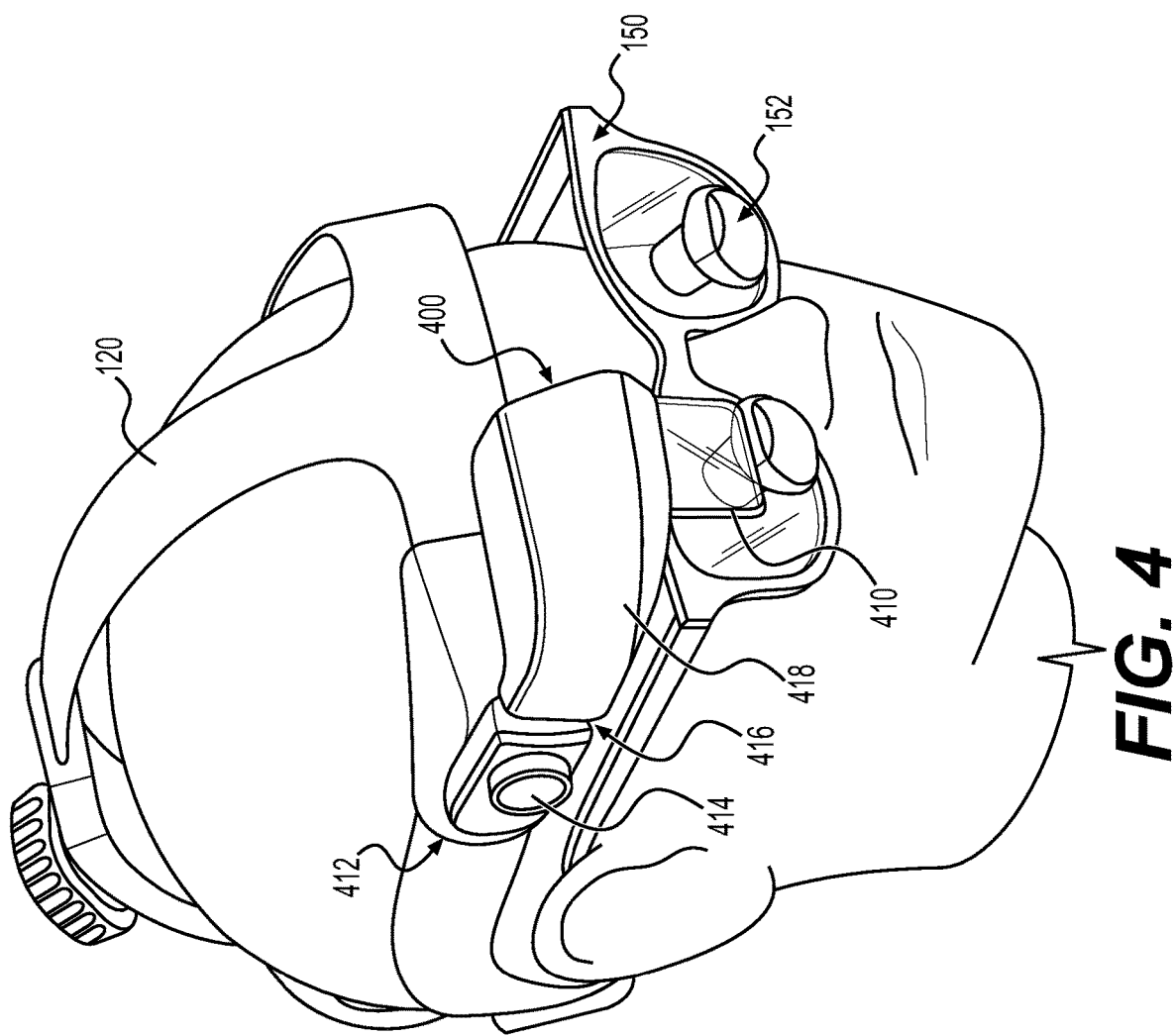
FIG. 4 illustrates a head mounted display apparatus that can be worn on a user's head and operates in accordance with some embodiments of the invention.

FIG. 4 illustrates another exemplary HMD 400 configured according to some embodiments of the present disclosure. The HMD 400 includes a display screen 410 that extends downward from a housing 418 enclosing electronic components. The display screen 410 and housing 418 are connected to a ball-and-socket joint 416 which provides planar adjustment for the display screen 410. The ball-and-socket joint 416 is connected to a pivot 414 that allows the housing 418 and connected display screen 410 to be pivoted up and down, so that the display screen 410 can be flipped-up outside the user's line-of-sight or the user's peripheral vision when not being used. The pivot 414 is connected to a sliding arm 412 that connects to the headband 120. The sliding arm 412 provides telescoping adjustment to allow user placement of the display screen 410 a desired distance from an eye.

Figure 5:
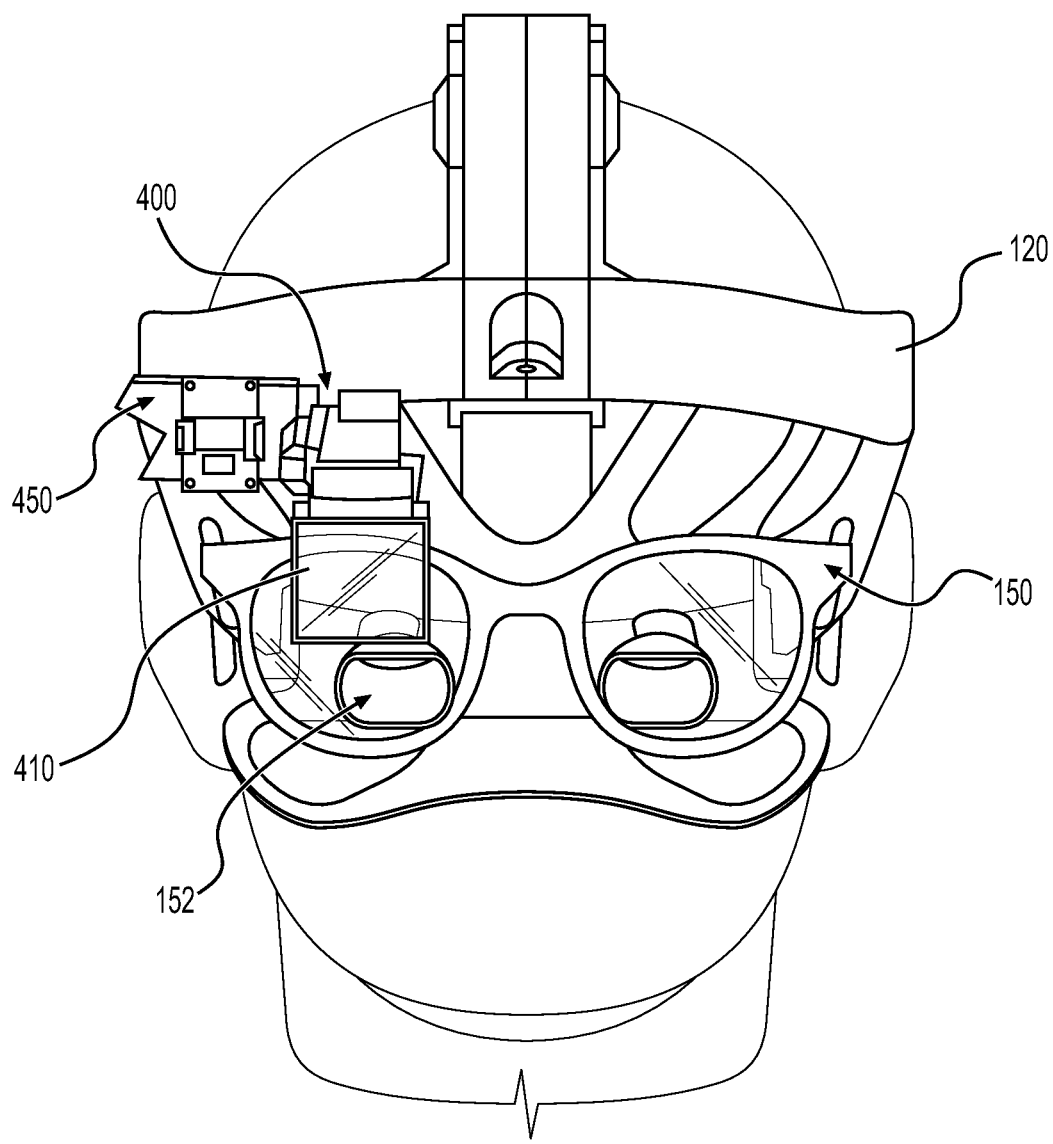
FIG. 5 illustrates a head mounted display apparatus that can be worn on a user's head and operates in accordance with some embodiments of the invention.

FIG. 5 illustrates a front view of the HMD 400 of FIG. 4 with the housing 418 removed to expose printed circuit boards (PCBs) 450 which operationally connect electronic components mounted thereon (e.g., a display screen, a detector, and optionally a microphone and motion sensor). Some of the electronic components are used to display images on the display screen 410, and may operate in combination with integrated or remote computer equipment to sense and interpret movement of the head, sense and interpret gestures made by a user's hands, eyes, or other objects, and/or sense and interpret voice commands by the user. In some embodiments, the PCBs 450 are tilted at a defined non-zero angle relative to vertical to reduce the profile cross-section of the housing 418. For example, the PCBs 450 can extend generally diagonally across the housing 418.

Figure 7:
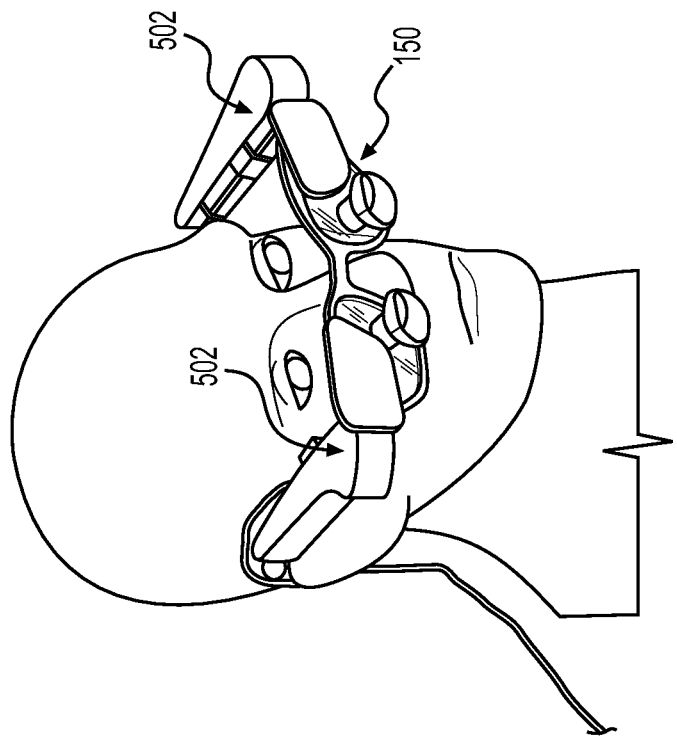
FIG. 7 illustrates a head mounted display apparatus that can be worn on a user's head and operates in accordance with some embodiments of the invention.
Figure 6:
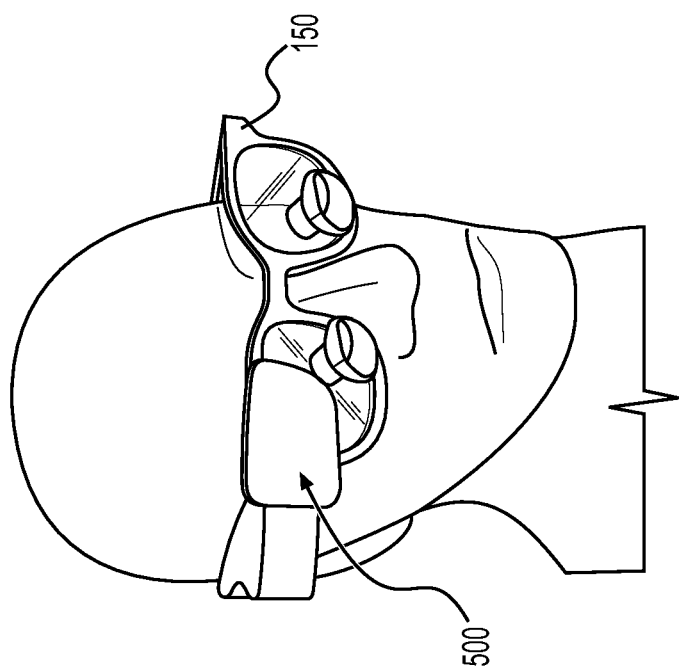
FIG. 6 illustrates a head mounted display apparatus that can be worn on a user's head and operates in accordance with some embodiments of the invention.

FIG. 6 illustrates another HMD 500 having a single display screen connectable to an eyeglass frame to provide monocular viewing by the user. FIG. 7 illustrates another HMD 502 including a pair of display screens that are connectable to opposite sides of an eyeglass frame to provide binocular viewing. Although the display screens in FIGS. 6 and 7 are shown as being opaque, they may instead allow a user to see through the display screen while viewing information displayed thereon.

Figure 8:
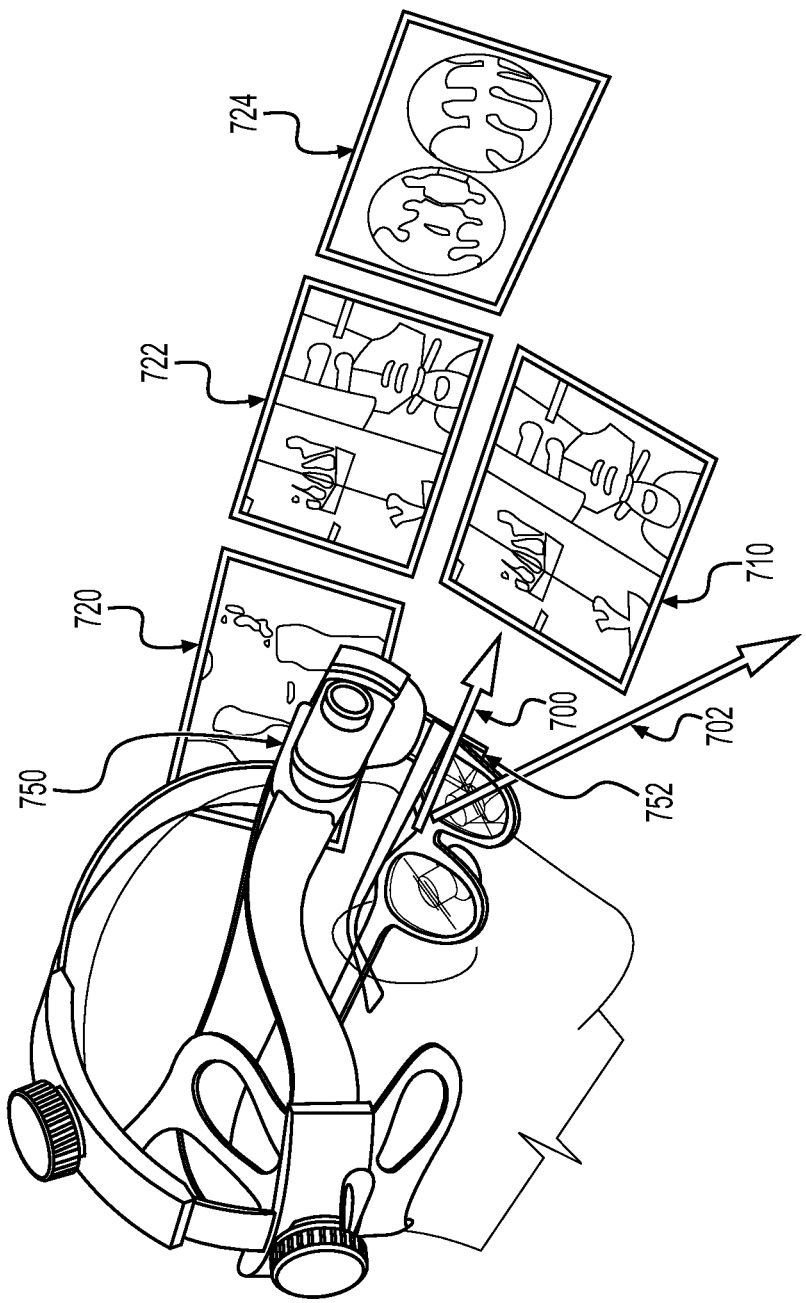
FIG. 8 illustrates operations and methods that may be performed by an augmented reality navigation system that includes a head mounted display to display virtual display panels through a display screen of the head mounted display, according to some illustrative embodiments of the invention.

FIG. 8 shows certain exemplary functionality of certain augmented reality navigation systems. An augmented reality navigation system allows a surgeon or other user to see one or more virtual displays (several in the example shown in FIG. 8) of different medical information without looking away from the surgical site and focusing far away to view physical monitors that may be mounted across the surgical environment or elsewhere adjacent to a patient. In some embodiments, three operational "modes" of the virtual displays are selectively activated based upon pitch of the surgeon's head and the corresponding viewing line-of-sight of the user. The three operations may be separately activated by increasing pitch angle of an HMD 750 through three corresponding ranges of viewing angles, such as low (directly at the surgical space), medium, high (horizontal eye-level). In certain embodiments, the viewing angle of the surgeon can be determined from the head motion signal output by a motion sensor of HMD 750.

A full-screen operational mode may be triggered when it is determined (e.g., by a motion sensor) that a surgeon is looking down at an operation site, which may be determined by when the pitch is below a first pitch threshold (e.g., about −45°). The first pitch threshold may be defined and/or adjusted by the surgeon based on a voice command, entered through a physical user interface, etc. In the full-screen operational mode, a defined one of the video streams (e.g., a primary video stream received via an HDMI channel) is displayed, using augmentation graphics, full screen through a display screen 752 of the HMD 750. A surgeon's corresponding preference settings may be saved in a configuration file stored in the memory 630 of a computer subsystem with an identifier for the surgeon, so that the surgeon's preferred settings can be automatically retrieved upon recognition of the surgeon (e.g., via a login process through the computer equipment 620).

Figure 9:
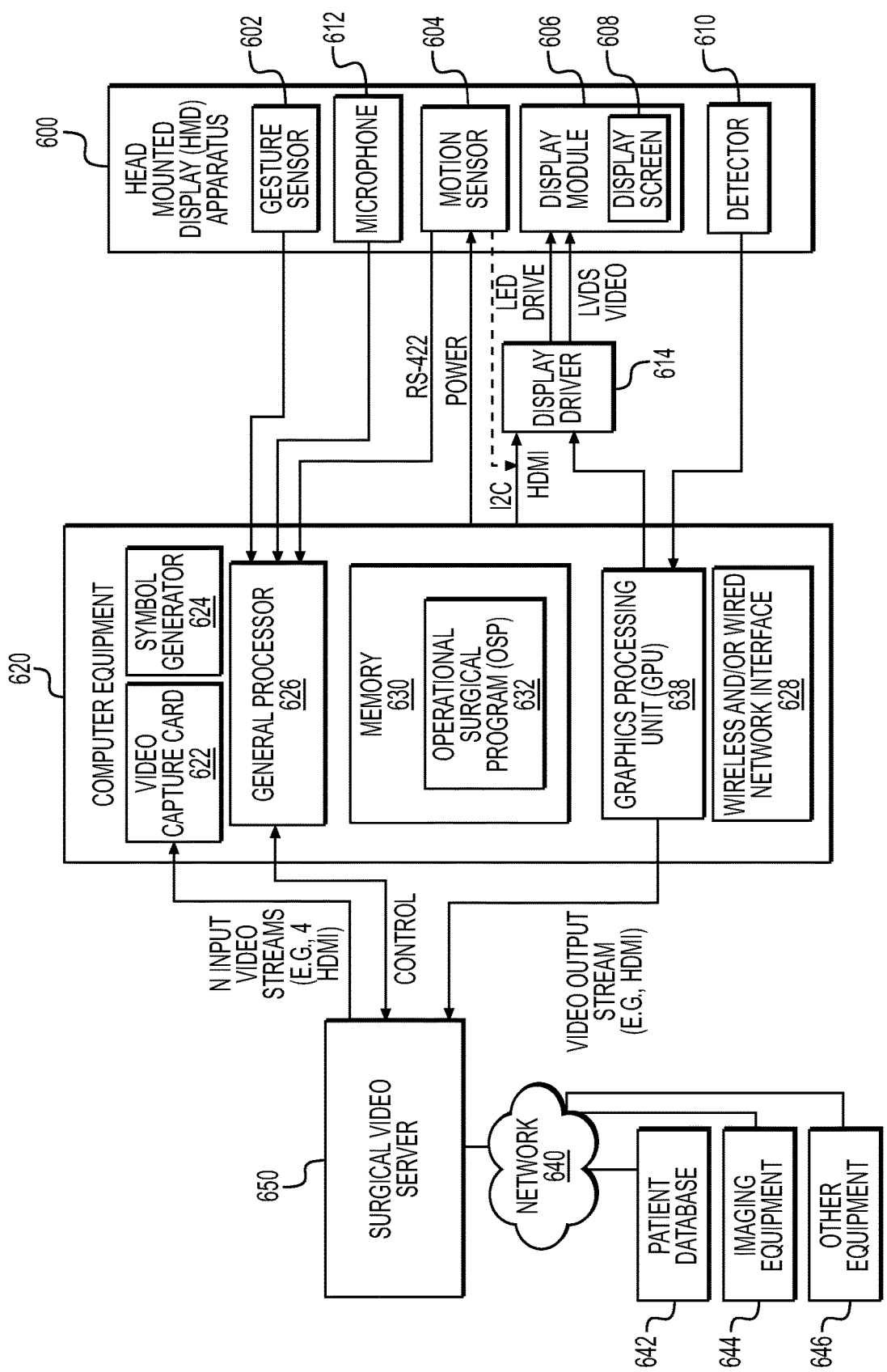
FIG. 9 is a block diagram of electronic components of a computer subsystem coupled to head mounted display in an augmented reality navigation system, according to illustrative embodiments of the invention.

FIG. 9 is a block diagram of electronic components of an exemplary computer subsystem, in accordance with certain embodiments of augmented reality navigation systems disclosed herein, that includes modules 600 for processing data input from and output to a head mounted display, computer processing equipment 620, and a surgical video server 650 (e.g., that provides input data streams). The video server 650 can be connected via a data network 640 to a patient database 642, imaging equipment 644, and other electronic equipment 646, for example. The HMD 600 may correspond to any of the HMDs of FIGS. 1-7, for example. Although the computer equipment 620 is illustrated as being separate from the HMD 600, some or all of the operations disclosed herein as being performed by the computer equipment 620 may additionally or alternatively be performed by one or more processors residing within the HMD 600. Similarly, some of the operations disclosed herein as being performed by the HMD 600 may additionally or alternatively be performed by one or more processors residing within the computer equipment 620.

The video server 650 can receive, store, and route information, video streams between a patient database 642, imaging equipment 644, and other electronic equipment 646 and the HMD 600. As used herein, a video stream can include any type of information that can be provided to a display device for display, including without limitation a still image (e.g., digital photo), a sequence of still images, and video having frames provided at a defined frame rate. A video stream may comprise navigational information. Imaging equipment 644 may include endoscope cameras, magnetic resonance imaging equipment, computed tomography scanning equipment, three-dimensional ultrasound equipment, endoscopic equipment, and/or computer modeling equipment which can generate multidimensional (e.g., 3D) model based on combining images from imaging equipment. A patient database 642 can retrievably store information relating to a patient's medical history, and may store patient images from earlier procedures conducted via the imaging equipment 644. Other equipment 646 may provide information relating to real-time monitoring of a patient, including, for example, hemodynamic, respiratory, and electrophysiological signals.

Computer equipment 620 operationally interfaces HMD 600 to the video server 650. Computer equipment 620 includes a video capture card 622 that can simultaneously receive a plurality (N) of video streams and information (e.g., textual descriptions, audio signals, etc.) from video server 650 and/or directly from imaging equipment 644, patient database 642, and/or the other equipment 646. Computer equipment 620 may communicate with video server 650, HMD 600, and other equipment of the system via a wireless and/or wired network interface 628 using any appropriate communication medium, including but not limited to a wireless air interface (e.g., 3GPP Long Term Evolution (LTE), WLAN (IEEE 802.11), WiMax, etc.), wireline, optical fiber cable, or any combination thereof. In the example embodiment of FIG. 9, the video capture card 622 simultaneously receives up to 4 video streams via 4 HDMI interfaces. In some embodiments, HMD 600 is communicatively connected to computer equipment 620 via an HDMI cable, a USB or RS 422 cable connected to the motion sensor 604 and/or gesture sensor 602, and a USB 3.0 or firewire cable connected to the camera 610. Gesture sensor 602 may be motion sensor 604, detector 610, or a distinct sensor for detecting and processing gestures. A microphone 612 can be connected to the computer equipment 620. The video and/or sensor signaling may alternatively be communicated between HMD 600 and computer equipment 620 through a wireless air interface, such as network interface 628.

HMD 600 includes a display module 606 that processes and displays video and other images on the display screen 608 for viewing by a user. The video streams received by the video capture card 622 are processed by a graphics processing unit (GPU) 638, conditioned by a display driver 614, and provided to the display module 606 for display on the display screen 608. A symbol generator 624 may add graphical indicia and/or textual information to the video stream(s) provided to the HMD 600 based on information received from the video server 650 (e.g., via the patient database 642).

Display driver 614 may reside in the computer equipment 620 or the HMD 600. In some embodiments, display driver 614 receives video via a HDMI interface from GPU 638, and converts a digital video signal to an analog video signal which is output as low-voltage differential signaling (LVDS) to display module 606. Display driver 614 may also provide power and/or other signaling to display module 606 via an LED drive signal.

HMD 600 can include a detector (e.g., optical camera) 610, or a plurality of detectors 610, facing away from a wearer that outputs video and/or other images via a wireless and/or wired network interface 628, illustrated as a HDMI cable in FIG. 9, to GPU 638 for processing and relay to video server 650 for storage and possible further relay to other HMDs 600 worn by other personnel assisting with a procedure. For example, detector 610 may be configured to be aligned with a wearer's line-of-sight when the wearer has adjusted the display screen 608 to be comfortably viewed by the wearer. In certain embodiments, a video signal from detector 610 can be processed through computer equipment 620 and provided to video server 650 for recording what the wearer is viewing during a procedure and/or can be provided as a real-time video stream to other HMDs 600 worn by personnel assisting with the procedure so that the personnel can observe what the user is seeing. A video signal from detector 610 may be augmented by symbol generator 624 with one or more designation symbols such that augmentation graphics displayed on a display screen (e.g., of an HMD worn by another wearer) comprise both the video signal and one or more symbols. Augmentation graphics comprising one or more symbols may, for example, identify the first wearer as the source of the video stream and/or be added to a video stream by a wearer to identify observed features, such as a patient's anatomy.

The HMD 600 may include a motion sensor 604 and/or a gesture sensor 602. Motion sensor 604 may be an inertial motion unit (IMU), gyroscope, accelerometer (e.g., a multi-axis accelerometer), and/or tilt sensor that outputs a head motion signal indicating a measurement of movement of the user's head while wearing the HMD 600. Motion sensor 604 may be powered by computer equipment 620 and may output a head motion signal via a communication interface, such as a RS-422 serial digital interface. For example, motion sensor 604 may output a head motion signal that indicates yaw movement (i.e., rotation of the user's head left or right) and/or indicates pitch movement (i.e., rotation of the user's head up or down).

Motion sensor 604 may be a sourceless orientation sensor. A head motion signal output by a motion sensor may be processed by HMD 600 and/or by computer equipment 620 to compensate for drift error introduced by the motion sensor 604. In some embodiments, one directional reference (e.g., yaw) component of a head motion signal is corrected toward zero responsive to another reference component (e.g., pitch) of the head motion signal being within a threshold offset of a defined value. For example, yaw drift error in the head motion signal can be determined based on monitoring yaw values of the motion signal while the user is looking down at a defined pitch (e.g., pitch being within a threshold range of a defined value) to align the user's eyes with an object (e.g., when a surgeon repetitively looks down to view a surgical site of a patient). In some embodiments, responsive to the pitch component of the head motion signal indicating that a surgeon is looking down for at least a threshold time that is indicative of the surgeon visually concentrating on a surgical site, computer equipment 620 assumes that HMD 600 is stabilized along the yaw axis and computes yaw drift error based on measured change in the yaw component over a defined time interval. The head motion signal is then compensated to remove the determined yaw drift error. In some embodiments, computer equipment 620 measures drift in the yaw component of a head motion signal while a static image is displayed on the display screen, assuming that the surgeon's head is stabilized along the yaw axis, and then compensates the head motion signal to remove the measured drift in the yaw component.

A head motion signal may be processed by HMD 600 and/or by computer equipment 620 to identify an origin for one or more directional reference components from which movement is referenced. For example, an origin location from which yaw is measured may be identified based on an average (e.g., median or mode) of a yaw component of the head motion signal during times when the user is looking down at a defined pitch to align the user's eyes with an object (e.g., surgeon looking down to view a surgical site).

The directional reference (e.g., pitch or yaw) of a head motion signal, which is defined to trigger compensation for drift error and/or which is defined as a reference origin for movement measurement, may be identified based on the user maintaining a substantially constant orientation of HMD 600 for a threshold time (e.g., dwell time). For example, when a surgeon has maintained a relatively constant head position while viewing a surgical site of a patient for a threshold time, the directional reference (e.g., pitch or yaw) of the head motion signal during that dwell time can be used as a basis for compensating for drift error and/or setting as a reference origin for display of virtual display panels (e.g., as illustrated in FIG. 8) and/or other augmentation graphics (e.g., that appear overlaid over a physical object, such as patient anatomy). In some embodiments, a head motion signal may be processed by the HMD 600 and/or by the computer equipment 620 to estimate gyroscope bias(es) giving rise to yaw drift and/or pitch drift accumulating over time based on pseudo-measurements of the yaw and/or the pitch provided by the head motion signal which is expected to be nearly zero each time the surgeon looks down at the same surgical site and steadies the head to center the line-of-sight at a same location on the patient.

Gesture sensor 602 may include any type of sensor that can sense a gesture made by a user. In a surgical environment, use of a gesture sensor 602 to receive a gesture-based command from a surgeon or other OR personnel can be advantageous because it avoids a need for the user to touch a non-sterile surface of the HMD 600 or other device. The gesture sensor 602 may be or include detector 610 which outputs signal (e.g., RGB-D video) displaying movement of a user's hand, fingers, arms or other objects moved by the user along a pathway that the user knows will define a command identifiable by an operational surgical program (OSP) 632 and/or another component of the system. Detector 610 or another camera may be directed toward one of the user's eyes to identify a dwell time of the eye, blink timing, and/or movement of the eye to generate a command from the user to control what is displayed on the display screen 608.

Gesture sensor 602 may alternatively or additionally include one or more photoelectric motion and/or proximity sensors. In some embodiments, gesture sensor 602 has one or more infrared emitters and one or more of photodiodes (e.g., at least a portion of which may additionally function as a detector for navigation). For example, adjacent pairs of an infrared emitter and a photodiode can be spaced apart and arranged to form a directional array facing outward from a housing of HMD 600 to sense presence of a user's hand adjacent to the array and/or to sense a direction of movement as the user's hand is moved across the array. A user may, for example, swipe a hand in a first direction across the array (without touching the housing) to input a first type of gesture recognized by OSP 632 processed by processor 626 which triggers a first type of operation by OSP 632, swipe the hand in a second direction about opposite to the first direction across the array to input a second type of gesture recognized by OSP 632 which triggers a second type of operation by OSP 632, swipe the hand in a third direction about perpendicular to the first direction across the array to input a third type of gesture recognized by OSP 632 which triggers a third type of operation by OSP 632, and so on with other directions of movement being identifiable as other types of gestures provided by the user to trigger other types of operations by OSP 632.

In some embodiments, gesture sensor 602 includes an ultrasonic echo ranging transducer that senses signal echo reflections from a user's hand and outputs a signal to the processor 626 which identifies gestures formed by movement of the hand. In some embodiments, gesture sensor 602 includes a capacitive sensor that senses presence of a user's hand through capacitive coupling between a charge plate and the user's hand. A plurality of capacitive sensors may be spaced apart to form gesture sensor 602 and configured to sense a direction of movement of the user's hand relative to the array of charge plates (e.g., sense an order with which plates experienced increased coupling to the user's hand). Different sensed directions of movement can be interpreted by OSP 632 and/or another component of the system as representing different commands selected by the user for operation.

HMD 600 can include a microphone 612 configured to receive voice commands from a user. The processor 626 executing OSP 632 and/or another component of the system can be configured to recognize a received voice command as corresponding to one of a plurality of defined voice commands, and trigger operation of a command corresponding to the recognized voice command to control information (e.g., navigational information) displayed on a display screen (i.e., via augmentation graphics).

In some embodiments, video signal from detector 610 is displayed on display device 608 of an HMD 600, and symbol generator 624 in combination with OSP 632 processed by the processor 626 may operate to display trajectory selection guidance augmentation graphics (e.g., reticle such as crosshairs) that can be positioned within a plane of the video stream by a surgeon (e.g., responsive to recognition of voice commands via a microphone 612 or to gestures via gesture sensor 602). In this manner, a surgeon may orient his or her natural field of view to a surgical site, steer a trajectory selection guidance augmentation graphic to be aligned with a point-of-interest (e.g., in a patient's anatomy), and trigger capture of data that represents a position and/or orientation (e.g., of a trajectory) of interest that is indicated by the trajectory selection guidance augmentation graphic. For example, using an augmented reality navigation system registered to a patient anatomy, a trajectory can be planned by orienting and/or positioning a trajectory selection guidance augmentation graphic (e.g., through movement of a surgeon's head or movement of the augmentation graphic) and providing a user input that captures a position and/or orientation indicated by the trajectory selection guidance augmentation graphic. A trajectory selection guidance augmentation graphic may be fixed in position on a display screen or may be moveable. In some embodiments, a pointer tool is used to determine such a point of interest.

Figure 10:
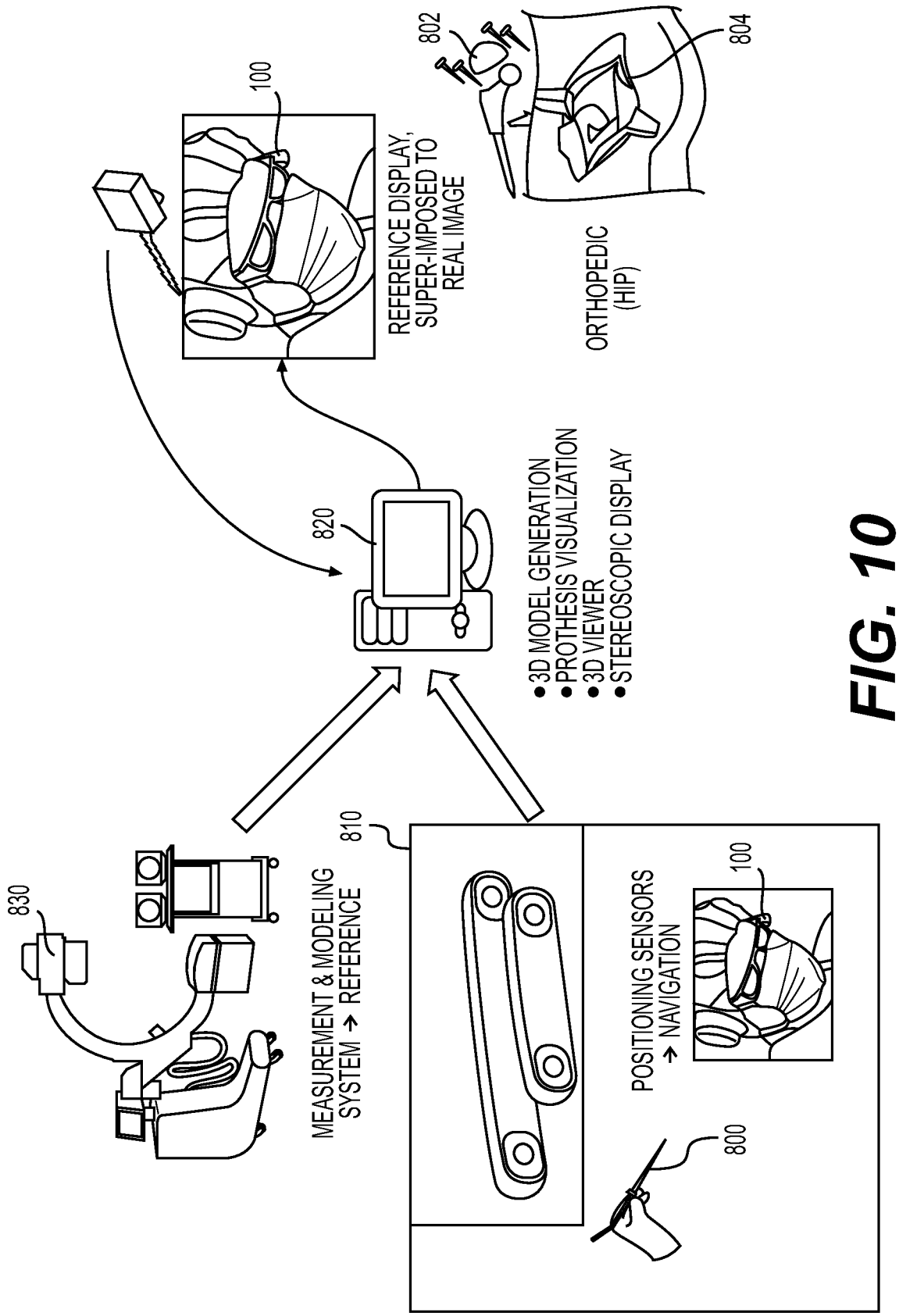
FIG. 10 is a block diagram of components of an augmented reality navigation system that tracks the location of equipment (surgical tools, a surgeon's head mounted display, and parts of a patient's anatomy, and generates a three dimensional (3D) model from patient data that is displayed on the head mounted display to be rendered super-imposed at a visually aligned location on the patient's body in accordance with illustrative embodiments of the invention.

FIG. 10 is a block diagram of components of an augmented reality surgical system that include a position tracking system 810 (e.g., one or more detectors mounted on a head mounted display and, optionally, cameras spaced apart in the operating room) that track the location of a patient's anatomy, surgical tool 800 and/or surgical apparatus (e.g., an implant or other object used as part of a surgical procedure). Generally, any object comprising a real-world feature capable of being identified by a detector (e.g., mounted on a head mounted display) can be tracked and used in navigation with an augmented reality navigation system in accordance with embodiments disclosed herein. In certain embodiments, computer subsystem 820 uses patient data from imaging equipment 830 to generate a two dimensional (2D) or three dimensional (3D) model. Imaging equipment 830 may include, without limitation, x-ray equipment, endoscope cameras, magnetic resonance imaging equipment, computed tomography scanning equipment, three-dimensional ultrasound equipment, endoscopic equipment, and/or computer modeling equipment which can generate a multi-dimensional (e.g., 2D or 3D) model of a targeted site of a patient. The patient data can include real-time feeds and/or earlier stored data from imaging equipment 830, and may include an anatomical database specific for the particular patient or more generally for humans.

The model can include representations of real-world features that assist with performing correlations (e.g., registrations) between virtual locations of the representations of real-world features in the patient model and physical locations of the real-world features (e.g., on the patient's body). Computer subsystem 820 can use (i) present locations of HMD 100, surgical site 804, and surgical tool 800 and/or surgical apparatus 802 obtained by position tracking system 810 by detecting one or more real-world features and (ii) the real-world feature representations contained in a patient model to transform the patient model to a present perspective view of a wearer of HMD 100. Some or all of the transformed patient model can then be displayed on a display screen of HMD 100 using augmentation graphics, for example, to provide the surgeon with an augmentation graphical overlay that is precisely oriented and scaled on the surgical site 804 or other target location on a patient.

Computer subsystem 820 may augmentation graphics representing a patient model, a surgical tool and/or a surgical apparatus on a display screen 110 of an HMD 100. Augmentation graphics may be portions of a surgical tool and/or a surgical apparatus that are otherwise not viewable by a surgeon during at least a portion of a surgical procedure (e.g., are covered by patient anatomy such as a patient's skin). Computer subsystem 820 may additionally be configured to animate movement of a displayed patient mode, tool and/or surgical apparatus (e.g., to illustrate a planned procedure relative to a defined location of the surgical site 804 or other target location on the patient's body). The HMD 100 may be communicatively connected to the computer subsystem 820 through a wireless transceiver and/or wired network interface.

Computer subsystem 820 may compare patterns of objects in a detector input signal (e.g., video stream) from a detector (e.g., camera) on the HMD 100 to patterns of real-world features in the patient model to identify levels of correspondence, and may control transformation of the patient model responsive to identifying a threshold level of correspondence between the compared objects. For example, real-time video captured by an HMD-mounted camera during surgery of a patient may be processed by computer subsystem 820 and compared to video captured by one or more other sources, e.g., an auxiliary detector of imaging equipment 830. The pattern matching may be constrained to characteristics of an object or a set of objects defined by a surgeon as being relevant to a present procedure.

The computer subsystem 820 can control transformation of a patient model for display on the display screen 110 using augmentation graphics based on the pattern matching (e.g., with or without comparing to a detector input signal from auxiliary imaging equipment). The computer subsystem 820 may display on the display screen 110 an indicia (e.g., a crosshair or color marker) aligned with an identified object within the video from the HMD camera to assist the surgeon with identifying the corresponding location on the patient. In one embodiment, the computer subsystem 820 displays a graphical indicia on the display screen 110 aligned with one of the anatomical objects displayed on the display screen 110 from the rotated and scaled three dimensional anatomical model responsive to identifying a threshold level of correspondence between a pattern of the one of the anatomical objects and a pattern of one of the anatomical objects in the video stream from the video camera.

Computer subsystem 820 may similarly receive other data and video streams from a patient database and other electronic equipment, which can be selectively displayed on one or more display screens of an HMD 100 using augmentation graphics. As used herein, a video stream can include any type of information that can be provided to a display device for display, including without limitation a still image (e.g., digital photo), a sequence of still images, and video having frames provided at a defined frame rate. Computer subsystem 820 can retrieve patient health information relating to a patient's medical history and data obtained by real-time monitoring of a patient, including, for example, hemodynamic, respiratory, and electrophysiological signals. Such information can be displayed on a display screen using augmentation graphics and, moreover, can appear to be displayed on a virtual display screen and/or overlaid over an object in a surgical environment (e.g., patient anatomy or surgical equipment).

In certain embodiments, computer subsystem 820 is physically separate (e.g., remote) from a connected HMD 100. In some embodiments, some or all of the operations disclosed herein as being performed by a computer subsystem 820 are additionally or alternatively performed by one or more processors residing within an HMD 100. Likewise, in some embodiments, some or all of the operations disclosed herein as being performed by an HMD 100 are additionally or alternatively performed by one or more processors residing within a computer subsystem 820.

Figure 11:
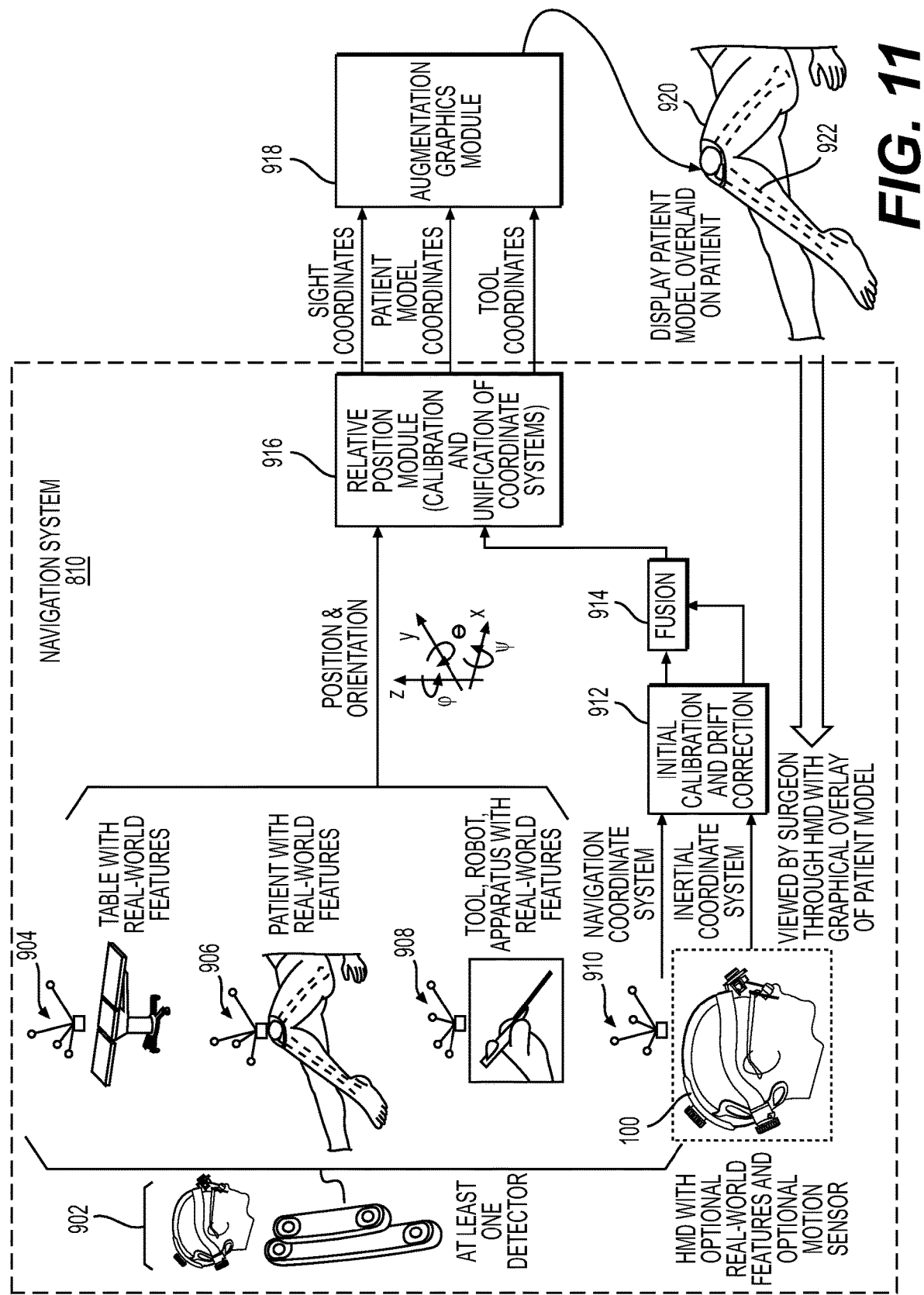
FIG. 11 is another block diagram of the electronic components and modules of an augmented reality surgical system, in accordance with illustrative embodiments of the invention.

FIG. 11 is a block diagram of electronic components in an augmented reality surgical system according to some embodiments of the present disclosure. Referring to FIG. 11, the navigation system 810 can include at least one detector 902 that tracks at least one of, for example, real-world features identifying and/or attached to a surgical table 904, real-world features identifying and/or attached to patient 906 (e.g., adjacent to a surgical or other target site), real-world features identifying and/or attached to a surgery tool and/or surgical apparatus (e.g., implant) and/or robotic surgical system 908, and, optionally real-world features attached to an HMD 910. In some embodiments, the detectors used for navigation (e.g., tracking) are exclusively attached to a HMD (i.e., no auxiliary detector(s) are used). In these embodiments, the volume over which a robotic surgical system and a patient and, optionally, a patient model, are registered is defined by a volume at least temporarily within the field of view of the detectors attached to the HMD. In some embodiments, auxiliary detector(s) not attached to a HMD are used for navigation. For example, in some embodiments, the at least one detector 902 includes a plurality of cameras that are spaced apart at defined locations within an operating room and each having a field of view that can observe objects to be tracked. In the illustrated example, the camera system 902 includes two sets of cameras spaced apart by a known distance and relative orientation. The navigation system 810 may use, for example and without limitation, active optical real-world features (e.g., light emitting sources) or passive optical real-world features (e.g., light reflectors). Navigation system 810 may additionally or alternatively use electromagnetic field or radiation based navigational tracking, ultrasonic based navigational tracking or the like (e.g., depending on a type of detector mounted to a head mounted display and/or a type of auxiliary detector).

In some embodiments, positioning data of an HMD 100 can include navigation coordinate system data determined from a location of real-world features attached to an HMD 910 and/or inertial coordinate system data from a motion sensor attached to the HMD. In some embodiment, the navigation coordinate system data and the inertial coordinate system data can be compensated for initial calibration and drift correction over time by a calibration module 912 and combined by a fusion module 914 to output combined HMD position data. The calibration component and fusion component may be modules of a computer subsystem.

A relative positioning module 916 identifies the relative position and angular orientation of each of the tracked real-world features 904-910 and the combined HMD position data. A relative positioning component may be a component of a computer subsystem. The module 916 may perform coordinate transformations of relative coordinate systems of, for example, a surgical table, a patient, a surgical tool (and/or a pointer tool), and an HMD 100 to a unified (common) coordinate system. In some embodiments, a relative positioning module 916 outputs sight coordinates data, patient model coordinates data, and tool coordinates data to an augmentation graphics generator module 918 and/or a robotic surgical system. An augmentation graphics generator module 918 may be part of a computer subsystem of an augmented reality navigation system. Sight coordinates data can be generated based on the combined HMD position data transformed to the unified coordinate system. In some embodiments, a spatial position of an HMD (e.g., a position on the HMD, such as a position of a detector mounted to the HMD) is taken to be an origin of a unified coordinate system and additional spatial coordinates determined from various real-world features are registered to the HMD using the unified coordinate system with that position as the origin. Accordingly, in some embodiments, a registration is updated [e.g., continuously (e.g., at a certain refresh rate)] to account for movements of an HMD throughout a surgical procedure that cause the position of the origin of the unified coordinate system in the physical space of a surgical environment to be changed. Movement of an HMD may be determined by a motion sensor or a change in a fixed position real-world feature (e.g., a real-world feature identified by or attached to a surgical table). Patient model coordinates data can be generated based on the position and/or orientation of real-world features identified from or attached to a patient 906 transformed to the unified coordinate system. Tool coordinates data can be generated based on a position and/or orientation of real-world features identified from or attached to a surgical tool 908 transformed to the unified coordinate system. Tool coordinates data can be generated based on a position and/or orientation of real-world features identified from or attached to a surgical tool 908 transformed to the unified coordinate system. In some embodiments, robotic surgical system coordinates data and tool coordinates data are equivalent (i.e., one coordinate system is used for a surgical tool and a robotic surgical system simultaneously, for example, when the surgical tool is attached to the robotic surgical system).

In certain embodiments, augmentation graphics generator module 918 transforms (e.g., scales, rotates, translates) a patient model (e.g., derived from medical image data) to a present perspective view of a wearer of an HMD 100 (e.g., mapped to a corresponding object within the FOV of a display screen 110). Likewise, a model of, for example, a robotic surgical system, a surgical tool, a surgical apparatus, or a trajectory of the same, may be transformed by an augmentation graphics generator module, in some embodiments. In some embodiments, a graphics augmentation generator module 918 may provide video generated based on the transformed patient model to a display screen of an HMD 100 for display as a visual model that is dynamically oriented and scaled as a graphical overlay on a surgical site 804 or elsewhere to a corresponding location on the patient where the wearer of the HMD 100 is presently looking and which contains a corresponding object which is modeled by the patient model.

For example, in some embodiments, an augmentation graphics generator module 918 determines whether any portion of a patient's body is presently within the field of view of what the surgeon sees through the display screen 110 (e.g., using a detector mounted to the same HMD as the display screen) that corresponds to any portion of the transformed patient model. In some embodiments, when a portion of a transformed (e.g., scaled, translated, rotated) patient model corresponds to a portion of the patient's body within the surgeon's field of view through the display screen 110, the image generator 918 generates augmentation graphics for display on the display screen 110 based on the corresponding portion of the transformed patient model, while translating and/or rotating the portion of the transformed patient model and scaling size of the portion of the transformed patient model to provide an accurately scaled graphical representation of the object that was, for example, imaged from the patient or modeled from another source such as an anatomical database.

Thus, for example, in some embodiments, when a surgeon's head is rotated so that a portion of a patient's body having a bone that is modeled through CT imagery data becomes within the field of view of the display screen 110 (e.g., within a field of view of a detector mounted to the same HMD as the display screen 110)), an augmentation graphics generator module 918 transforms a patient model of the bone to generate an augmentation graphical representation of the bone that is displayed in the display screen 110 as a graphical overlay that matches the orientation and size of the bone from the perspective of the surgeon as-if the surgeon could view the bone through intervening layers of tissue and/or organs. Likewise, in some embodiments, at least a portion of a surgical tool, at least a portion of a surgical apparatus, and/or at least a portion of a robotic surgical system (e.g., that is covered by a patient's anatomy) can appear as a graphical overlay matching the orientation and size of the physical object to the surgeon using augmentation graphics, in some embodiments.

In the example illustration of block 920, a leg bone model that has been generated, e.g., based on a CT scan of the leg, is transformed and displayed on a display screen 110 to have an accurate orientation and size (e.g., six degree of freedom positioning) relative to the leg bone when viewed augmentation graphics of the leg bone 922 superimposed on a skin surface of the leg. In this example, the surgeon therefore sees the skin surface of the leg through the semitransparent display screen 110 of the HMD 100 with an graphically illustrated representation of the leg bone model overlaid thereon.

Although the augmentation graphics of the leg bone 922 are illustrated in FIG. 11 as being displayed in a superimposed position on a skin surface of the leg, the augmentation graphics 922 can be displayed at other locations which may be controllable by a surgeon. The surgeon may, for example, select to have the graphical representation 922 displayed with a defined offset distance above or below the leg. Moreover, the surgeon may control the size of the displayed augmentation graphics 922 relative to the leg. The surgeon may, for example, temporarily magnify augmentation graphics 922 to view certain details and then return augmentation graphics 922 to be scaled and aligned with the leg. Additionally, augmentation graphics 922 may be modified to appear to be displayed on a virtual display screen hovering near the surgical site. Augmentation graphics 922 may be modified to also display a portion of a surgical tool, at least a portion of a surgical apparatus, at least a portion of a robotic surgical system, and/or a trajectory of any of the same, either overlaid over the patient's leg or in a virtual display screen.

Use of Augmented Reality Navigation Systems in Surgical Procedures

Augmented reality navigation systems in accordance with embodiments disclosed herein may be used in methods of performing surgical procedures in order to provide and/or assist in navigation during the procedures. As such, navigation input data can be provided to a robotic surgical system, obtained from a robotic surgical system, or both in certain embodiments. Generally, in methods disclosed herein, at least one detector mounted on (e.g., attached to) a head mounted display is used in order to determine coordinate systems used for navigation based on real-world features detected by the at least one detector. In some embodiments, an augmented reality navigation system displays augmentation graphics that show portions of a surgical tool, surgical apparatus, and/or robotic surgical system otherwise hidden from the natural field of view of a surgeon. The surgical tool may be attached to or inserted into a robotic surgical system (e.g., through a tool guide attached thereto). In some embodiments, an augmented reality navigation system receives navigation input data from a robotic surgical system (e.g., comprising a position and/or orientation of the robotic surgical system, a model stored thereon or created therewith, and/or one or more trajectories that could be followed by the robotic surgical system). In some embodiments, an augmented reality navigation system is used in conjunction with a pointer tool in order to define a trajectory that a robotic surgical system can follow. The pointer tool may be attached to or inserted in the robotic surgical system. In some embodiments, an augmented reality navigation system is configured to display a trajectory selection guidance augmentation graphic in order to use the graphic to determine a trajectory that a robotic surgical system can follow.

The methods and systems disclosed herein can be used with robotic surgical systems to perform surgical procedures using a particular robotic surgical system. In certain embodiments, portions or all of a particular surgical procedure are performed without the use of a robotic surgical system. For example, one or more surgical tools may be manipulated in a "free-hand" manor by a surgeon, wherein the surgeon holds the tool(s) or the tool(s) are held by an apparatus not connected to a robotic surgical system. Such free-hand manipulation may occur simultaneously with, before, after, or in place of any action performed by a robotic surgical system (e.g., automatically) or with the assistance of a robotic surgical system. In any such case, an augmented reality navigation system in accordance with one or more embodiments of the present disclosure can be used to display navigational information related to the free-hand manipulation of any surgical tool or implant, such as tracking and trajectory planning of such an implant or surgical tool (e.g., with or without use of any additional and/or auxiliary navigation subsystem). It will be appreciated by one of ordinary skill in the art that, in the following described exemplary methods, where reference is made to a surgical tool attached to or inserted into a robotic surgical system, it may be possible for the augmented reality navigation system being used in the particular exemplary method being describe to likewise perform the same function for a tool being held by a surgeon.

Figure 12:
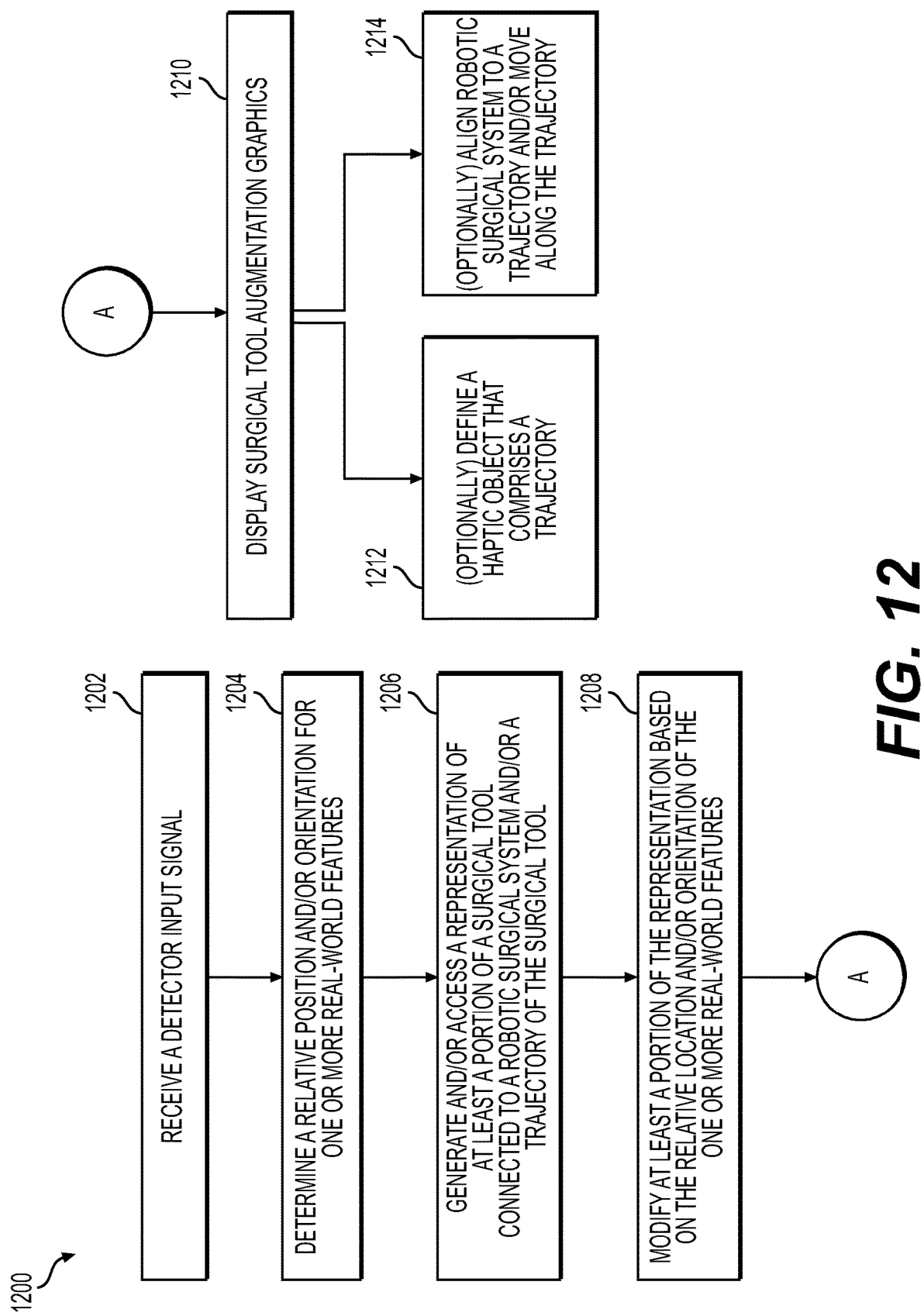
FIG. 12 is a block diagram of an exemplary method for using an augmented reality navigation system to display a graphical representation of a surgical tool and/or its trajectory, according to illustrative embodiments of the invention.

Referring now to the block flow diagram shown in FIG. 12, exemplary method 1200 is a method of using an augmented reality navigation system in accordance with some embodiments of the present disclosure. Exemplary method 1200 is a method whereby an augmented reality navigation system is used to display augmentation graphics representing a surgical tool (e.g., attached to or inserted into a robotic surgical system) and/or its trajectory. It is understood that such an exemplary method can also be adapted to display augmentation graphics representing at least a portion of a surgical apparatus (e.g., implant) that is, for example, attached directly or indirectly to a robotic surgical system. For example, an implant such as a screw may be attached to drill bit that is attached to a robotic surgical system. The apparatus may comprise one or more real-world features (e.g., a fiducial attached thereto). The computational steps of exemplary method 1200 may be performed by a computer subsystem of an augmented reality navigation system.

In step 1202, one or more detectors mounted on a head mounted display of an augmented reality navigation system generate a detector input signal that is received by a computer subsystem of the augmented reality navigation system. The detector input signal represents a field of view of the one or more detectors that comprises at least a portion of a patient anatomy (e.g., relevant to a surgical procedure to be performed). In step 1204, a relative position and/or orientation for one or more real-world features in the detector input signal (i.e., in the field of view represented by the detector input signal) are determined. The relative position and/or orientation may be determined in real time or may be taken as an absolute position and/or orientation represented in a unified coordinate system that resulted from a registration of an augmented reality navigation system and a surgical environment (e.g., a registration between the augmented reality navigation system and objects in the surgical environment such as a patient, a surgical tool, and a robotic surgical system, for example). The detector input signal may be received by a computer subsystem from one or more detectors mounted to a head mounted display of the augmented reality navigation system, one or more detectors mounted to a head mounted display of a second augmented reality navigation system, and/or one or more auxiliary detectors positioned throughout a surgical environment. In step 1206, a representation of at least a portion of a surgical tool connected to and/or inserted into a robotic surgical system and/or a trajectory (e.g., actual or planned trajectory) of the surgical tool is generated and/or accessed. The at least a portion of the surgical tool may be hidden from the natural field of view of a surgeon using the augmented reality navigation system. In step 1208, the representation is modified (e.g., scaled, translated, and/or rotated) by the relative position and/or orientation of the one or more real-world features determined in step 1204. In step 1210, augmentation graphics corresponding to the representation are rendered and displayed on a display screen of the head mounted display of the augmented reality navigation system. Optionally, at least a portion of the surgical tool not hidden from a natural field of view of a surgeon may also be displayed, such that the augmentation graphics show a representation of a larger portion of the surgical tool (e.g., the entire surgical tool) wherein some of the tool is hidden and some of the tool is not hidden. Such a method may also be used for surgical apparatus (e.g., implants). Likewise, the surgical tool augmentation graphics can also be used to show a surgical tool (or portion thereof) that is not physically present (e.g., has not yet been inserted into a robotic surgical system). Additionally, in some embodiments, a position of a surgical tool and/or its trajectory can be visualized over a period of time using augmentation graphics such that a surgeon can watch how a tool will move along a trajectory during at least a portion of a procedure.

The generating and/or accessing a representation step may comprise determining a relative position and/or orientation of one or more real-world features corresponding to the surgical tool of interest. For example, the surgical tool may have a fiducial affixed thereto. The representation may be a stored model (e.g., a CAD model or illustration) of the surgical tool imported into or accessed by the computer subsystem (e.g., provided to the computer subsystem by the robotic surgical system as navigational information). Similarly, in some embodiments, a trajectory of a surgical tool that is otherwise hard to visualize (due to interference from a patient's anatomy) may be displayed on a display screen of a head mounted display as surgical tool augmentation graphics such that the surgeon can view one or more planned trajectories intraoperatively to better visualize the one or more trajectories and therefore better navigate a robotic surgical system. The trajectories for the surgical tool may be provided to the computer subsystem by a robotic surgical system. For example, a surgeon may move a robotic surgical system to a desired position and orientation and save a corresponding trajectory representation that is then later provided to a augmented reality navigation system in generating and/or accessing step 1204. The representation of at least a portion of a surgical tool and/or trajectory that is displayed on a display screen in exemplary method 1200 may be selected using input from a surgeon, for example, using a gesture, motion, or signal input as described herein above.

Figure 15B:
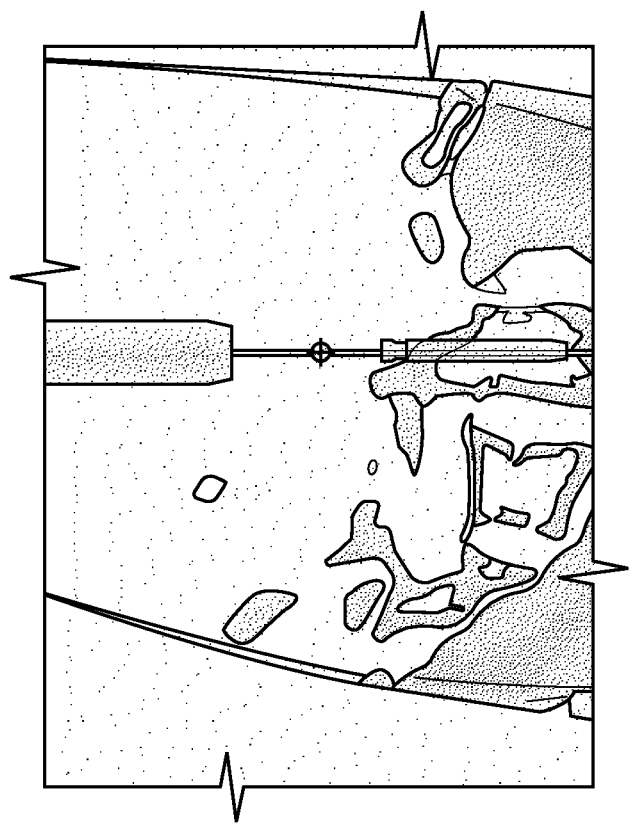
FIG. 15 illustrates navigation information that may be displayed on an augmented reality navigation system during a surgical procedure, according to illustrative embodiments of the invention.
Figure 15A:
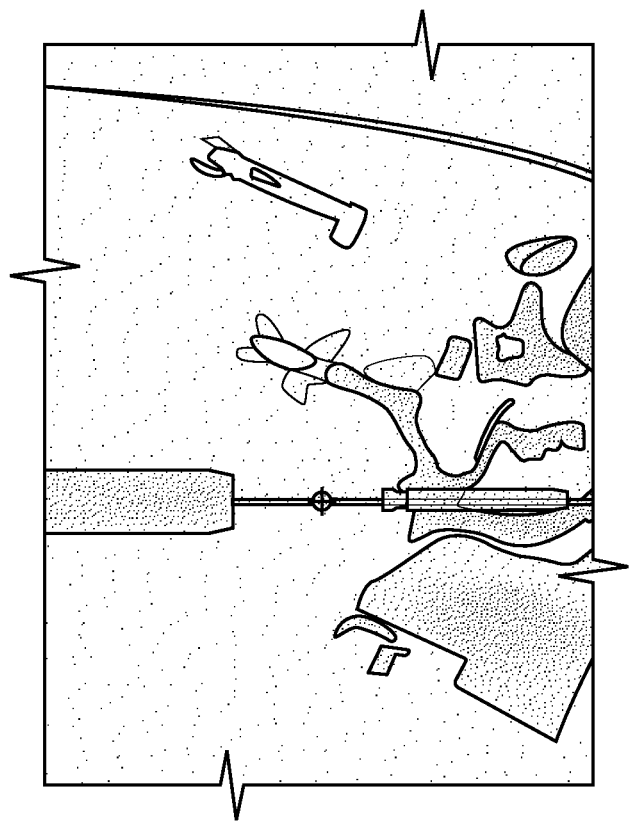
Figure 16:
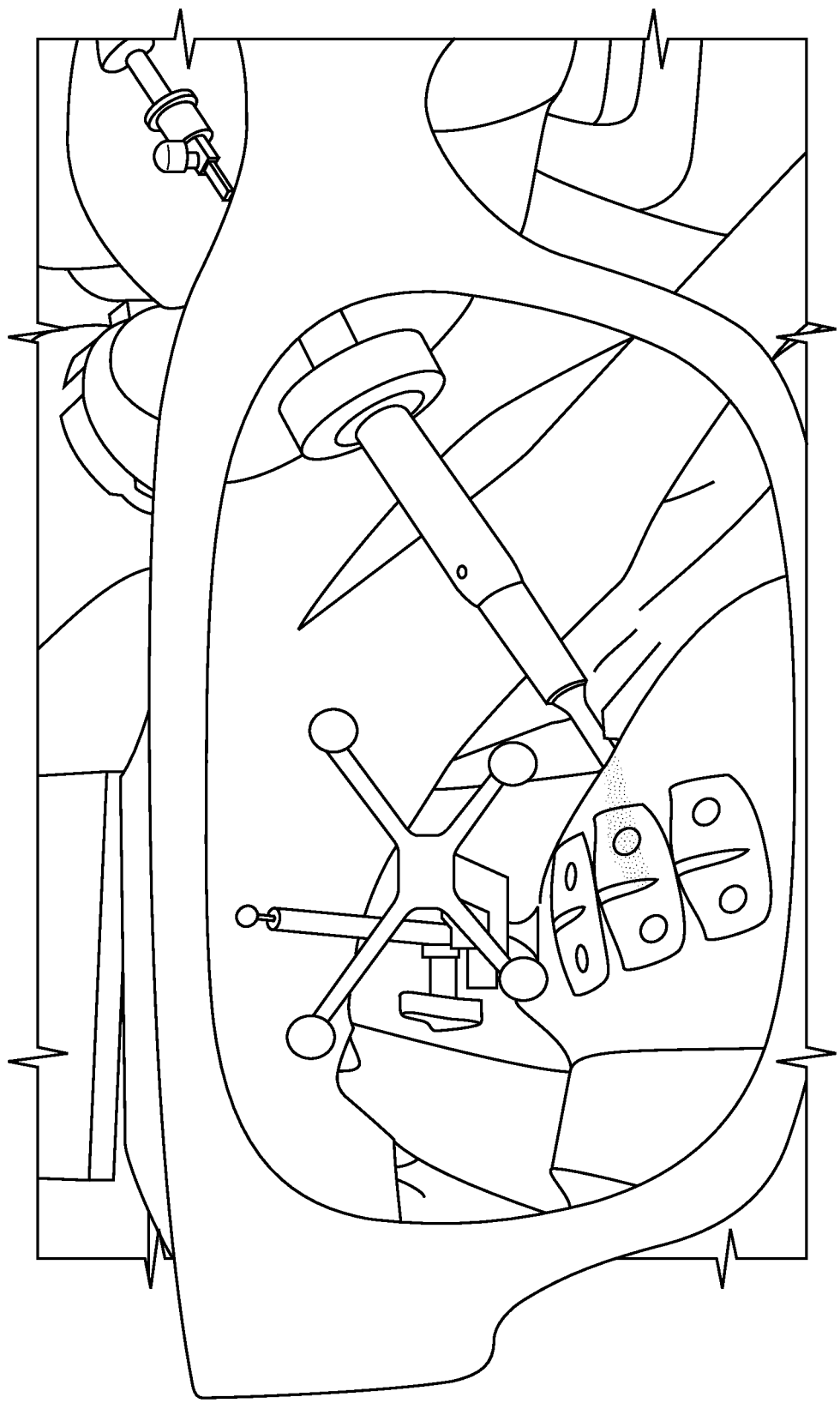
FIG. 16 schematically illustrates portions of a model of a patient anatomy and an implant being inserted along a pre-planned or intra-operatively planned trajectory using a surgical tool connected to a robotic surgical system that are otherwise not visible to the wearer, as displayed on an augmented reality navigation system, according to illustrative embodiments of the invention.

Exemplary method 1200 includes optional steps 1212 and 1214. Either or both of the optional steps may be a part of a method. In optional step 1212, a haptic object comprising the trajectory represented by the surgical tool augmentation graphics displayed in step 1210 is defined. The haptic object may be determined by the augmented reality navigation system (e.g., using relative position(s) and/or orientation(s) of real-world features detected by a detector of the system) and provided to a robotic surgical system by the computer subsystem of the augmented reality navigation system. The robotic surgical system may then be confined in its motion such that at least a portion of a surgical tool connected to or inserted into the robotic surgical system (e.g., the surgical tool corresponding to the representation generated and/or accessed in step 1206) cannot move outside of the haptic object (e.g., due to haptic feedback provided to a surgeon operating the robotic surgical system). In optional step 1214, output from the augmented reality navigation system causes the robotic surgical system to automatically align with the represented trajectory and/or automatically move along the trajectory. In some embodiments, representations of multiple trajectories may be displayed simultaneously and a surgeon may select one of the represented trajectories to have the robotic surgical system align to (e.g., using a pointer tool). In some embodiments, whether one or multiple representations of trajectories are displayed, the augmentation graphics used may appear overlaid over a patient anatomy to give a surgeon an accurate view of how the trajectory intersects a patient's anatomy. In some embodiments, portions of a surgical tool and/or its trajectories appear on a virtual display screen viewed through a display screen of a head mounted display (e.g., in spatial correspondence with a model of patient anatomy such that the trajectory representation, portion of a surgical tool, and model appear to have the same relative position and orientation as physical reality). For example, a virtual display screen may appear as panel A or panel B of FIG. 15. Overlaid augmentation graphics may appear as the sketch in FIG. 16 illustrates.

Figure 13:
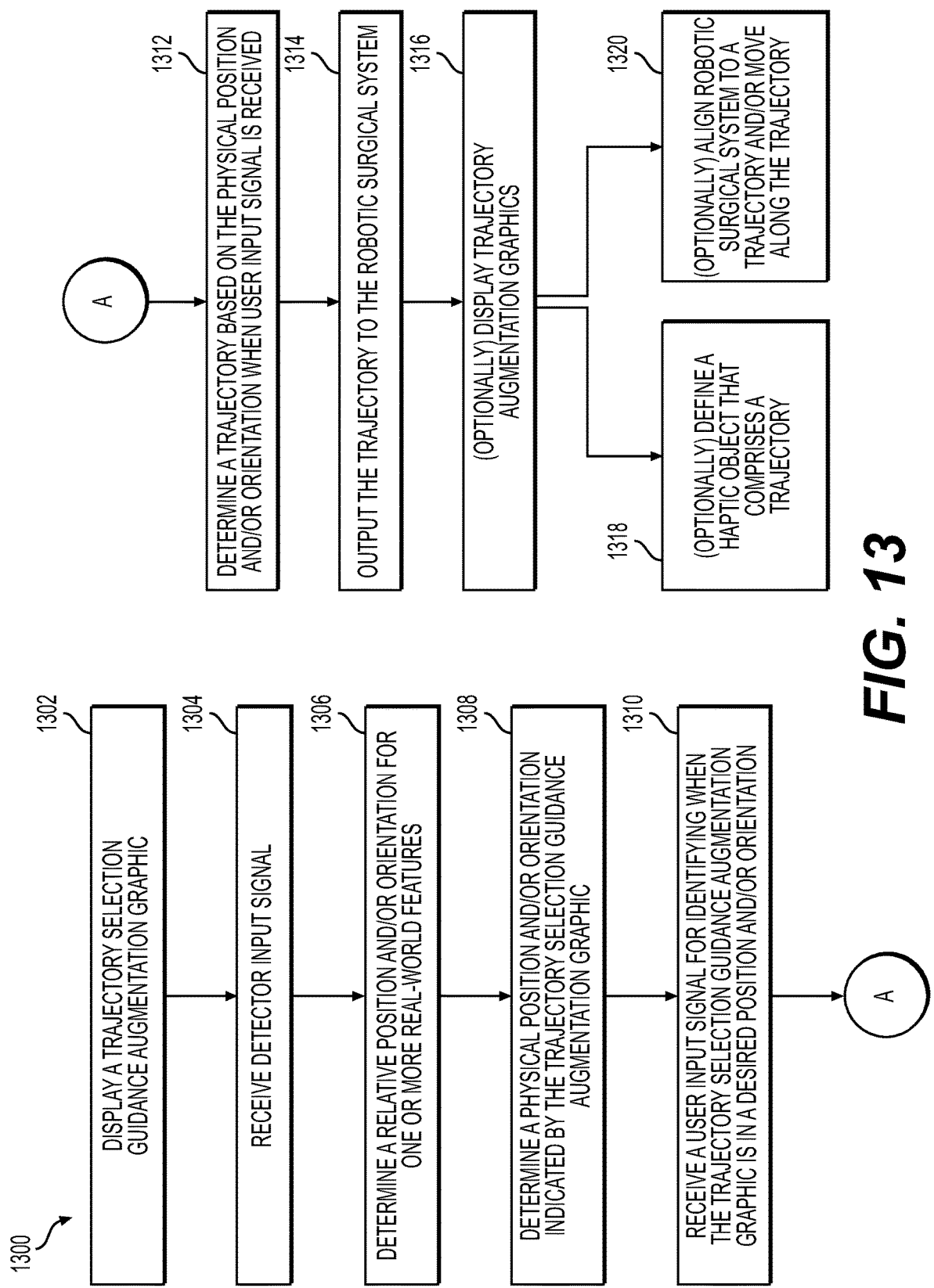
FIG. 13 is a block diagram of an exemplary method for using an augmented reality navigation system with fixed crosshairs, according to illustrative embodiments of the invention.

Referring now to the block flow diagram shown in FIG. 13, exemplary method 1300 is a method of using an augmented reality navigation system in accordance with some embodiments of the present disclosure. Exemplary method 1300 is a method whereby an augmentation reality navigation system uses a trajectory selection guidance augmentation graphic (e.g., a crosshair) to assist in planning and/or updating one or more trajectories corresponding to a surgical procedure. The computational steps of exemplary method 1300 may be performed by a computer subsystem of an augmented reality navigation system.

In step 1302, a trajectory selection augmentation graphic (e.g., crosshair) is displayed on a display screen of an augmented reality navigation system. The trajectory selection guidance augmentation graphic may appear fixed in position on the display screen (e.g., such that motion of the associated head mounted display does not result in the augmentation graphic moving position in a surgeon's field of view). In some embodiments, a trajectory selection guidance augmentation graphic is positionable (e.g., pre- and/or intra- operatively) by a surgeon. For example, a surgeon may prefer the augmentation graphic to appear in a certain location (e.g., center or corner of a display screen) and may position it accordingly using a selection input. In step 1304, a detector input signal is received where the detector input signal corresponds to a field of view of one or more detectors connected to a head mounted display of an augmented reality navigation system, wherein the field of view comprises at least a portion of a patient's anatomy.

In step 1306, a relative position and/or orientation of one or more real-world features (i.e., in the field of view represented by the detector input signal) are determined based on a detector input signal from one or more detectors connected to a head mounted display. The relative position and/or orientation may be determined in real time or may be taken as an absolute position and/or orientation represented in a unified coordinate system that resulted from a registration of an augmented reality navigation system and a surgical environment (e.g., a registration between the augmented reality navigation system and objects in the surgical environment such as a patient, a surgical tool, and a robotic surgical system, for example). The detector input signal may be received by a computer subsystem from one or more detectors mounted to a head mounted display of the augmented reality navigation system, one or more detectors mounted to a head mounted display of a second augmented reality navigation system, and/or one or more auxiliary detectors positioned throughout a surgical environment. In step 1308, a physical position and/or orientation indicated by the trajectory selection guidance augmentation graphic is determined. For example, a surgeon may position and orient a head mounted display such that a trajectory selection guidance augmentation graphic appears to indicate a position of a patient along a preferred orientation (e.g., the position resides within crosshairs on a display screen). The physical position and/or orientation are determined using the relative position(s) and/or orientation(s) determined in step 1308. For example, the coordinates of the physical position and/or orientation indicated by the trajectory may be determined using a unified coordinate system defined during a registration procedure. In step 1310, a user input signal is received by the computer subsystem, wherein the user input signal is generated due to an action (e.g., gesture) by a surgeon using the augmented reality navigation system and the action is made when the trajectory selection guidance augmentation graphic is in a desired position and/or orientation. For example, any user input mechanism described herein above may be used.

In step 1312, a trajectory is determined based on the physical position and/or orientation determined in step 1308. Accordingly, in some embodiments, step 1308 is only performed in response to step 1310. Also accordingly, in some embodiments, step 1308 is performed continuously over a period of time [e.g., with a certain frequency (e.g., more than about once a second)] and the trajectory is determined based on the most recent physical position and/or orientation determined when the user input signal is received. In step 1314, the trajectory is output to a robotic surgical system (e.g., for use in performing a surgical procedure). In optional step 1316, trajectory augmentation graphics that represent the trajectory determined in step 1312 are displayed on a display screen of the augmented reality navigation system, for example, in accordance with the embodiments discussed above (in reference to exemplary method 1200). The trajectory augmentation graphics may be modified (e.g., using a registration and/or unified coordinate system) prior to display on a display screen.

Exemplary method 1300 includes optional steps 1318 and 1320. Either or both of the optional steps may be a part of a method. In step optional 1318, a haptic object comprising the trajectory determined in step 1312 is defined. The haptic object may be determined by the augmented reality navigation system (e.g., using relative position(s) and/or orientation(s) of real-world features detected by a detector of the system) and provided to a robotic surgical system by the computer subsystem of the augmented reality navigation system. The robotic surgical system may then be confined in its motion such that at least a portion of a surgical tool connected to or inserted into the robotic surgical system cannot move outside of the haptic object (e.g., due to haptic feedback provided to a surgeon operating the robotic surgical system). In optional step 1320, output from the augmented reality navigation system causes the robotic surgical system to automatically align with the represented trajectory and/or automatically move along the trajectory. In some embodiments, representations of multiple trajectories may be displayed simultaneously and a surgeon may select one of the represented trajectories to have the robotic surgical system align to (e.g., using a pointer tool). In some embodiments, whether one or multiple representations of trajectories are displayed, the augmentation graphics used may appear overlaid over a patient anatomy to give a surgeon an accurate view of how the trajectory intersects a patient's anatomy. In some embodiments, portions of a surgical tool and/or its trajectories appear on a virtual display screen viewed through a display screen of a head mounted display (e.g., in spatial correspondence with a model of patient anatomy such that the trajectory representation, portion of a surgical tool, and model appear to have the same relative position and orientation as physical reality). For example, a virtual display screen may appear as panel A or panel B of FIG. 15. Overlaid augmentation graphics may appear as the sketch in FIG. 16 illustrates.

A model of patient anatomy may be displayed as overlaid augmentation graphics during exemplary method 1300 in order to assist a surgeon in defining a trajectory. A plurality of desired trajectories may be defined. A trajectory selection guidance augmentation graphic may also be used to select one of a plurality of defined trajectories (e.g., pre- and/or intra-operatively defined trajectories) by orienting a head mounted display such that a trajectory selection guidance augmentation graphic appears to coincide with one of the plurality of trajectories. A previously defined trajectory may also be updated using exemplary method 1300 by loading and/or selecting the predefined trajectory and then following exemplary method 1300 to revise a position and/or orientation of the trajectory.

Figure 14:
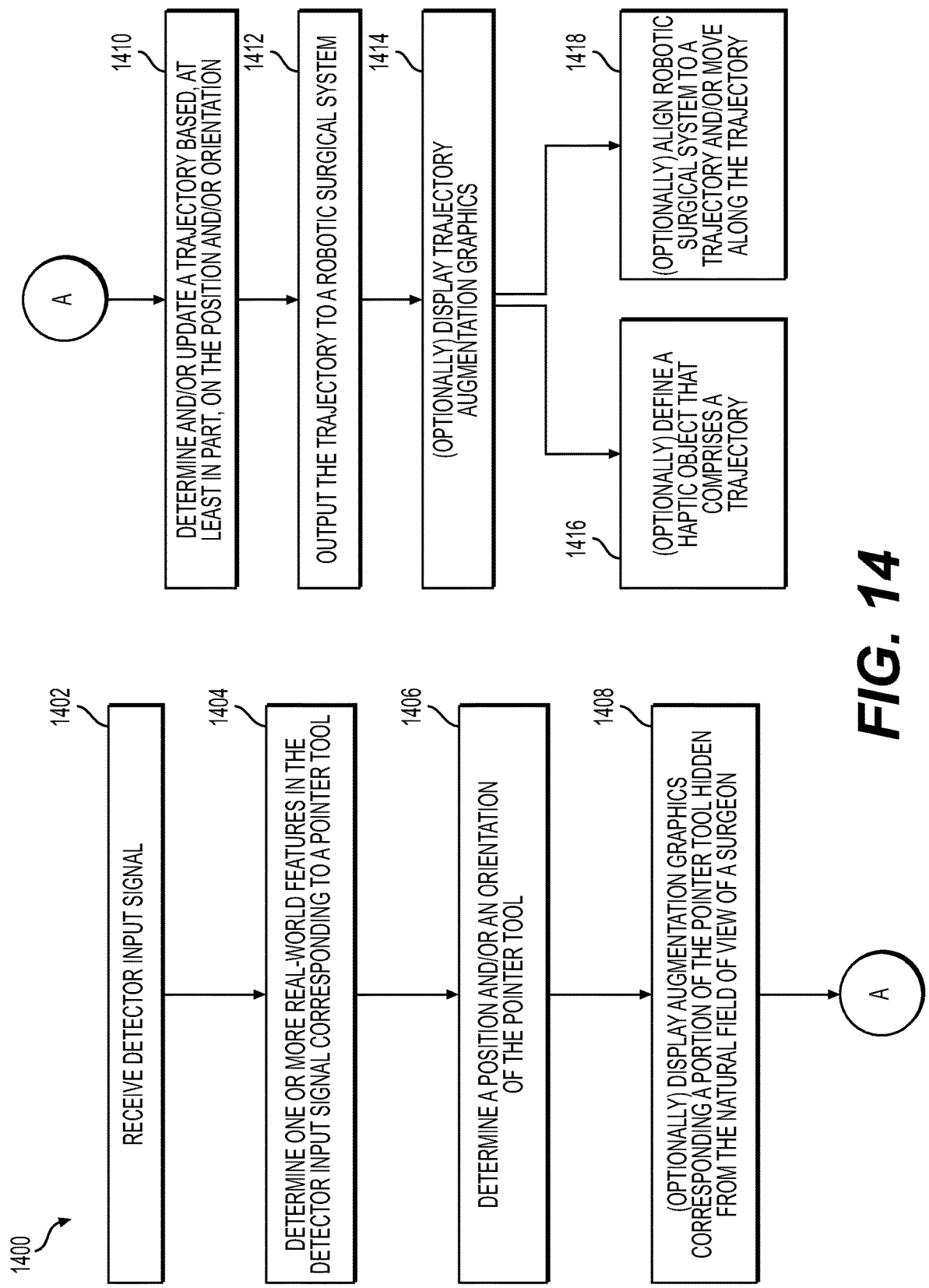
FIG. 14 is a block diagram of an exemplary method for using an augmented reality navigation system with a pointer tool, according to illustrative embodiments of the invention.

Referring now to the block flow diagram shown in FIG. 14, exemplary method 1400 is a method of using an augmented reality navigation system in accordance with some embodiments of the present disclosure. Exemplary method 1400 is a method whereby an augmentation reality navigation system detects a pointer tool to assist in planning and/or updating one or more trajectories corresponding to a surgical procedure. In some embodiments, an augmented reality navigation system comprises a pointer tool. The computational steps of exemplary method 1400 may be performed by a computer subsystem of an augmented reality navigation system.

In step 1402, one or more detectors mounted on a head mounted display of an augmented reality navigation system generate a detector input signal that is received by a computer subsystem of the augmented reality navigation system. The detector input signal represents a field of view of the one or more detectors that comprises at least a portion of a patient anatomy (e.g., relevant to a surgical procedure to be performed). In step 1404, a relative position and/or orientation for one or more real-world features in the detector input signal (i.e., in the field of view represented by the detector input signal) corresponding to a pointer tool are determined. The relative position and/or orientation may be determined in real time or may be taken as an absolute position and/or orientation represented in a unified coordinate system that resulted from a registration of an augmented reality navigation system and a surgical environment (e.g., a registration between the augmented reality navigation system and objects in the surgical environment such as a patient, a surgical tool, and a robotic surgical system, for example). The detector input signal may be received by a computer subsystem from one or more detectors mounted to a head mounted display of the augmented reality navigation system, one or more detectors mounted to a head mounted display of a second augmented reality navigation system, and/or one or more auxiliary detectors positioned throughout a surgical environment. In step 1406, a position and/or an orientation of the pointer tool are determined based on the relatively position and/or orientation for the real-world features determined in step 1404. For example, the coordinates of the physical position and/or orientation of the pointer tool may be determined using a unified coordinate system defined during a registration procedure.

In optional step 1408, augmentation graphics corresponding to a representation of a portion of the pointer tool hidden from the natural field of view of the surgeon are displayed on a display screen of the head mounted display. The augmentation graphics may appear overlaid over a patient anatomy such that a surgeon can accurately visual the hidden portion of the pointer tool while positioning and/or orienting it. Augmentation graphics corresponding to a model of a patient anatomy may additionally be overlaid over the patient anatomy to provide further navigational information. Alternatively or additionally, the pointer tool augmentation graphics may appear on a virtual display screen alongside an oriented model of patient anatomy such that the position and orientation of the pointer tool relative to the model (e.g., medical image data) in the virtual display accurately represents the true physical relationship between the pointer tool and the patient's anatomy.

In step 1410, a trajectory is determined and/or updated based, at least in part, on the position and/or orientation of the pointer tool determined in step 1406. In some embodiments, a pointer tool may be used to select a plurality of points in space that are then used to collectively determine a trajectory (e.g., a linear or non-linear trajectory). The trajectory may be determined in step 1410 in response to a user input signal received by the computer subsystem, wherein the user input signal is generated due to an action (e.g., gesture) by a surgeon using the augmented reality navigation system and the action is made when the pointer tool is in a desired position and/or orientation. For example, any user input mechanism described herein above may be used. In some embodiments, steps 1402-1410 are repeated one or more times in order to define a plurality of trajectories. In step 1412, the trajectory (or plurality of trajectories) is output to a robotic surgical system (e.g., for use in performing a surgical procedure). In optional step 1414, trajectory augmentation graphics that represent the trajectory determined in step 1412 are displayed on a display screen of the augmented reality navigation system, for example, in accordance with the embodiments discussed above (in reference to exemplary method 1200). The trajectory augmentation graphics may be modified (e.g., using a registration and/or unified coordinate system) prior to display on a display screen.

Exemplary method 1400 additionally includes optional steps 1416 and 1418. Either or both of the optional steps may be a part of a method. In optional step 1416, a haptic object comprising the trajectory determined in step 1410 is defined. The haptic object may be determined by the augmented reality navigation system (e.g., using relative position(s) and/or orientation(s) of real-world features detected by a detector of the system) and provided to a robotic surgical system by the computer subsystem of the augmented reality navigation system. The robotic surgical system may then be confined in its motion such that at least a portion of a surgical tool connected to or inserted into the robotic surgical system cannot move outside of the haptic object (e.g., due to haptic feedback provided to a surgeon operating the robotic surgical system). In optional step 1418, output from the augmented reality navigation system causes the robotic surgical system to automatically align with the represented trajectory and/or automatically move along the trajectory. In some embodiments, representations of multiple trajectories may be displayed simultaneously and a surgeon may select one of the represented trajectories to have the robotic surgical system align to (e.g., using a pointer tool). In some embodiments, whether one or multiple representations of trajectories are displayed, the augmentation graphics used may appear overlaid over a patient anatomy to give a surgeon an accurate view of how the trajectory intersects a patient's anatomy. In some embodiments, portions of a surgical tool and/or its trajectories appear on a virtual display screen viewed through a display screen of a head mounted display (e.g., in spatial correspondence with a model of patient anatomy such that the trajectory representation, portion of a surgical tool, and model appear to have the same relative position and orientation as physical reality). For example, a virtual display screen may appear as panel A or panel B of FIG. 15. Overlaid augmentation graphics may appear as the sketch in FIG. 16 illustrates.

A single augmented reality navigation system may be configured to perform, inter alia, each of exemplary method 1200, exemplary method 1300, and exemplary 1400. A choice of a particular method to define a trajectory or a particular type of augmentation graphic to display may depend on the surgical procedure being performed. For example, surgeons may prefer augmentation graphics and/or trajectories definition methods when performing certain minimally invasive surgery (MIS) procedures that are different than those used when performing an equivalent traditional (i.e., non-MIS) procedure. Likewise, methods and graphics may depend on particular surgeon performing a procedure or a particular patient. Thus, in certain embodiments, an augmented reality navigation system can store settings on a per procedure, per patient, and/or per surgeon basis. In some embodiments, patient health information is displayed on one or more virtual display screens while navigational information is displayed using overlaid augmentation graphics and, optionally, on an additional virtual display.

The following is a description of an exemplary use of an illustrative embodiment of an augmented reality navigation system. After the augmented reality navigation system receives a patient's medical image data, a user interface displayed on a display screen of the augmented reality navigation system enables planning of a surgical procedure by allowing the surgeon to navigate a model derived from the medical image data and position virtual representations of surgical implants and/or trajectories as desired. Positioning may occur using surgeon input (e.g., via a motion sensor or an auxiliary input device). The augmented reality navigation system is then used to track positions of a robotic arm and one or more real-world features associated with the patient (e.g., as detected by a detector). Throughout, the augmented reality navigation system synchronizes its coordinate system with that of the patient anatomy and robotic surgical system (for example, by periodic or continuous re-registration). Upon receiving input from the surgeon, for example, via a motion sensor, the augmented reality navigation system causes the end-effector of the robotic arm to be automatically positioned in alignment with a planned trajectory, compensating at all times for shifts in the position of the patient and allowing treatment while avoiding critical anatomical structures.

In another exemplary use, a model derived from medical image data is registered in order to plan an implant trajectory. In certain embodiments, a medical image itself (corresponding to the medical image data) is used as a model of patient anatomy. A particular registration method may be chosen based on the imaging technique used to generate the medical image data. The imaging may be done pre- or intraoperatively. Once registered, the surgeon will use augmentation graphics displayed on a display screen of a head mounted display to determine necessary trajectories and locations for surgical implants. Once planning is complete, input from the surgeon can cause a robotic arm of a robotic surgical system to move automatically onto a planned trajectory. If multiple trajectories are planned, the surgeon may move the end effector close to the first planned trajectory. Alternatively, the first planned trajectory can be selected using user input (e.g., into a motion sensor). The augmented reality navigation system will indicate which planned trajectory is in range on the display screen and the system will slowly move the robotic arm onto the selected (e.g., proximal) planned trajectory. Augmentation graphics can be used to indicate once the selected planned trajectory has been achieved and motion can be limited along that trajectory. The surgeon will then use surgical tool(s) connected to the robotic surgical system to insert the desired surgical implant. The navigation camera will track the positions of the tool(s) in real time and display the models on the display screen, for example, appearing overlaid over the patient anatomy.

In certain embodiments, augmented reality navigation systems disclosed herein can be used by medical specialties that can benefit from both augmented reality visualization and precision motion tracking (e.g., trauma, navigated spine, pre-planned cranial). In certain embodiments, augmented reality navigation systems disclosed herein can be used in open, percutaneous, minimally invasive surgical (MIS) procedures performed in the operating room or interventional outpatient procedures, all of which may contain some form of patient imaging. In certain embodiments, augmented reality navigation systems disclosed herein will be valuable in any such procedure which requires the surgeon(s) to view remote displays with critical navigational information and to mentally translate that information into the surgical space or within the patient. For example, a surgical procedure in which an augmented reality navigation system disclosed herein is used may be a spinal procedure, an orthopedic procedure, an orthopedic trauma procedure, a neurosurgical procedure, a minimally invasive procedure or any combination thereof. In certain embodiments, augmented reality navigation systems are used for training, for example, in simulations of surgical procedures using a cadaver or prosthetic model of patient anatomy.

Figure 17:
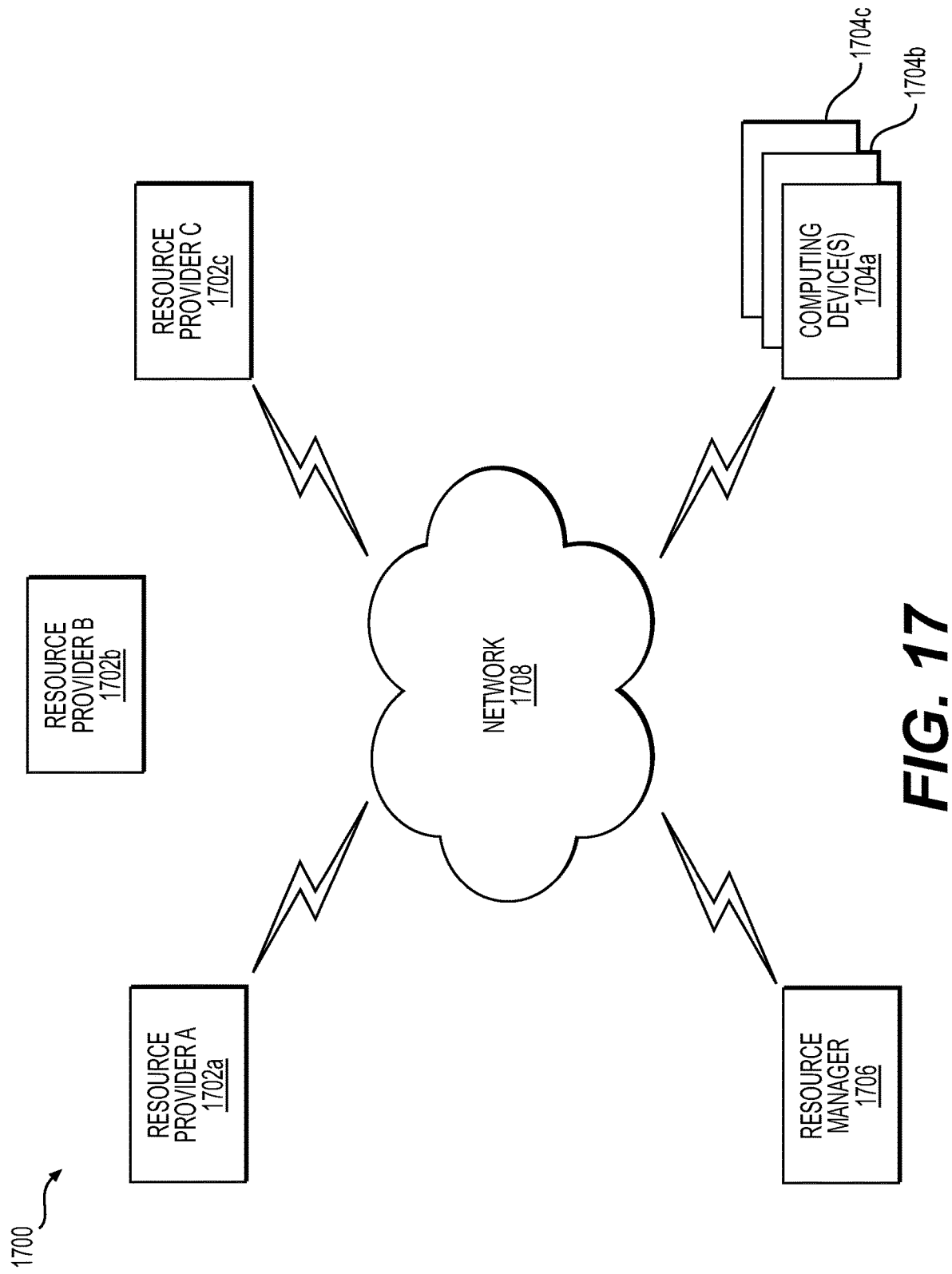
FIG. 17 is a block diagram of an example network environment for use in the methods and systems described herein, according to illustrative embodiments of the invention.

Exemplary embodiments of systems and methods disclosed herein were described above with reference to computations performed locally by a computing device. However, computations performed over a network are also contemplated. FIG. 17 shows an illustrative network environment 1700 for use in the methods and systems described herein. In brief overview, referring now to FIG. 17, a block diagram of an exemplary cloud computing environment 1700 is shown and described. The cloud computing environment 1700 may include one or more resource providers 1702a, 1702b, 1702c (collectively, 1702). Each resource provider 1702 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1702 may be connected to any other resource provider 1702 in the cloud computing environment 1700. In some implementations, the resource providers 1702 may be connected over a computer network 1708. Each resource provider 1702 may be connected to one or more computing device 1704a, 1704b, 1704c (collectively, 1704), over the computer network 1708.

The cloud computing environment 1700 may include a resource manager 1706. The resource manager 1706 may be connected to the resource providers 1702 and the computing devices 1704 over the computer network 1708. In some implementations, the resource manager 1706 may facilitate the provision of computing resources by one or more resource providers 1702 to one or more computing devices 1704. The resource manager 1706 may receive a request for a computing resource from a particular computing device 1704. The resource manager 1706 may identify one or more resource providers 1702 capable of providing the computing resource requested by the computing device 1704. The resource manager 1706 may select a resource provider 1702 to provide the computing resource. The resource manager 1706 may facilitate a connection between the resource provider 1702 and a particular computing device 1704. In some implementations, the resource manager 1706 may establish a connection between a particular resource provider 1702 and a particular computing device 1704. In some implementations, the resource manager 1706 may redirect a particular computing device 1704 to a particular resource provider 1702 with the requested computing resource.

Figure 18:
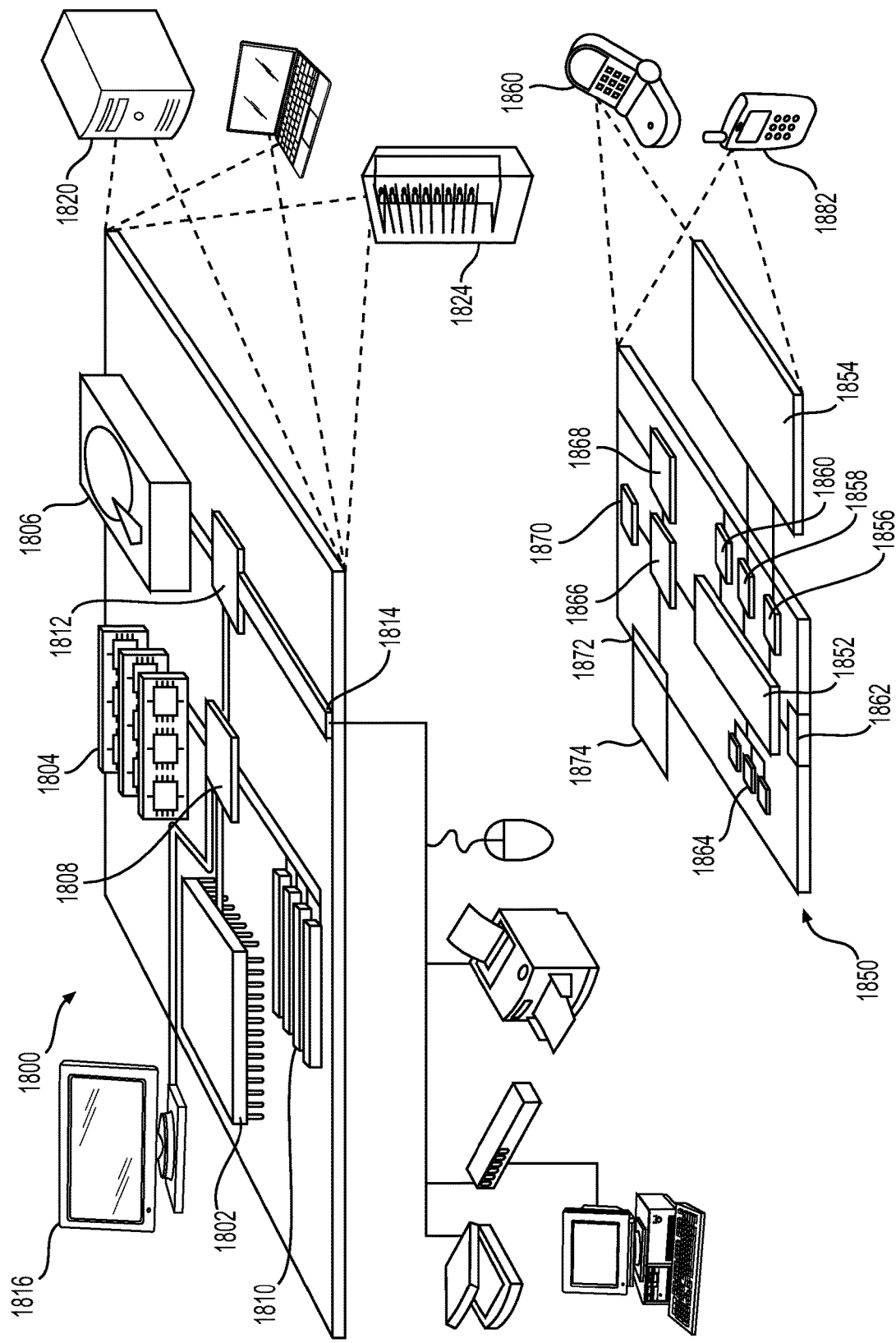
FIG. 18 is a block diagram of an example computing device and an example mobile computing device, for use in illustrative embodiments of the invention.

FIG. 18 shows an example of a computing device 1800 and a mobile computing device 1850 that can be used in the methods and systems described in this disclosure. The computing device 1800 is intended to represent various forms of digital computers, such as laptops, desktops, workstations, personal digital assistants, servers, blade servers, mainframes, and other appropriate computers. The mobile computing device 1850 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1800 includes a processor 1802, a memory 1804, a storage device 1806, a high-speed interface 1808 connecting to the memory 1804 and multiple high-speed expansion ports 1810, and a low-speed interface 1812 connecting to a low-speed expansion port 1814 and the storage device 1806. Each of the processor 1802, the memory 1804, the storage device 1806, the high-speed interface 1808, the high-speed expansion ports 1810, and the low-speed interface 1812, are interconnected using various busses, and may be mounted on a common motherboard or in other manners as appropriate. The processor 1802 can process instructions for execution within the computing device 1800, including instructions stored in the memory 1804 or on the storage device 1806 to display graphical information for a GUI on an external input/output device, such as a display 1816 coupled to the high-speed interface 1808. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (e.g., one or more processors) of any number of computing devices (e.g., one or more computing devices). Furthermore, where a function is described as being performed by "a processor", this encompasses embodiments wherein the function is performed by any number of processors (e.g., one or more processors) of any number of computing devices (e.g., one or more computing devices) (e.g., in a distributed computing system).

The memory 1804 stores information within the computing device 1800. In some implementations, the memory 1804 is a volatile memory unit or units. In some implementations, the memory 1804 is a non-volatile memory unit or units. The memory 1804 may also be another form of computer-readable medium, such as a magnetic or optical disk.

The storage device 1806 is capable of providing mass storage for the computing device 1800. In some implementations, the storage device 1806 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1802), perform one or more methods, such as those described above. The instructions can also be stored by one or more storage devices such as computer- or machine-readable mediums (for example, the memory 1804, the storage device 1806, or memory on the processor 1802).

The high-speed interface 1808 manages bandwidth-intensive operations for the computing device 1800, while the low-speed interface 1812 manages lower bandwidth-intensive operations. Such allocation of functions is an example only. In some implementations, the high-speed interface 1808 is coupled to the memory 1804, the display 1816 (e.g., through a graphics processor or accelerator), and to the high-speed expansion ports 1810, which may accept various expansion cards (not shown). In the implementation, the low-speed interface 1812 is coupled to the storage device 1806 and the low-speed expansion port 1814. The low-speed expansion port 1814, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1800 may be implemented in a number of different forms, as shown in the figure. For example, it may be implemented as a standard server 1820, or multiple times in a group of such servers. In addition, it may be implemented in a personal computer such as a laptop computer 1822. It may also be implemented as part of a rack server system 1824. Alternatively, components from the computing device 1800 may be combined with other components in a mobile device (not shown), such as a mobile computing device 1850. Each of such devices may contain one or more of the computing device 1800 and the mobile computing device 1850, and an entire system may be made up of multiple computing devices communicating with each other.

The mobile computing device 1850 includes a processor 1852, a memory 1864, an input/output device such as a display 1854, a communication interface 1866, and a transceiver 1868, among other components. The mobile computing device 1850 may also be provided with a storage device, such as a micro-drive or other device, to provide additional storage. Each of the processor 1852, the memory 1864, the display 1854, the communication interface 1866, and the transceiver 1868, are interconnected using various buses, and several of the components may be mounted on a common motherboard or in other manners as appropriate.

The processor 1852 can execute instructions within the mobile computing device 1850, including instructions stored in the memory 1864. The processor 1852 may be implemented as a chipset of chips that include separate and multiple analog and digital processors. The processor 1852 may provide, for example, for coordination of the other components of the mobile computing device 1850, such as control of user interfaces, applications run by the mobile computing device 1850, and wireless communication by the mobile computing device 1850.

The processor 1852 may communicate with a user through a control interface 1858 and a display interface 1856 coupled to the display 1854. The display 1854 may be, for example, a TFT (Thin-Film-Transistor Liquid Crystal Display) display or an OLED (Organic Light Emitting Diode) display, or other appropriate display technology. The display interface 1856 may comprise appropriate circuitry for driving the display 1854 to present graphical and other information to a user. The control interface 1858 may receive commands from a user and convert them for submission to the processor 1852. In addition, an external interface 1862 may provide communication with the processor 1852, so as to enable near area communication of the mobile computing device 1850 with other devices. The external interface 1862 may provide, for example, for wired communication in some implementations, or for wireless communication in other implementations, and multiple interfaces may also be used.

The memory 1864 stores information within the mobile computing device 1850. The memory 1864 can be implemented as one or more of a computer-readable medium or media, a volatile memory unit or units, or a non-volatile memory unit or units. An expansion memory 1874 may also be provided and connected to the mobile computing device 1850 through an expansion interface 1872, which may include, for example, a SIMM (Single In Line Memory Module) card interface. The expansion memory 1874 may provide extra storage space for the mobile computing device 1850, or may also store applications or other information for the mobile computing device 1850. Specifically, the expansion memory 1874 may include instructions to carry out or supplement the processes described above, and may include secure information also. Thus, for example, the expansion memory 1874 may be provided as a security module for the mobile computing device 1850, and may be programmed with instructions that permit secure use of the mobile computing device 1850. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 1852), perform one or more methods, such as those described above. The instructions can also be stored by one or more storage devices, such as one or more computer- or machine-readable mediums (for example, the memory 1864, the expansion memory 1874, or memory on the processor 1852). In some implementations, the instructions can be received in a propagated signal, for example, over the transceiver 1868 or the external interface 1862.

The mobile computing device 1850 may communicate wirelessly through the communication interface 1866, which may include digital signal processing circuitry where necessary. The communication interface 1866 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1868 using a radio-frequency. In addition, short-range communication may occur, such as using a Bluetooth®, Wi-Fi™, or other such transceiver (not shown). In addition, a GPS (Global Positioning System) receiver module 1870 may provide additional navigation- and location-related wireless data to the mobile computing device 1850, which may be used as appropriate by applications running on the mobile computing device 1850.

The mobile computing device 1850 may also communicate audibly using an audio codec 1860, which may receive spoken information from a user and convert it to usable digital information. The audio codec 1860 may likewise generate audible sound for a user, such as through a speaker, e.g., in a handset of the mobile computing device 1850. Such sound may include sound from voice telephone calls, may include recorded sound (e.g., voice messages, music files, etc.) and may also include sound generated by applications operating on the mobile computing device 1850.

The mobile computing device 1850 may be implemented in a number of different forms, as shown in the figure. For example, it may be implemented as a cellular telephone 1880. It may also be implemented as part of a smart-phone 1882, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, modules or computational subsystems (e.g. a position tracking module and user input module) described herein can be separated, combined or incorporated into single or combined modules. Modules and arrangements thereof depicted in figures are not intended to limit the systems and methods described herein to the software architectures shown therein.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

Having described certain implementations of augmented reality navigation systems for use with a robotic surgical system and methods of their use, it will now become apparent to one of skill in the art that other implementations incorporating the concepts of the disclosure may be used. Therefore, the disclosure should not be limited to certain implementations, but rather should be limited only by the spirit and scope of the following claims.

What is claimed is:

1. An augmented reality navigation system comprising:
 a head mounted display comprising an at least partially transparent display screen configured to display augmentation graphics, wherein the display screen is configured to allow the user to see a natural field of view of the user while seeing the augmentation graphics overlaid on the natural field of view;
 at least one detector for identifying real-world features, the at least one detector connected to the head mounted display;
 a surgical tool having markers and configured to be detected by at the at least one detector, wherein a representation of at least a portion of the surgical tool and/or a trajectory of the surgical tool is presented in the head mounted display,
 wherein a detector input signal from the at least one detector corresponds to a field of view of the at least one detector and the field of view comprises at least a portion of anatomy of a patient during a surgical procedure,
 wherein the detector input signal includes a relative location and/or orientation for each of one or more of the real-world features wherein the display screen displays at least three operational views simultaneously, and wherein the at least three operational views may be separately activated by changing a pitch angle of the head mounted display.

2. The augmented reality navigation system of claim 1, wherein a camera system for detecting real-world features is electrically coupled to the head mounted display.

3. The augmented reality navigation system of claim 1, wherein the head mounted display provides a representation of the surgical tool and a trajectory of the surgical tool overlaid on the anatomy of the patient.

4. The augmented reality navigation system of claim 1, further includes a motion sensor connected to the head mounted display for outputting a motion signal based on measured motion of the head mounted display.

5. The augmented reality navigation system of claim 1, wherein the at least one detector comprises a detector with at least a minimum field of view of 40 degrees.

6. The augmented reality navigation system of claim 1, wherein the display screen has a resolution of at least 1280×720 pixels.

7. The augmented reality navigation system of claim 1, comprising a pointer tool for making surgical planning selections, wherein the pointer tool is configured to be detected by the at least one detector.

8. The augmented reality navigation system of claim 1, wherein the at least one detector comprises a video camera and transmits a video signal to the head mounted display to display augmentation graphics which appear to the user to be superimposed on at least a portion of a natural field of view of the user.

9. The augmented reality navigation system of claim 1, wherein the navigation system is used to perform a surgical procedure.

10. An augmented reality navigation system for use with a robotic surgical system, the system comprising:
a head mounted display comprising an at least partially transparent display screen configured to display augmentation graphics, wherein the display screen is configured to allow the user to see a natural field of view of the user while seeing the augmentation graphics overlaid on the natural field of view;
at least one detector for identifying real-world features, the at least one detector connected to the head mounted display; and
a computer subsystem configured to generate and/or access a representation of at least a portion of a surgical tool and/or a trajectory of the surgical tool during a surgical procedure, modify at least a portion of the representation based on a relative position and/or orientation of one or more real-world features in a detector input signal received from the at least one detector, and display, on the display screen, surgical tool augmentation graphics based on the modified representation
wherein the display screen displays at least three operational views simultaneously, and wherein the at least three operational views may be separately activated by changing a pitch angle of the head mounted display.

11. The augmented reality navigation system of claim 10, wherein the computer subsystem is configured to render a surgical tool augmentation graphic for each of a plurality of surgical tool trajectories, and display, on the display screen, the plurality of surgical tool augmentation graphics such that the surgical tool augmentation graphics appear overlaid on an anatomy of the patient and each of the trajectory augmentation graphics indicate a physical trajectory that could be followed during the surgical procedure.

12. The augmented reality navigation system of claim 10, wherein
the computer subsystem is configured to modify an anatomical model of a patient based on one or more relative location(s) and/or orientation(s) determined from the detected input signal, thereby forming an updated anatomical model, and
the computer subsystem is configured to display, on the display screen, anatomical model augmentation graphics corresponding to the updated anatomical model such that the updated anatomical model appears overlaid on an anatomy of the patient.

13. The augmented reality navigation system of claim 10, comprising:
a motion sensor connected to the head mounted display for outputting a motion signal based on measured motion of the head mounted display.

14. An augmented reality navigation system comprising:
a head mounted display comprising an at least partially transparent display screen configured to display augmentation graphics, wherein the display screen is configured to allow the user to see a natural field of view of the user while seeing the augmentation graphics overlaid on the natural field of view; and
at least one detector for identifying real-world features, the at least one detector connected to the head mounted display;
wherein a detector input signal from the at least one detector corresponds to a field of view of the at least one detector and the field of view comprises at least a portion of anatomy of a patient during a surgical procedure,
wherein the detector input signal includes a relative location and/or orientation for each of one or more of the real-world features,
wherein the display screen displays at least three operational views simultaneously, and wherein the at least three operational views may be separately activated by changing a pitch angle of the head mounted display.

15. The augmented reality navigation system of claim 14, wherein a camera system for detecting real-world features is electrically coupled to the head mounted display.

16. The augmented reality navigation system of claim 14, wherein the head mounted display provides a representation of a surgical tool and a trajectory of the surgical tool overlaid on an anatomy of the patient.

17. The augmented reality navigation system of claim 14, further includes a motion sensor connected to the head mounted display for outputting a motion signal based on measured motion of the head mounted display.

18. The augmented reality navigation system of claim 14, comprising a pointer tool for making surgical planning selections, wherein the pointer tool is configured to be detected by the at least one detector.

19. The augmented reality navigation system of claim 14, wherein the at least one detector comprises a video camera and transmits a video signal to the head mounted display to display augmentation graphics which appear to the user to be superimposed on at least a portion of a natural field of view of the user.

20. The augmented reality navigation system of claim 14, wherein the navigation system is used to perform a surgical procedure.

\* \* \* \* \*